(12) United States Patent
Isakson

(10) Patent No.: US 11,331,375 B2
(45) Date of Patent: *May 17, 2022

(54) COMPOSITIONS AND METHODS FOR REGULATING LEUKOCYTE ADHESION

(71) Applicant: University of Virginia Patent Foundation, Charlottesville, VA (US)

(72) Inventor: Brant E. Isakson, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 329 days.

This patent is subject to a terminal disclaimer.

(21) Appl. No.: 15/746,484

(22) PCT Filed: Jul. 29, 2016

(86) PCT No.: PCT/US2016/044683
§ 371 (c)(1),
(2) Date: Jan. 22, 2018

(87) PCT Pub. No.: WO2017/019952
PCT Pub. Date: Feb. 2, 2017

(65) Prior Publication Data
US 2018/0207238 A1 Jul. 26, 2018

Related U.S. Application Data

(60) Provisional application No. 62/198,480, filed on Jul. 29, 2015.

(51) Int. Cl.
| | |
|---|---|
| A61K 38/10 | (2006.01) |
| A61K 38/20 | (2006.01) |
| C07K 14/435 | (2006.01) |
| A61P 7/00 | (2006.01) |
| A61P 29/00 | (2006.01) |
| A61K 38/17 | (2006.01) |
| G01N 33/50 | (2006.01) |

(52) U.S. Cl.
CPC ...... *A61K 38/2013* (2013.01); *A61K 38/1709* (2013.01); *A61P 7/00* (2018.01); *A61P 29/00* (2018.01); *C07K 14/435* (2013.01); *G01N 33/5064* (2013.01); *C07K 2319/10* (2013.01); *G01N 2800/328* (2013.01)

(58) Field of Classification Search
CPC .................................................. A61K 38/2013
See application file for complete search history.

(56) References Cited

U.S. PATENT DOCUMENTS

| | | | |
|---|---|---|---|
| 4,554,101 A | 11/1985 | Hopp | |
| 10,314,883 B2 * | 6/2019 | Isakson | C07K 7/06 |
| 2010/0311647 A1 | 12/2010 | Halem et al. | |
| 2011/0076258 A1 | 3/2011 | Grassi et al. | |
| 2013/0156791 A1 | 6/2013 | Perfettini et al. | |
| 2018/0028595 A1 | 2/2018 | Isakson et al. | |
| 2018/0207238 A1 | 7/2018 | Isakson | |
| 2019/0008921 A1 * | 1/2019 | Wang | A61K 39/395 |
| 2020/0016232 A1 | 1/2020 | Isakson et al. | |

FOREIGN PATENT DOCUMENTS

| | | |
|---|---|---|
| WO | WO 2005/007090 A2 | 1/2005 |
| WO | WO 2016/130966 A1 | 8/2016 |

OTHER PUBLICATIONS

Silverman, W., et al. Probenecid, a gout remedy, inhibits pannexin 1 channels. Am. J. Physiol. Cell Physiol. 2008, 295:C761-C767.*
Willebrords, J. et al. Inhibitors of connexin and pannexin channels as potential therapeutics. Pharmacol. Ther., 2017, 180:144-160.*
Adamson, S.E. et al. Pannexin 1 is required for full activation of insulin-stimulated glucose uptake in adipocytes. Molecular Metabolism, 2015, 4:610-618.*
Lee, V.R., et al. Pannexin 1 regulates adipose stromal cell differentiation and fat accumulation. Scientific Reports, 2018, 8:16166, p. 1-14.*
Mehaffey, E., et al. Tumor necrosis factor-alpha, kidney function, and hypertension. Am. J. Physiol. Renal Physiol., 2017, 313: F1005-F1008.*
Penuela, S., et al. Pannexin 1 and pannexin 3 regulate body fat accumulation in mouse models of diet induced obesity. FASEB J., vol. 33, Issue S1, p. 796. 13.*
Qu, Y., et al. Pannexin-1 is required for ATP release during apoptosis but not for inflammasome activation. Journal of Immunology, 2011, 186:6553-6561.*
Lohmann, et al., "Pannexin 1-dependent ATP release from venous endothelium promotes acute vascular inflammation". The FASEB Journal (Apr. 2014), vol. 28, No. 1, Supplement 669.8 [retrieved on Oct. 5, 2016 from http://www.fasebj.org/content/28/1_Supplement/669.8.short].abstract.
Lohmann, et al., "Mechanisms of ATP release and signalling in the blood vessel wall", Cardiovascular Research 95.3 (2012): 269-280, especially p. 274; p. 275; p. 277.

(Continued)

*Primary Examiner* — Prema M Mertz
(74) *Attorney, Agent, or Firm* — Jenkins, Wilson, Taylor & Hunt

(57) ABSTRACT

Inflammatory cell recruitment to local sites of tissue injury and/or infection is controlled by many signaling processes influencing cell-to-cell interactions between vascular endothelial cells (EC) in post-capillary venules and circulating leukocytes. Here we report that the ATP-release channel Pannexin1 (Panx1) opens downstream of EC activation by tumor necrosis factor α (TNF α). This process involves activation of Type 1 TNF receptors, recruitment of Src Family Kinases (SFK), and SFK-dependent phosphorylation of Panx1. We report a previously unidentified role for Panx1 channels in promoting leukocyte adhesion and emigration through the venous wall during acute systemic inflammation. The present application further discloses that Panx IL2 peptide consisting of amino acid sequence KYP-IVEQYLKYGRKKQRR (SEQ ID NO: 3) or $^{10}$Panx1 peptide consisting of amino acid sequence RQAAFVDSY (SEQ ID NO: 8) are inhibitors of leukocyte adhesion.

38 Claims, 41 Drawing Sheets
(33 of 41 Drawing Sheet(s) Filed in Color)
Specification includes a Sequence Listing.

(56) References Cited

OTHER PUBLICATIONS

Zerr, M. et al., "Major contribution of the P2Y(1)receptor in purinergic regulation of TNFalpha-induced vascular inflammation", Circulation 123, 2404-2413, doi:10.1161/CIRCULATIONAHA.110.002139 (2011).

Lohman, A. W. et al., "Expression of pannexin isoforms in the systemic murine arterial network", Journal of vascular research 49, 405-416, doi:10.1159/000338758 (2012).

Billaud, M. et al., "Pannexin1 regulates alpha1-adrenergic receptor-mediated vasoconstriction", Circulation research 109, 80-85, doi:10.1161/CIRCRESAHA.110.237594 (2011).

Gaynullina, D., Shestopalov, V. I., Panchin, Y. & Tarasova, O. S., "Pannexin 1 facilitates arterial relaxation via an endothelium-derived hyperpolarization mechanism", FEBS letters 589, 1164-1170, doi: 10.1016/j.febslet.2015.03.018 (2015).

Gaynullina, D., Tarasova, O. S., Kiryukhina, O. O., Shestopalov, V. I. & Panchin, Y., "Endothelial function is impaired in conduit arteries of pannexin1 knockout mice", Biol Direct 9, 8, doi:10.1186/1745-6150-9-8 (2014).

Bao, L., Locovei, S. & Dahl, G., "Pannexin membrane channels are mechanosensitive conduits for ATP", FEBS letters 572, 65-68, doi:10.1016/j.febslet.2004.07.009 (2004).

Lohman, A. W. et al., "S-nitrosylation inhibits pannexin 1 channel function", The Journal of biological chemistry 287, 39602-39612, doi:10.1074/jbc.M112.397976 (2012).

Adamson, S. E. & Leitinger, N., "The role of pannexin1 in the induction and resolution of inflammation", FEBS letters 588, 1416-1422, doi:10.1016/j.febslet.2014.03.009 (2014).

Silverman, W. R. et al., "The pannexin 1 channel activates the inflammasome in neurons and astrocytes", The Journal of biological chemistry 284, 18143-18151, doi:10.1074/jbc.M109.004804 (2009).

Chekeni, F. B. et al., "Pannexin 1 channels mediate 'find-me' signal release and membrane permeability during apoptosis", Nature 467, 863-867, doi:10.1038/nature09413 (2010).

Lohman, A. W. & Isakson, B. E., "Differentiating connexin hemichannels and pannexin channels in cellular ATP release", FEBS letters 588, 1379-1388, doi:10.1016/j.febslet.2014.02.004 (2014).

Pincheira, R., Castro, A. F., Ozes, O. N., Idumalla, P. S. & Donner, D. B., "Type 1 TNF receptor forms a complex with and uses Jak2 and c-Src to selectively engage signaling pathways that regulate transcription factor activity", J Immunol 181, 1288-1298 (2008).

Xing, L. et al., "Genetic evidence for a role for Src family kinases in TNF family receptor signaling and cell survival", Genes & development 15, 241-253 (2001).

Weilinger, N. L., Tang, P. L. & Thompson, R. J., "Anoxia-induced NMDA receptor activation opens pannexin channels via Src family kinases", The Journal of neuroscience : the official journal of the Society for Neuroscience 32, 12579-12588, doi:10.1523/JNEUROSCI.1267-12.2012 (2012).

Billaud, M. et al., "A molecular signature in the pannexin1 intracellular loop confers channel activation by the alpha1 adrenoreceptor in smooth muscle cells", Sci Signal 8, ra17, doi:10.1126/scisignal.2005824 (2015).

Sandilos, J. K. et al., "Pannexin 1, an ATP release channel, is activated by caspase cleavage of its pore-associated C-terminal autoinhibitory region", The Journal of biological chemistry 287, 11303-11311, doi:10.1074/jbc.M111.323378 (2012).

Dourado, M., Wong, E. & Hackos, D. H., "Pannexin-1 is blocked by its C-terminus through a delocalized non-specific interaction surface", PLoS One 9, e99596, doi:10.1371/journal.pone.0099596 (2014).

Rahman, M. A. et al., "S-nitrosylation at cysteine 498 of c-Src tyrosine kinase regulates nitric oxide-mediated cell invasion", The Journal of biological chemistry 285, 3806-3814, doi:10.1074/jbc.M109.059782 (2010).

Bao, Y., Chen, Y., Ledderose, C., Li, L. & Junger, W. G., "Pannexin 1 channels link chemoattractant receptor signaling to local excitation and global inhibition responses at the front and back of polarized neutrophils", The Journal of biological chemistry 288, 22650-22657, doi:10.1074/jbc.M113.476283 (2013).

Adamson et al., "Pannexin1 is required for full activation of insulin-stimulated glucose uptake in adipocytes," Molecular Metabolism, vol. 4, pp. 610-618 (2015).

Akhand, et al., "Nitric oxide controls src kinase activity through a sulfhydryl group modification-mediated Tyr-527-independent and Tyr-416 linked mechanism," The Journal of biological chemistry, vol. 274, p. 25821-25826 (1999).

Ayata, et al., "Purinergic P2Y(2) receptors promote neutrophil infiltration and hepatocyte death in mice with acute liver injury," Gastroenterology, vol. 143, pp. 1620-1629 (2012).

Baker, et al., "P2Y2 nucleotide receptor activation up-regulates vascular cell adhesion molecule-1 [corrected] expression and enhances lymphocyte adherence to a human submandibular gland cell line," Mol Immunol, vol. 45, pp. 65-75 (2008).

Bouma, et al., "Adenosine inhibits cytokine release and expression of adhesion molecules by activated human endothelial cells," The American journal of physiology, vol. 270, pp. 522-529 (1996) (Abstract).

Chello, et al., "Nitric oxide modulation of neutrophil-endothelium interaction: difference between arterial and venous coronary bypass grafts," Journal of the American College of Cardiology, vol. 31, pp. 823-826 (1998).

Chen, et al., "ATP release guides neutrophil chemotaxis via P2Y2 and A3 receptors," Science vol. 314, pp. 1792-1795 (2006) (Abstract).

Clark, et al., "Neutrophil transmigration: modulation by pentoxifylline and nitric oxide," Biochemical Society transactions, vol. 25, p. 454 (1997).

Dal Secco, et al., Neutrophil migration in inflammation: nitric oxide inhibits rolling, adhesion and induces apoptosis. Nitric oxide: biology and chemistry | official journal of the Nitric Oxide Society, vol. 9, pp. 153-164 (2003)(Abstract).

Grassi, F., "Purinergic control of neutrophil activation," J Mol Cell Biol, vol. 2, pp. 176-177 (2010).

Gulbransen, et al., "Activation of neuronal P2X7 receptor-pannexin-1 mediates death of enteric neurons during colitis," Nature medicine, vol. 18, pp. 600-604, (2012).

Hyman, et al., "Self-regulation of inflammatory cell trafficking in mice by the leukocyte surface apyrase CD39," The Journal of clinical investigation, vol. 119, pp. 1136-1149 (2009).

International Search Report corresponding to International Patent Application No. PCT/US 16/44683 dated Dec. 19, 2016.

International Preliminary Report on Patentability corresponding to PCT/US2016/044683 dated Jan. 30, 2018.

Kmiecik, et al., Activation and suppression of pp60c-src transforming ability by mutation of its primary sites of tyrosine phosphorylation. Cell vol. 49, pp. 65-73 (1987) (Abstract).

Koszalka, et al., "Targeted disruption of cd73/ecto-5'-nucleotidase alters thromboregulation and augments vascular inflammatory response," Circulation research, vol. 95, pp. 814-821 (2004).

Kubes et al., "Nitric oxide: an endogenous modulator of leukocyte adhesion," Proc Natl Acad Sci USA vol. 88, pp. 4651-4655 (1991).

Kubes, et al., "Nitric oxide modulates microvascular Permeability," Am. J. Physiol, vol. 262, pp. 611-615 (1992).

Laird, D. W., "Life cycle of connexins in health and disease," The Biochemical journal, vol. 394, pp. 527-543 (2006).

Ley, et al., "Getting to the site of inflammation: the leukocyte adhesion cascade updated," Nature reviews: Immunology, vol. 7, pp. 678-689 (2007).

Li, et al., "Acute tumor necrosis factor alpha signaling via NADPH oxidase in microvascular endothelial cells: role of p47phox phosphorylation and binding to TRAF4," Mol Cell Biol, vol. 25, pp. 2320-2330 (2005).

Marchesi, M. A. et al., "Electron micrographic observations on the emigration of leucocytes," Quarterly journal of experimental physiology and cognate medical sciences, vol. 45, pp. 343-348 (1960).

Marchesi, V. T., "The site of leucocyte emigration during inflammation," Quarterly journal of experimental physiology and cognate medical sciences, vol. 46, pp. 115-118 (1961).

Marques-Fernandez, et al., "TNF alpha induces survival through the FLIP-L dependent activation of the MAPK/ERK pathway," Cell Death Dis, vol. 4, p. 493 (2013).

(56) References Cited

OTHER PUBLICATIONS

McDonald, et al., "Intravascular danger signals guide neutrophils to sites of sterile inflammation," Science, vol. 330, pp. 362-366 (2010) (Abstract).
Okutani, et al., "Src protein tyrosine kinase family and acute inflammatory responses," American journal of physiology: Lung cellular and molecular physiology, vol. 291, pp. I29-141 (2006).
Pelegrin, et al., "Pannexin-1 mediates large pore formation and interleukin-1 beta release by the ATP-gated P2X7 receptor," The EMBO journal, vol. 25, pp. 5071-5082 (2006).
Penuela, et al., "Pannexin 1 and pannexin 3 are glycoproteins that exhibit many distinct characteristics from the connexin family of gap junction proteins," Journal of cell science, vol. 120, pp. 3772-3783 (2007).
Poon, et al., "Unexpected link between an antibiotic, pannexin channels and apoptosis," Nature vol. 507, pp. 329-334 (2014).
Qiu, et al., "A permeant regulating its permeation pore: inhibition of pannexin 1 channels by ATP," Am J Physiol Cell Physiol, vol. 296, pp. 250-255 (2009).
Ralevic, et al., "Receptors for purines and pyrimidines," Pharmacological reviews, vol. 50, pp. 413-492 (1998).
Reutershan, et al., "Adenosine and inflammation: CD39 and CD73 are critical mediators in LPS-induced PMN trafficking into the lungs," FASEB journal: official publication of the Federation of American Societies for Experimental Biology, vol. 23, pp. 473-482 (2009).
Riegel et al., "Selective induction of endothelial P2Y6 nucleotide receptor promotes vascular inflammation," Blood 117, 2548-2555 (2011).
Riteau, et al., "Extracellular ATP is a danger signal activating P2X7 receptor in lung inflammation and fibrosis," American Journal of Respiratory and Critical Care Medicine, vol. 182, pp. 774-783 (2010).
Smedlund, et al., "Involvement of native TRPC3 proteins in ATP dependent expression of VCAM-1 and monocyte adherence in coronary artery endothelial cells," Arterioscler Thromb Vase Biol, vol. 28, pp. 2049-2055 (2008).
Taruno, et al., "CALHM1 ion channel mediates purinergic neurotransmission of sweet, bitter and umami tastes," Nature, vol. 495, pp. 223-226 (2013).
Vanderstocken, et al., "P2Y2 receptor regulates VCAM-1 membrane and soluble forms and eosinophil accumulation during lung inflammation," J Immunol, vol. 185, pp. 3702-3707 (2010).
VanUffelen, et al., "Modulation of neutrophil migration by exogenous gaseous nitric oxide," Journal of leukocyte biology, vol. 60, pp. 94-100 (1996).
Woehrle, et al., "Pannexin-1 hemichannel-mediated ATP release together with P2X1 and P2X4 receptors regulate T-cell activation at the immune synapse," Blood, vol. 116, pp. 3475-3484 (2010).
Written Opinion corresponding to International application No. PCT/US 16/44683 dated Dec. 19, 2016.
International Search Report corresponding to International Patent Application No. PCT/US2016/017830 dated May 2, 2016.
Notice of Allowance and Interview Summary corresponding to U.S. Appl. No. 15/549,232 dated Mar. 6, 2019.
Notice of Allowance and Interview Summary corresponding to U.S. Appl. No. 16/382,269 dated Oct. 20, 2021.
Notification Concerning Transmittal of International Preliminary Report on Patentability (Chapter I) corresponding to International Patent Application No. PCT/US2016/017830 dated Aug. 24, 2017.
Office Action (Restriction Requirement) corresponding to U.S. Appl. No. 15/549,232 dated Sep. 13, 2018.
Office Action (Restriction Requirement) corresponding to U.S. Appl. No. 16/382,269 dated Jul. 28, 2020.
Office Action corresponding to U.S. Appl. No. 15/549,232 dated Jan. 8, 2019.
Office Action corresponding to U.S. Appl. No. 16/382,269 dated Feb. 10, 2021.
Office Action corresponding to U.S. Appl. No. 16/382,269 dated May 27, 2021.
Written Opinion corresponding to International Patent Application No. PCT/US2016/017830 dated May 2, 2016.
Adamson et al., "The role of pannexin1 in the induction and resolution of inflammation," Author Manuscript, pp. 1-16, available in PMC 2015: Published in final edited form as FEBS Lett vol. 588, No. 8, pp. 1416-1422 (2014).
Akers et al., "Peptides and proteins as parenteral solutions," Pharmaceutical Formulation Development of Peptides and Proteins, Frokjaer and Hovgaard, eds; 2nd Ed., Chptr 8, pp. 145-177 (2012).
Altschul et al. "Gapped BLAST and PSI-BLAST: a new generation of protein database search programs," Nucleic Acids Res., vol. 25, No. 17, pp. 3389-3402 (1997).
Altschul, et al. "Basic Local Alignment Search Tool," J. Mol. Biol., vol. 215, pp. 403-410 (1990).
Artamonov et al., "Agonist-induced Ca2+ sensitization in smooth muscle: redundancy of Rho guanine nucleotide exchange factors (RhoGEFs) and response kinetics, a caged compound study," The Journal of biological chemistry, vol. 288, No. 47, p. 34030-34040 (2013).
Azzarito et al. "Inhibition of alpha-helix-mediated protein-protein interactions using designed molecules," Nat Chem, vol. 5, pp. 161-173 (2013).
Billaud et al. "A molecular signature in the pannexin1 intracellular loop confers channel activation by the alpha 1 adrenoreceptor in smooth muscle cells," Sci Signal (published online Feb. 17, 2015), vol. 8, No. 364, p. ra17. Especially p. 5, Table 3; p. 5, col. 2, para. 2; p. 8, col. 1, para. 3 (2015a).
Billaud et al. "Characterization of the thoracodorsal artery: morphology and reactivity," Microcirculation, vol. 19, 360-372 (2012a).
Billaud et al. "Regulation of cellular communication by signaling microdomains in the blood vessel wall," Pharmacological reviews, vol. 66, pp. 513-569 (2014).
Billaud et al. Supplementary Materials for "A molecular signature in the pannexin1 intracellular loop confers channel activation by the alpha 1 adrenoreceptor in smooth muscle cells," Science Signaling, pp. 1-5 (2015b).
Billaud et al., "Pannexin 1 in the regulation of vascular tone," Trends Cardiovasc Med., Apr. 2012, vol. 22, No. 3, pp. 68-72, Especially abstract; p. 70, col. 1, para. 3 (2012b).
Boassa et al. "Pannexin1 Channels Contain a Glycosylation Site That Targets the Hexamer to the Plasma Membrane," J. Biol. Chem., vol. 282, No. 43, p. 31733-31743 (2007).
Bodanszky and Bodanszky in The Practice of Peptide Synthesis, 1984, Springer-Verlag, New York.
Bond et al., "The pannexins: past and present," Front Physiol, vol. 5, No. 58, pp. 1-24 (2014).
Boonen et al., "G-proteins are involved in contractile responses of isolated mesenteric resistance arteries to agonists," Naunyn-Schmiedeberg's Arch Pharmacol vol. 342, pp. 462-468 (1990).
Budzyn et al., "Segmental Differences in the Roles of Rho-Kinase and Protein Kinase C in Mediating Vasoconstriction," J Pharmacal Exp Ther, vol. 317, No. 2, pp. 791-796 (2006).
Burnstock et al., "Purinergic Signaling and Blood Vessels in Health and Disease," Pharmacol Rev vol. 66, pp. 102-192 (2014).
Burnstock, "Dual control of vascular tone and remodelling by ATP released from nerves and endothelial cells," Pharmacol Rep., vol. 60, pp. 12-20 (2008).
Cechova et al. "Loss of collectrin, an angiotensin-converting enzyme 2 homolog, uncouples endothelial nitric oxide synthase and causes hypertension and vascular dysfunction," Circulation, vol. 128, pp. 1770-1780 (2013).
Cheng et al. "Porcine bladder urothelial, myofibroblast, and detrusor muscle cells: characterization and ATP release," Front. Pharmacol., vol. 2, Art. 27, pp. 1-9 (2011).
Chou et al. "Empirical Predictions of Protein Conformation," Ann. Rev. Biochem., vol. 47, pp. 251-276 (1978).
Chou et al., "Prediction of Protein Conformation," Biochemistry, vol. 13, No. 2, pp. 222-245 (1974).
Chou et al., "Prediction of β-turns," Biophys. J., vol. 26, pp. 367-384 (1979).

(56) References Cited

OTHER PUBLICATIONS

Coker et al. "Effects of mefloquine on cardiac contractility and electrical activity in vivo, in isolated cardiac preparations, and in single ventricular myocytes," British journal of pharmacology, vol. 129, pp. 323-330 (2000).
Deutscher et al. ed., 1990, Guide to Protein Purification, Harcourt Brace Jovanovich, San Diego.
Diezmos et al. "Expression and localization of pannexin-1 hemichannels in human colon in health and disease," Neurogastroenterology and motility: the official journal of the European Gastrointestinal Motility Society, 25, e395-405 (2013).
Dinenno et al. "Post-junctional alpha-adrenoceptors and basal limb vascular tone in healthy men," The Journal of physiology, vol. 540, pp. 1103-1110 (2002).
Edwards et al. "Helix-mediated protein-protein interactions as targets for intervention using foldamers," Amino Acids, vol. 41, pp. 743-754 (2011).
Gait, 1985, Oligonucleotide Synthesis: A Practical Approach (IRL Press, Oxford, England.
Genaro, ed., 1985, Remington's Pharmaceutical Sciences, Mack Publishing Co., Easton, PA.
Gerhardt et al., eds., 1994, Methods for General and Molecular Bacteriology, American Society for Microbiology, Washington, DC, p. 574.
Giepmans et al. "Gap junctions and connexin-interacting proteins," Cardiovasc Res, vol. 62, pp. 233-245 (2004).
Godecke et al., "Thrombin-induced ATP release from human umbilical vein endothelial cells," American Journal of Physiology—Cell Physiology, vol. 302, pp. C915-C923 (2012).
Gross and Mienhofer, eds., The Peptides, vol. 3, pp. 3-88 (Academic Press, New York, 1981).
Guimaraes et al. "Vascular adrenoceptors: an update," Pharmacological reviews, vol. 53, No. 2, pp. 319-356 (2001).
Harlow et al. Antibodies, A Laboratory Manual, Cold Spring Harbor Publications, New York (1988).
Heesen et al., "Effects of cyclic AMP-affectIng agents on contractile reactivity of isolated mesenteric and renal resistance arteries of the rat," Br J Pharmacol, vol. 101, pp. 859-864 (1990).
Hill et al., "The involvement of intracellular Ca(2+) in 5-HT(1B/1D) receptor-mediated contraction of the rabbit isolated renal artery," Br J Pharmacol., vol. 130, pp. 835-842 (2000).
Howl et al., "The many futures for cell-penetrating peptides: how soon is now?" Biochem Soc Trans, vol. 35, part 4, pp. 767-769 (2007).
Iglesias et al. "Mefloquine blockade of Pannexin1 currents: resolution of a conflict," Cell communication & adhesion, vol. 16, pp. 131-137 (2010).
Iglesias et al., "P2X7 receptor-Pannexin1 complex: pharmacology and signaling," American Journal of Physiology—Cell Physiology, vol. 295, p. C752-C760 (2008).
Isakson et al. "Pannexin-1 as a potentiator of ligand-gated receptor signaling," Channels (Austin) vol. 8, Iss. 2, pp. 118-123 (2014).
Jackson et al., "Smooth muscle alpha1 D-adrenoceptors mediate phenylephrine-induced vasoconstriction and increases in endothelial cell Ca2+ in hamster cremaster arterioles," Br J Pharmacol, vol. 155, pp. 514-524 (2008).
Karlin et al. "Applications and statistics for multiple high-scoring segments in molecular sequences," Proc. Natl. Acad. Sci. USA, vol. 90, pp. 5873-5877 (1993).
Karlin et al. "Methods for assessing the statistical significance of molecular sequence features by using general scoring schemes," Proc. Natl. Acad. Sci. USA, vol. 87, pp. 2264-2268 (1990).
Karsten et al. "Involvement of cyclic nucleotides in renal artery smooth muscle relaxation," Urol Res 30, 367-373 (2003).
Katsuragi et al. "ATP release by angiotensin II from segments and cultured smooth muscle cells of guinea-pig *Taenia coli*," Naunyn Schmiedeberg's Arch Pharmacol 354, 796-799 (1996).
Kay et al. "The importance of being proline: the interaction of proline-rich motifs in signaling proteins with their cognate domains," The FASEB journal: official publication of the Federation of American Societies for Experimental Biology, vol. 14, pp. 231-241 (2000).
Kitazawa et al., "Size-dependent heterogeneity of contractile Ca2+ sensitization in rat arterial smooth muscle," The Journal of physiology, vol. 590, pp. 5401-5423 (2012).
Kyte et al. "A Simple Method for Displaying the Hydropathic Character of a Protein," J. Mol. Biol., vol. 157, pp. 105-132 (1982).
Li et al., "Characterization of Novel Pannexin 1 Isoforms from Rat Pituitary Cells and their Association with ATP-gated P2X Channels," Author Manuscript, 20 pages, published in final edited form as: Gen Comp Endocrinol., vol. 174, pp. 202-210 (2011).
Lohman et al. "Pannexin 1 channels regulate leukocyte emigration through the venous endothelium during acute inflammation," Nature Communications, 6:7965, pp. 1-12 (2015a).
Lohman et al. Supplementary Figures, and Figures for "Pannexin 1 channels regulate leukocyte emigration through the venous endothelium during acute inflammation," pp. 1-41 (2015b).
Loirand et al., "Small G proteins in the cardiovascular system: physiological and pathological aspects," Physiol Rev, vol. 93, pp. 1659-1720 (2013).
Ma et al., "Pharmacological characterization of pannexin-1 currents expressed in mammalian cells," J Pharmacal Exp Ther, vol. 328, No. 2, pp. 409-418 (2009).
Momotani et al., "p63RhoGEF couples Galpha(q/11)-mediated signaling to Ca2+ sensitization of vascular smooth muscle contractility," Circulation research, vol. 109, Iss. 9, pp. 993-1002 (2011).
Moore et al. "Regional heterogeneity of alpha-adrenoreceptor subtypes in arteriolar networks of mouse skeletal muscle," The Journal of physiology, vol. 588, pp. 4261-4274 (2010).
Ohyanagi et al. "Differential activation of alpha1- and alpha2-adrenoceptors on microvascular smooth muscle during sympathetic nerve stimulation," Circulation research, vol. 68, No. 1, pp. 232-244 (1991).
Panchin et al., "A ubiquitous family of putative gap junction molecules," Curr Biol., vol. 10, No. 13, pp. R473-R474 (2000).
Pierre et al., "Endothelin receptor subtypes and their functional relevance in human small coronary arteries," Br J Pharmacol., vol. 124, pp. 499-506 (1998).
Pinheiro et al., "Bradykinin-induced Ca2+ signaling in human subcutaneous fibroblasts involves ATP release via hemichannels leading to P2Y12 receptors activation," Cell Common Signal., vol. 11, No. 70, pp. 1-17 (2013a).
Pinheiro et al., "Histamine induces ATP release from human subcutaneous fibroblasts, via pannexin-1 hemichannels, leading to Ca2+ mobilization and cell proliferation," The Journal of biological chemistry, vol. 288, No. 38, p. 27571-27583 (2013b).
Riquelme et al. "The ATP required for potentiation of skeletal muscle contraction is released via pannexin hemichannels," Neuropharmacology, 75, 594-603 (2013).
Rizzoni et al., "The vasoconstriction induced by endothelin-1 is mediated only by ET(A) receptors in mesenteric small resistance arteries of spontaneously hypertensive rats and Wistar Kyoto rats," J Hypertens, vol. 15, No. 12, pp. 1653-1657 (1997).
Robertson et al. "Effects of Rho-kinase and Src protein tyrosine kinase inhibition on agonist-induced vasoconstriction of arteries and veins of the equine laminar dermis," Am J Vet Res 68, 886-894 (2007).
Sandilos et al.. "Physiological mechanisms for the modulation of pannexin 1 channel activity," The Journal of physiology, vol. 590, pp. 6257-6266 (2012b).
Seminario-Vidal et al., "Rho signaling regulates pannexin 1-mediated ATP release from airway epithelia," The Journal of biological chemistry, vol. 286, No. 30, p. 26277-26286 (2011).
Seminario-Vidal et al., "Thrombin promotes release of ATP from lung epithelial cells through coordinated activation of rho- and Ca2+-dependent signaling pathways," The Journal of biological chemistry, vol. 284, No. 31, p. 20638-20648 (2009).
Sosinsky et al., "Pannexin channels are not gap junction hemichannels," Channels (Austin) vol. 5, No. 3, pp. 193-197 (2011).
Spagnol et al., "Structural order in Pannexin 1 cytoplasmic domains," Channels, vol. 8, No. 2. pp. 157-166 (2014).

(56) References Cited

OTHER PUBLICATIONS

Sridharan et al., "Pannexin 1 is the conduit for low oxygen tension-induced ATP release from human erythrocytes," Am J Physiol Heart Circ Physiol, vol. 299, pp. H1146-1152 (2010).

Stewart et al. in Solid Phase Peptide Synthesis, 2nd Edition, 1984, Pierce Chemical Company, Rockford, Illinois.

Tanoue et al., "The alpha(1D)-adrenergic receptor directly regulates arterial blood pressure via vasoconstriction," J Clin Invest, vol. 109, pp. 765-775 (2002).

Timoteo et al. "ATP released via pannexin-1 hemichannels mediates bladder overactivity triggered by urothelial P2Y6 receptors," Biochem Pharmacol 87, 371-379 (2014).

Tsai et al., "Rho-kinase-medSated regulation of receptor-agonist-stimulated smooth muscle contraction," Pfluqers Arch vol. 453, pp. 223-232 (2006).

UniProtKB Accession No. E0X643, 1 page, Oct. 1, 2014 [online], [Retrieved on Apr. 22, 2016], Retrieved from the internet <URL: http://www.uniprot.org/uniprot/E0X643.txt?version:=13> Entire document.

UniProtKB Accession No. Q5VGQ7, 1 page, Oct. 29, 2014 [online], [Retrieved on Apr. 22, 2016], Retrieved from the internet <URL: http://www.uniprot.org/uniprot/Q5VGQ7.txt?version=44> Entire document.

UniProtKB Accession No. Q96RD7, accessed Feb. 6, 2021 at URL: uniport.org/uniport/ Q96RD7, pp. 1-11 (Year: 2021).

Vettel et al. "A novel player in cellular hypertrophy: Gibetagamma/PI3K-dependent activation of the RacGEF TIAM-1 is required for alpha(1)-adrenoceptor induced hypertrophy in neonatal rat cardiomyocytes," J Mol Cell Cardiol 53, 165-175 (2012).

Vives et al., "A truncated HIV-1 Tat protein basic domain rapidly translocates through the plasma membrane and accumulates in the cell nucleus," J Biol Chem, vol. 272, No. 25, p. 16010-16017 (1997).

Wang et al. "Modulation of membrane channel currents by gap junction protein mimetic peptides: size matters," Am J Physiol Cell Physiol, vol. 293, No. 3, pp. C1112-C1119 (2007). Especially abstract; p. C1113, col. 1, para. 7 (2007).

Wang et al. "SCAM analysis of Panx1 suggests a peculiar pore structure," The Journal of general physiology, vol. 136, No. 5, pp. 515-527 (2010).

Watts et al., "5-hydroxtryptamine receptors in systemic hypertension: an arterial focus," Cardiovasc Ther, vol. 29, pp. 54-67 (2011).

Watts, "Serotonin-induced contraction in mesenteric resistance arteries: signaling and changes in deoxycorticosterone acetate-salt hypertension," Hypertension, vol. 39, pp. 825-829 (2002).

Weilinger et al., "Ionotropic receptors and ion channels in ischemic neuronal death and dysfunction," Acta Pharmacol Sin, vol. 34, pp. 39-48 (2013).

Westcott et al., "Ageing alters perivascular nerve function of mouse mesenteric arteries in vivo," The Journal of physiology, vol. 591, pp. 1251-1263 (2013).

Wirth et al. "G12-G13-LARG-mediated signaling in vascular smooth muscle is required for salt-induced hypertension," Nat Med, vol. 14, No. 1, pp. 64-68 (2008).

Xiong et al. "Probenecid Protects Against Transient Focal Cerebral Ischemic Injury by Inhibiting HMGB1 Release and Attenuating AQP4 Expression in Mice," Neurochem Res, vol. 39, pp. 216-224 (2014).

Yen et al., "Gap junctional proteins of animals: the innexin/pannexin superfamily," Author manuscript, pp. 1-14, available in PMC Dec. 1, 2008; Published in final edited form as: Prog Biophys Mol Biol. vol. 94, pp. 5-14 (2007).

Zhang et al., "P2Y2 receptor activation opens pannexin-1 channels in rat carotid body type II cells: potential role in amplifying the neurotransmitter ATP," The Journal of physiology, vol. 590, pp. 4335-4350 (2012).

Notice of Allowance and Interview Summary corresponding to U.S. Appl. No. 16/382,269 dated Oct. 20, 2020.

Stokes, et al., "Role of platelets in hypercholesterolemia-induced leukocyte recruitment and arteriolar dysfunction," Microcirculation, vol. 13, pp. 377-388 (2006).

Notice of Allowance corresponding to U.S. Appl. No. 16/382,269 dated Feb. 24, 2022.

* cited by examiner

FIG.1 A-B
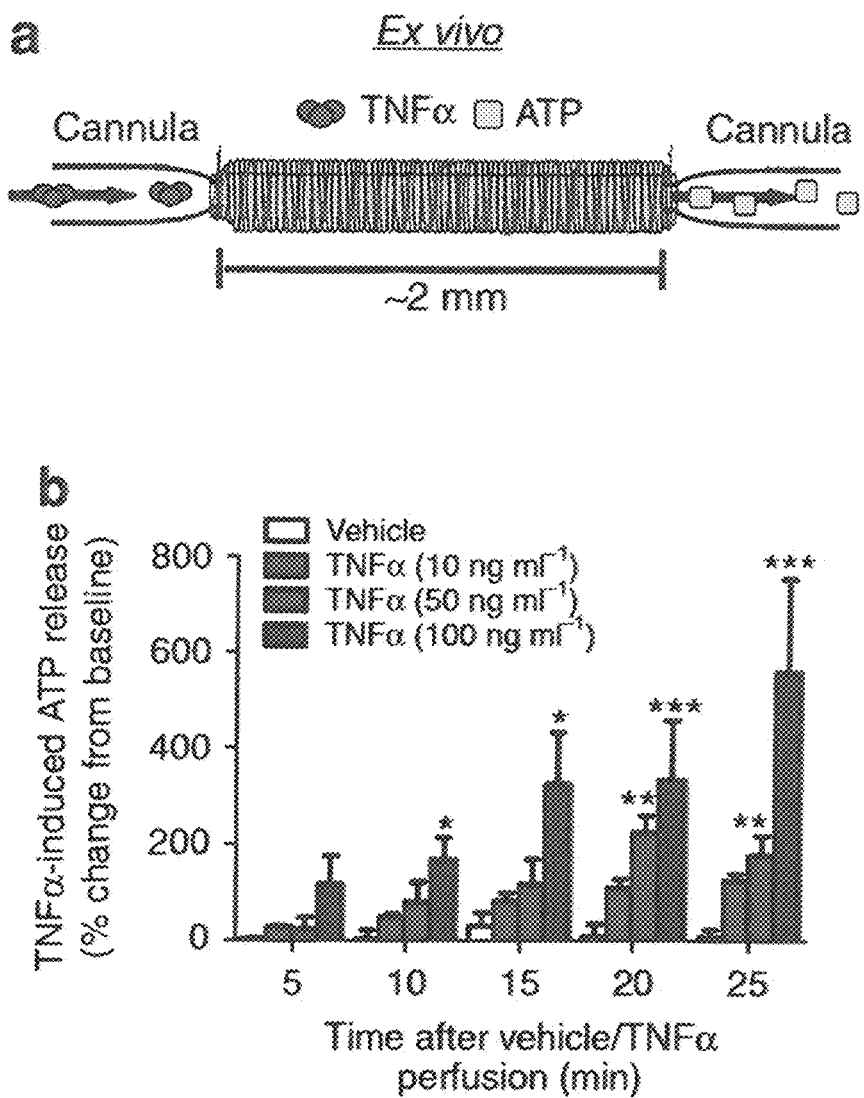

FIG.1 C-D
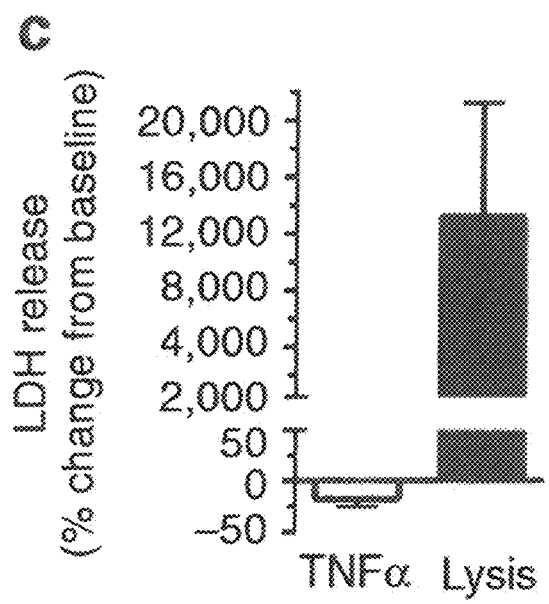
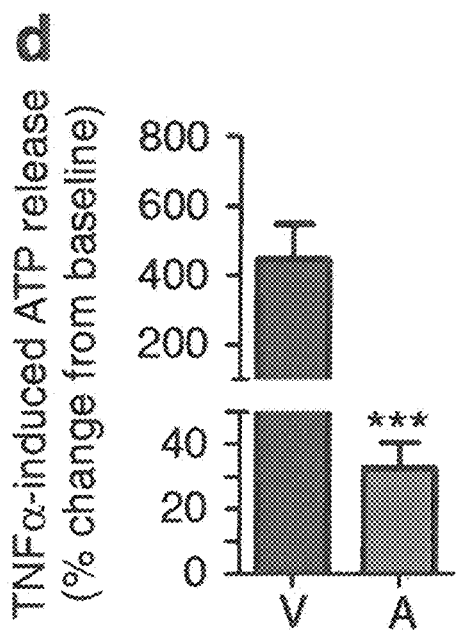

FIG.1 E-F
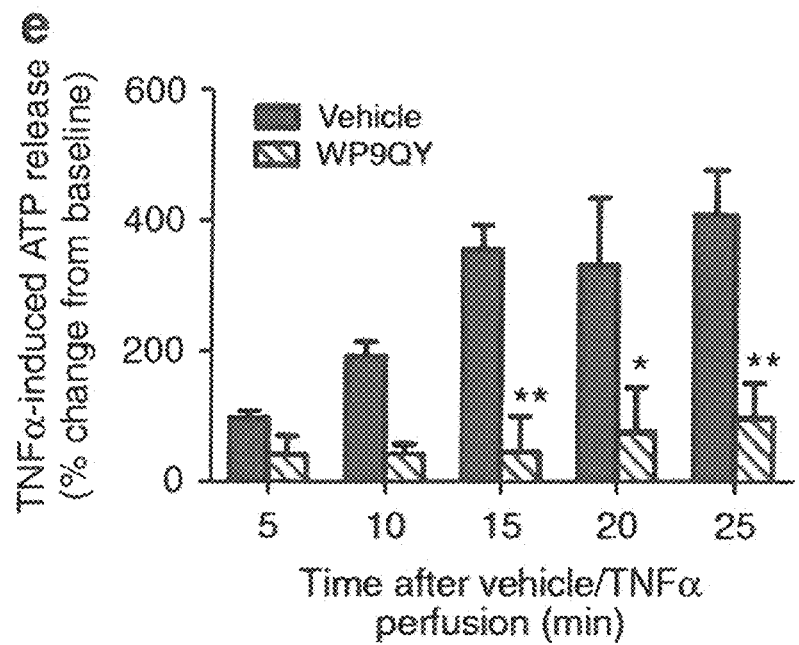
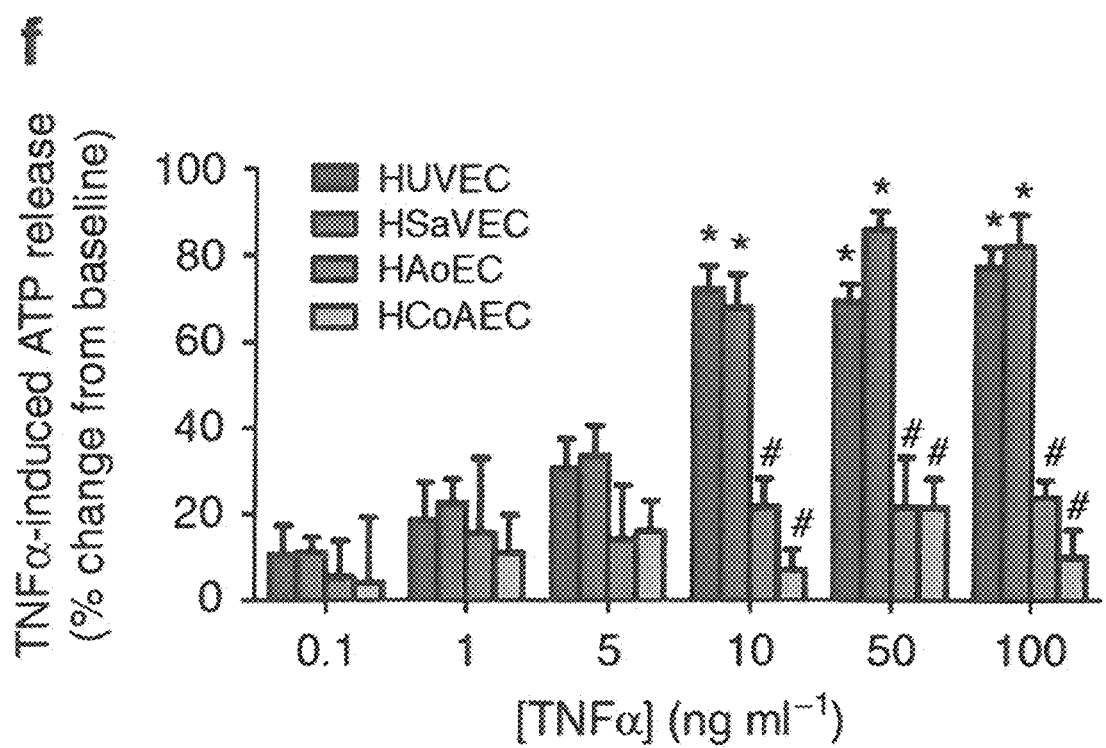

FIG.1 G-H
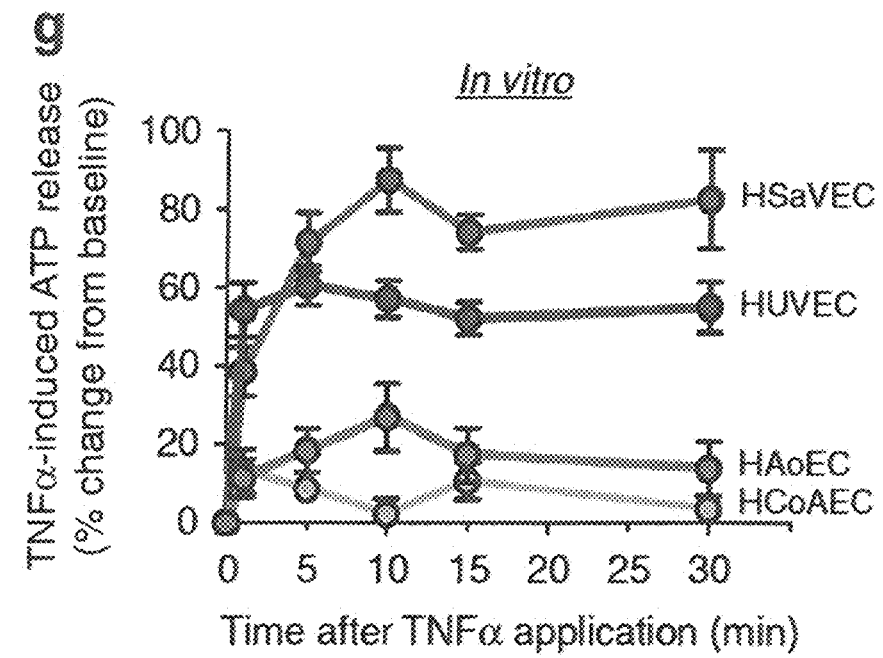
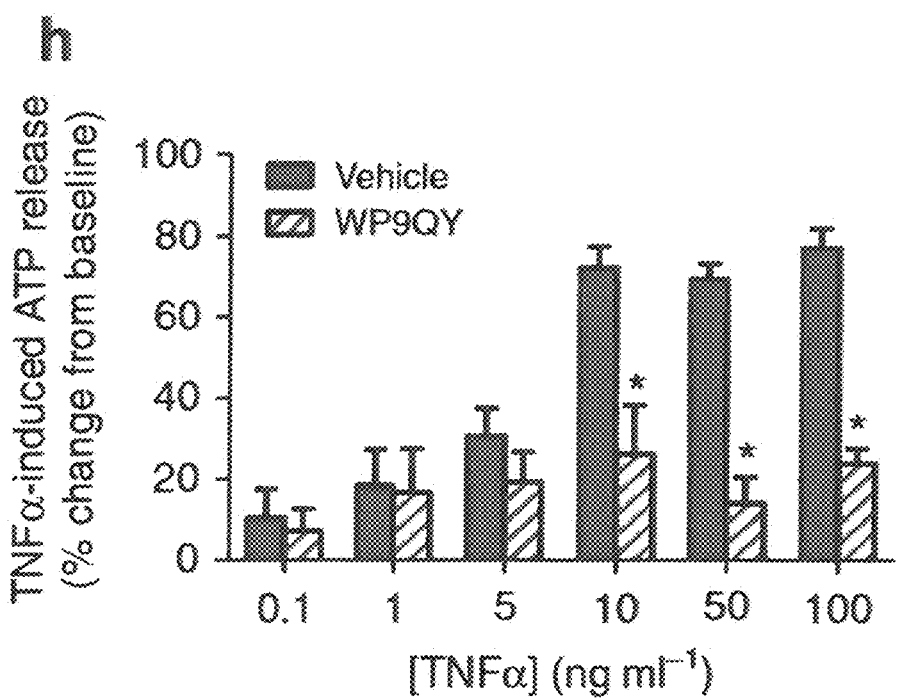

FIG.2 A-B
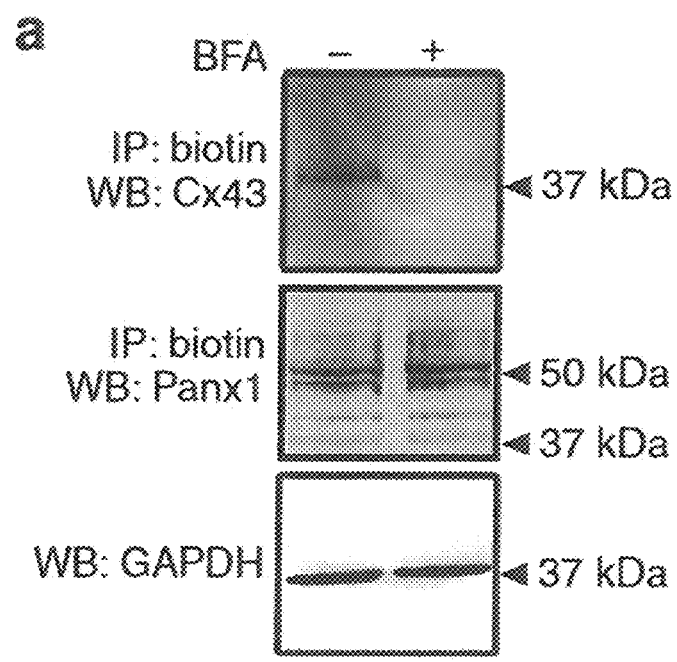
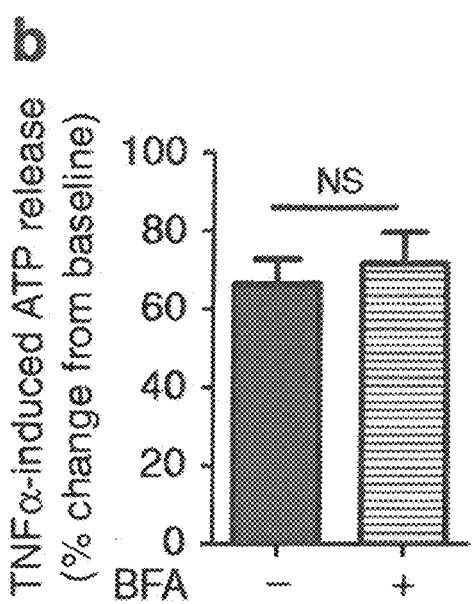

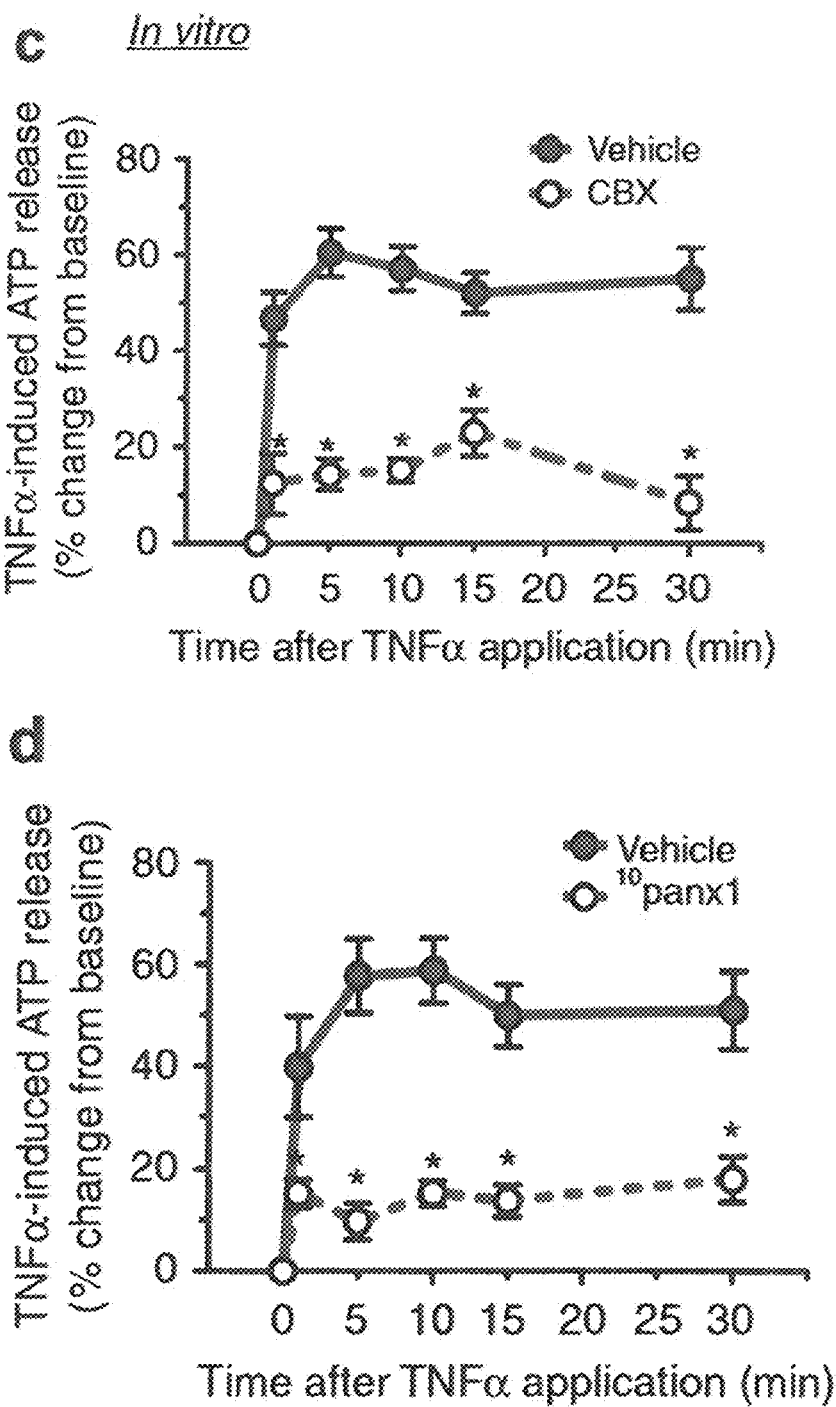

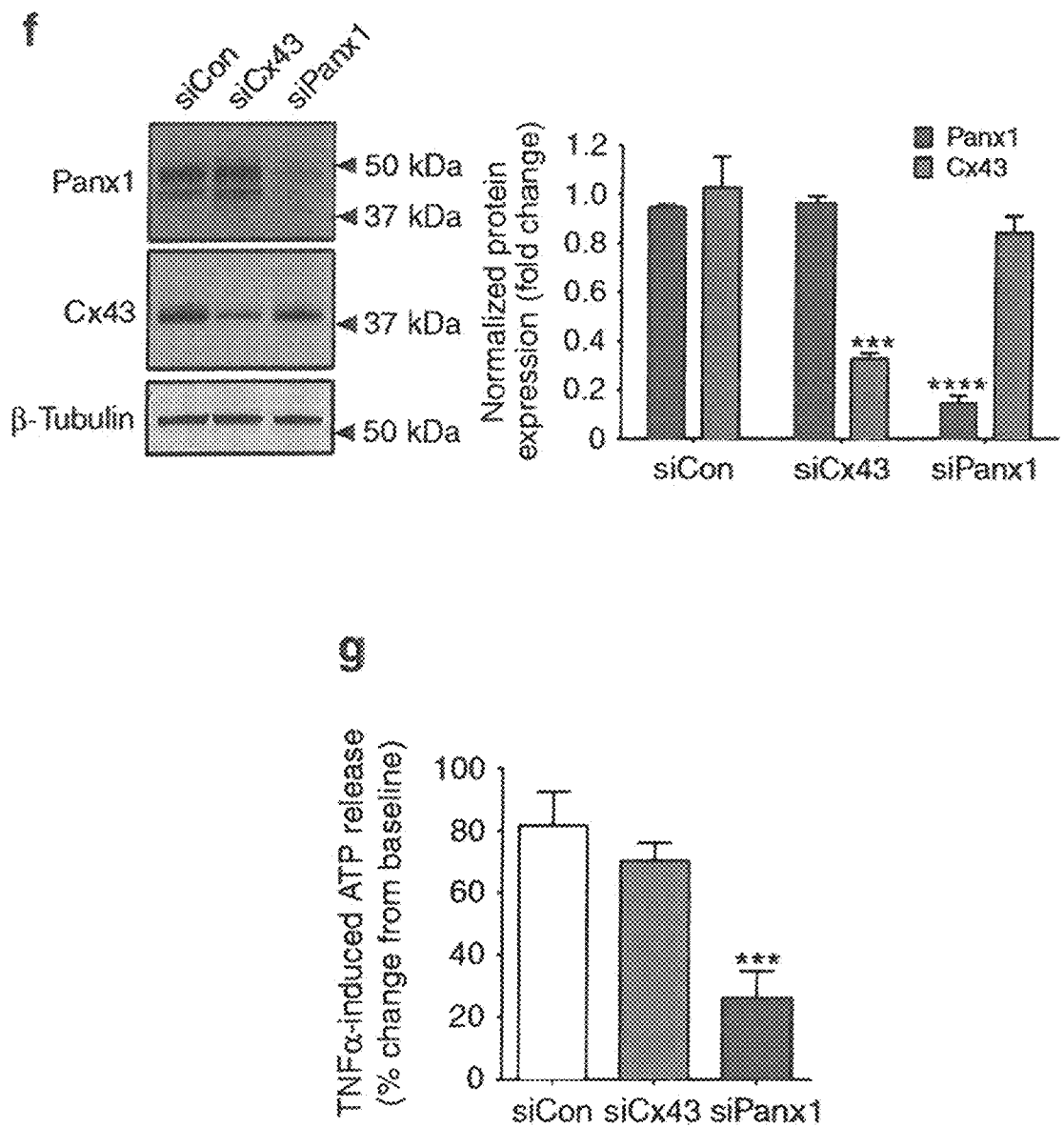
FIG.2 F-G

FIG2. H-I
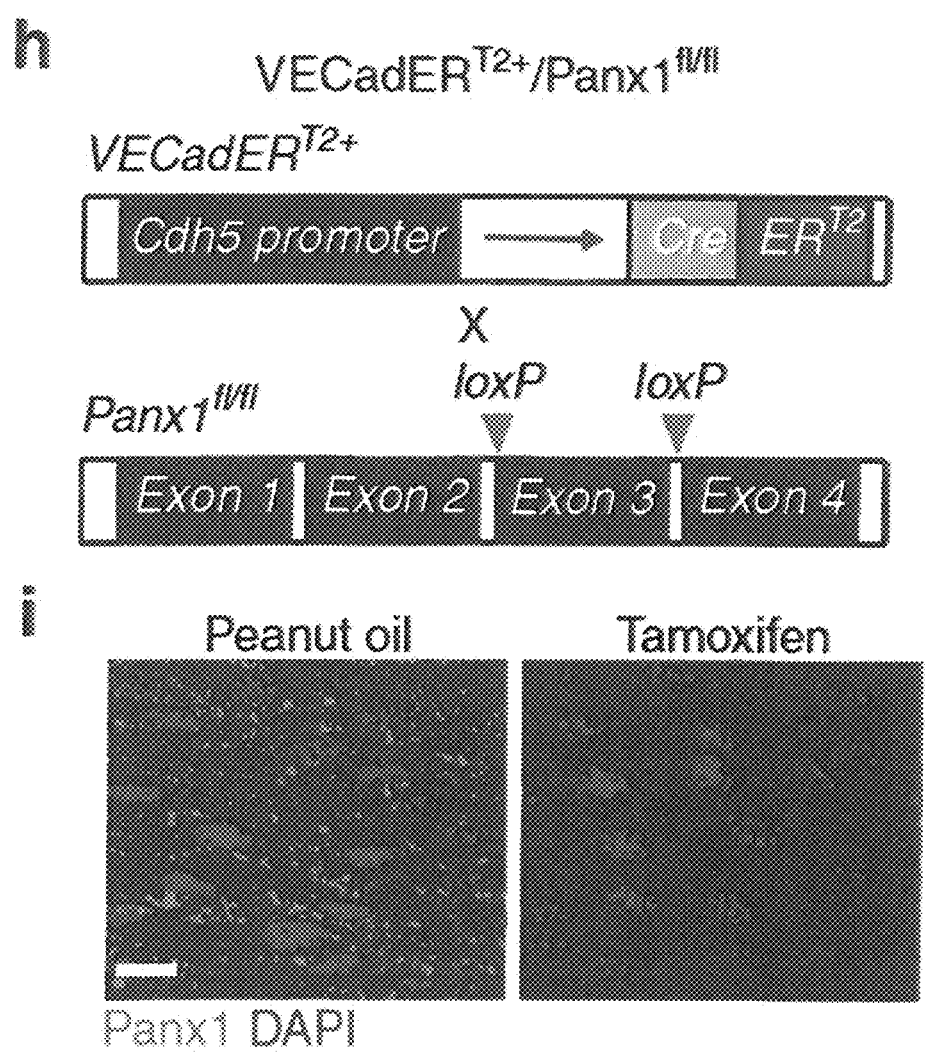

FIG.3 A-B
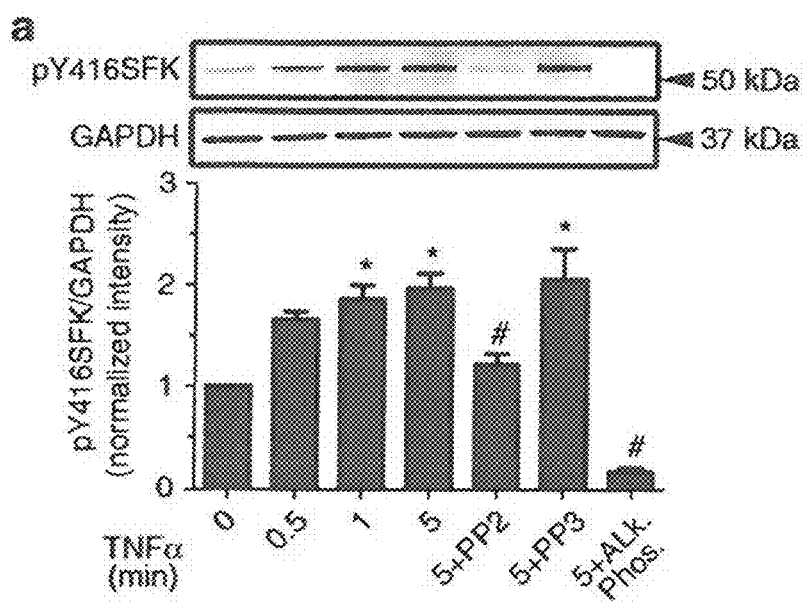
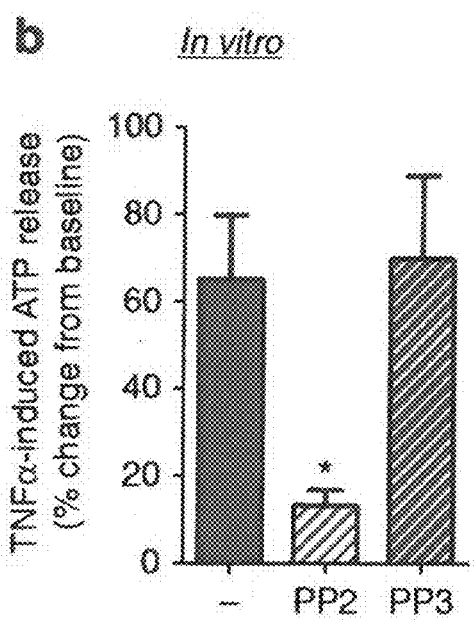

FIG. 3 C-D
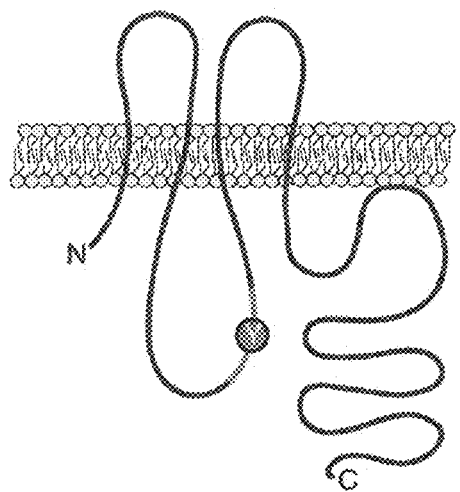
pY198Panx1: 192-CPIVEQY(p)LKTKKNS-205
Panx1-IL: 192-CPIVEQYLKTKKNS-205
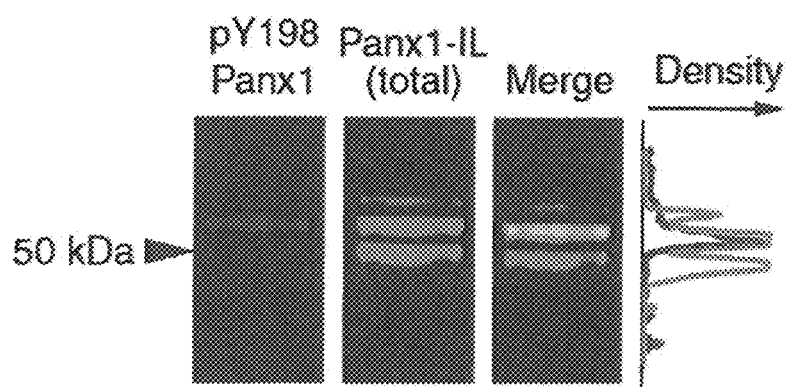

FIG.3 E-F
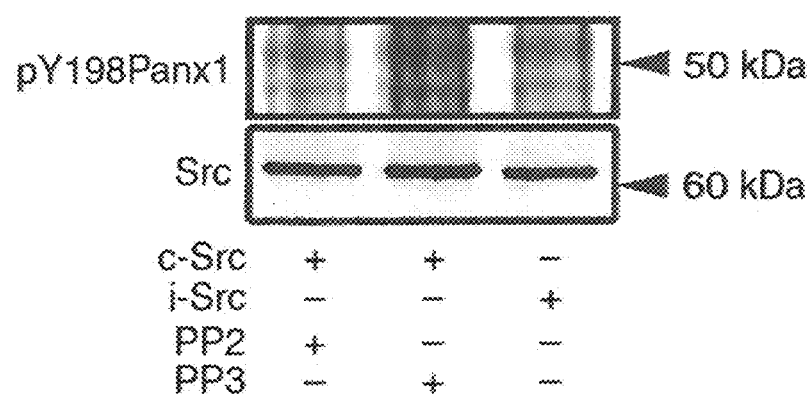
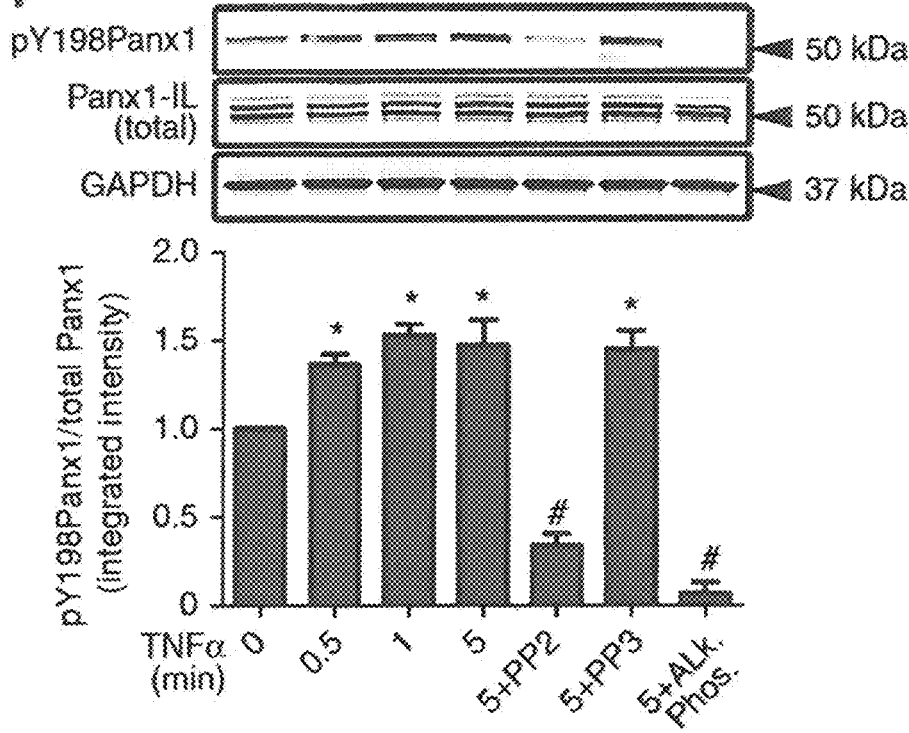

FIG.3 H-I
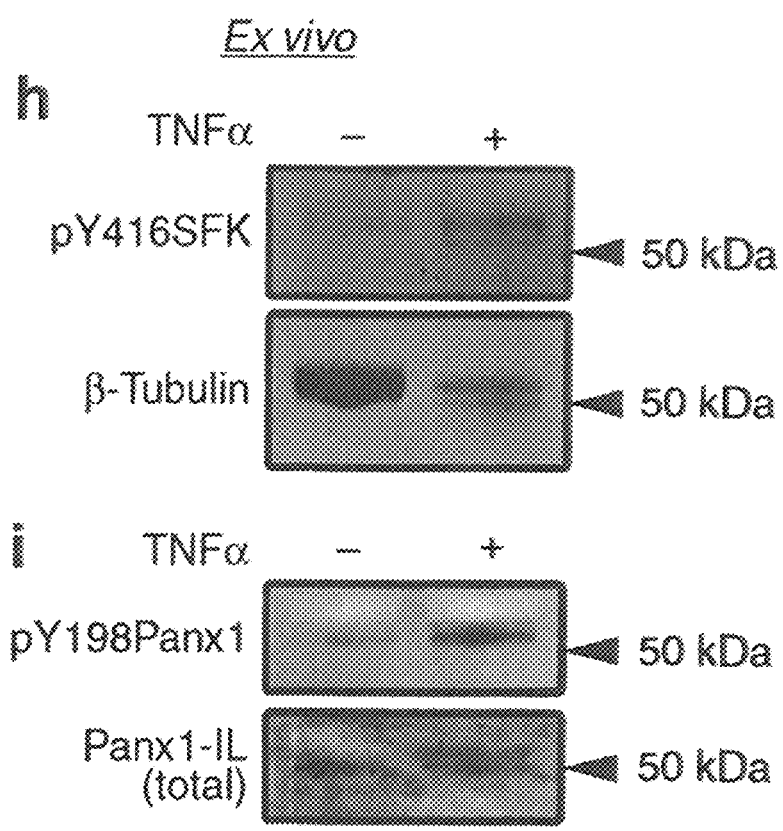

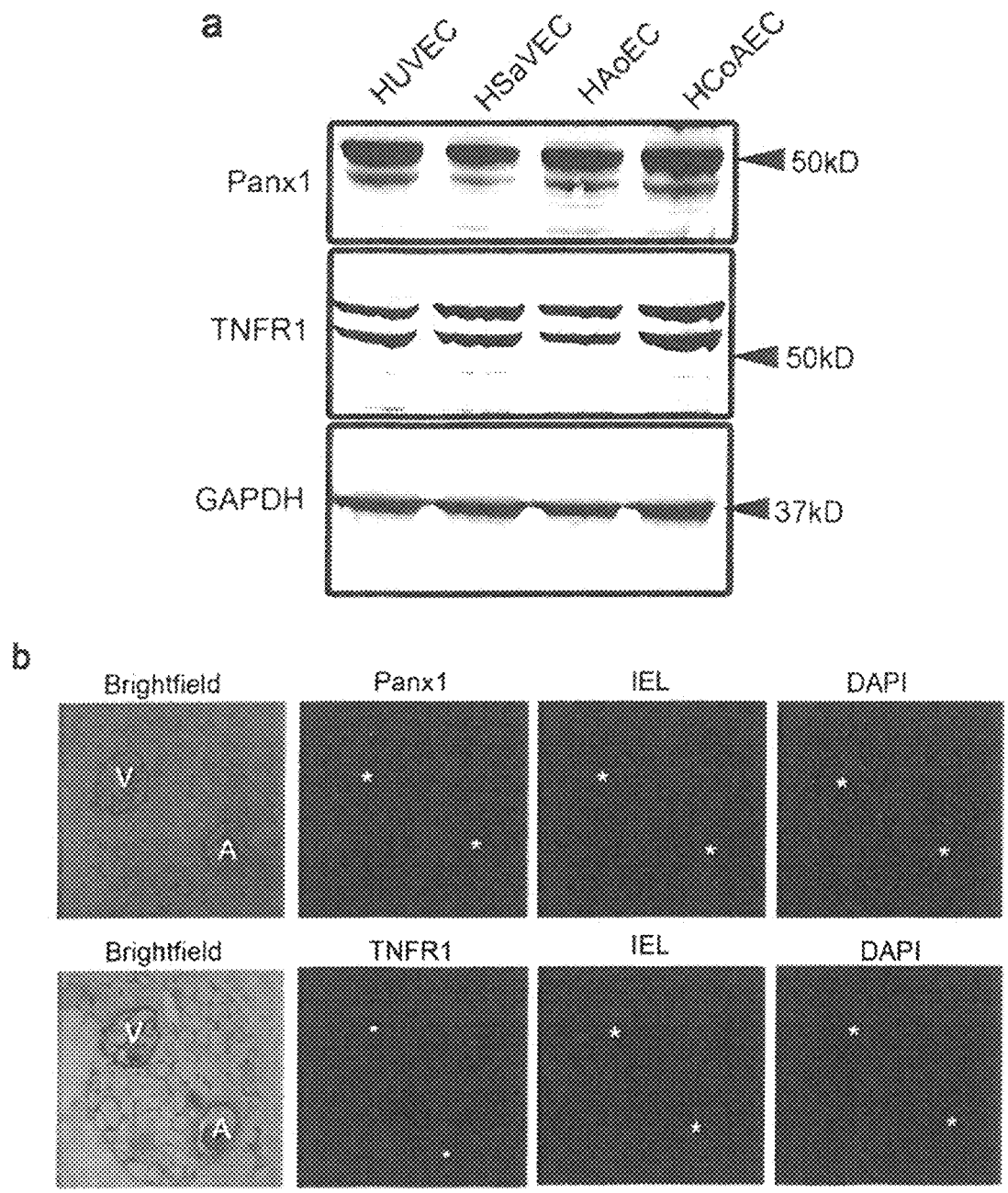
FIG.6 A-B

FIG.7 A-B
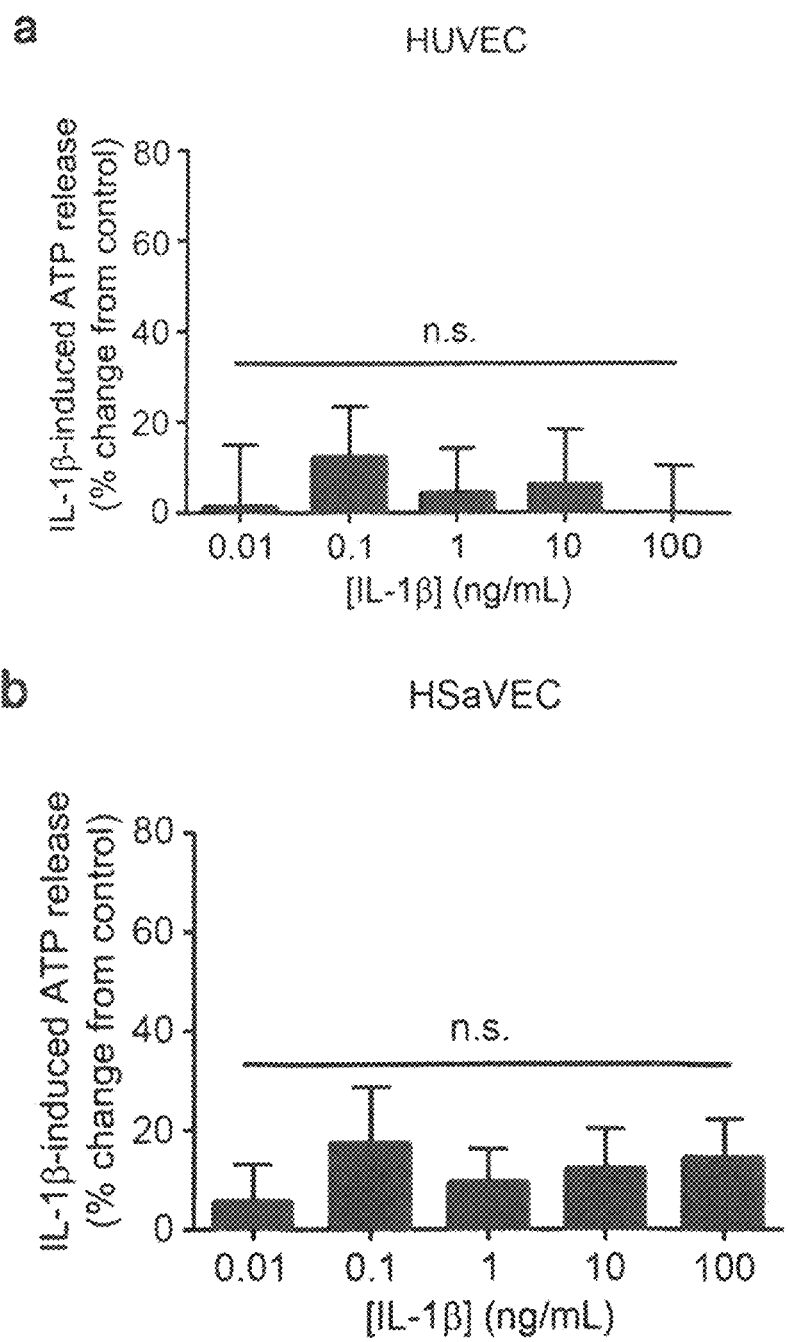

FIG.7 C-D
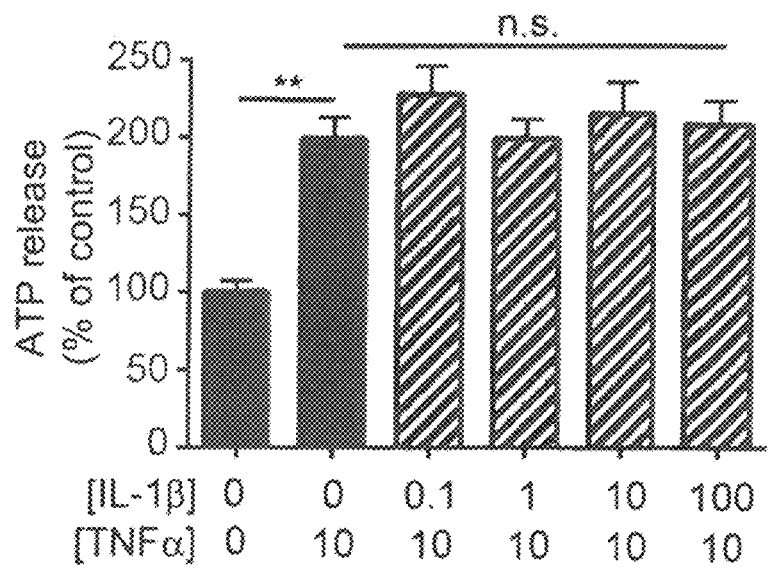
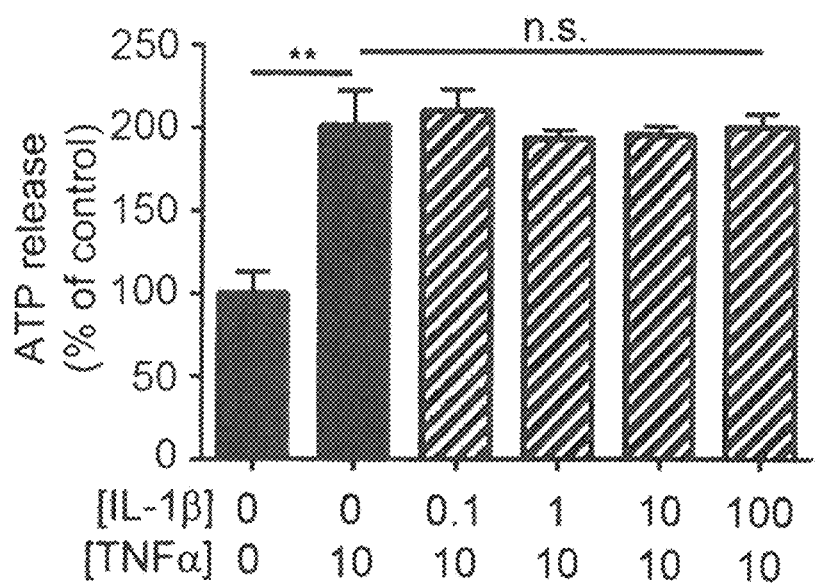

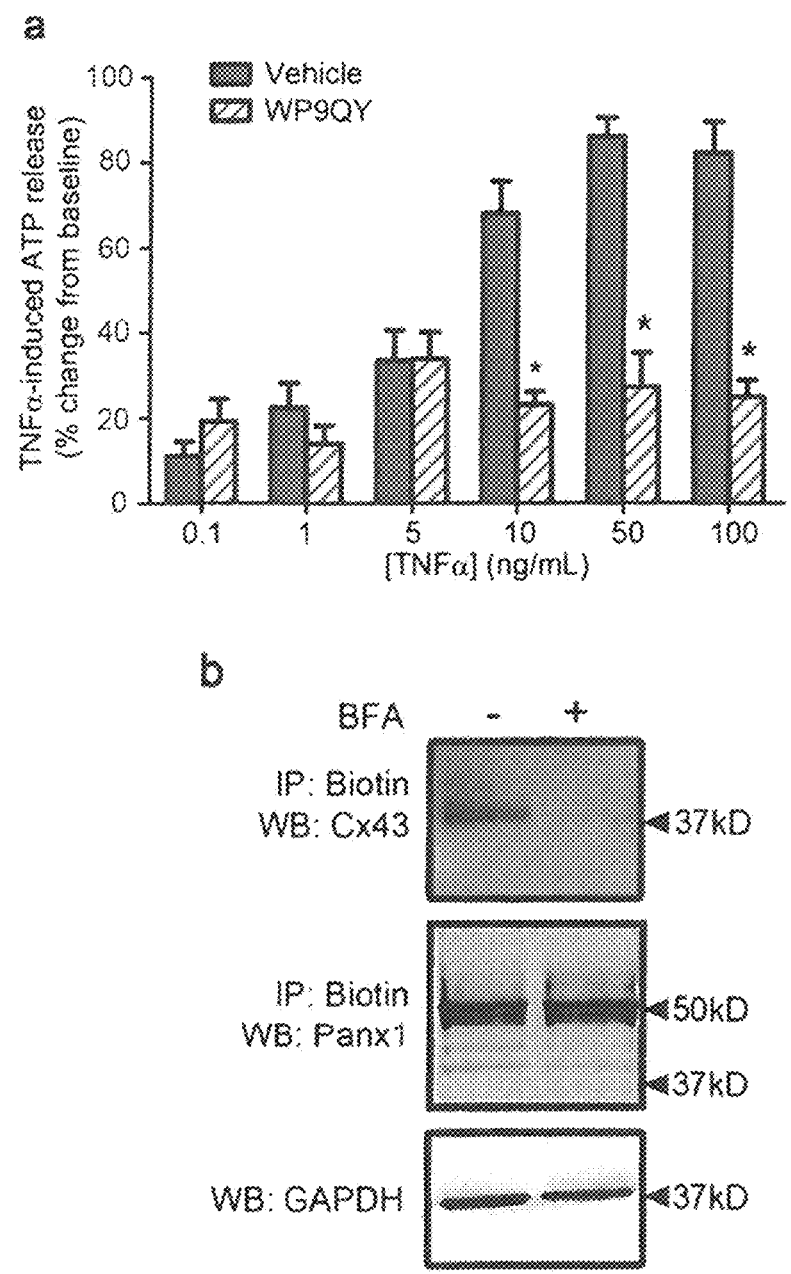
FIG.8 A-B

FIG.8 C-D
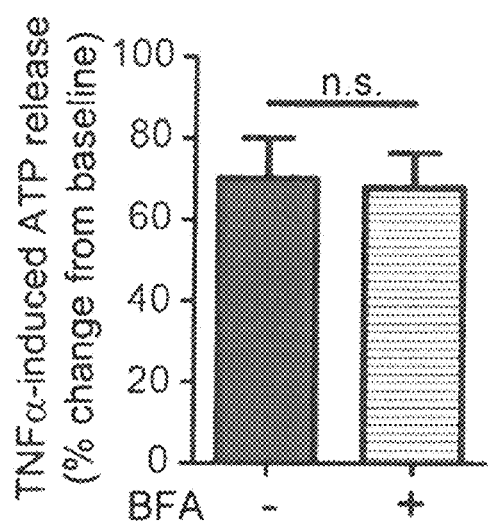
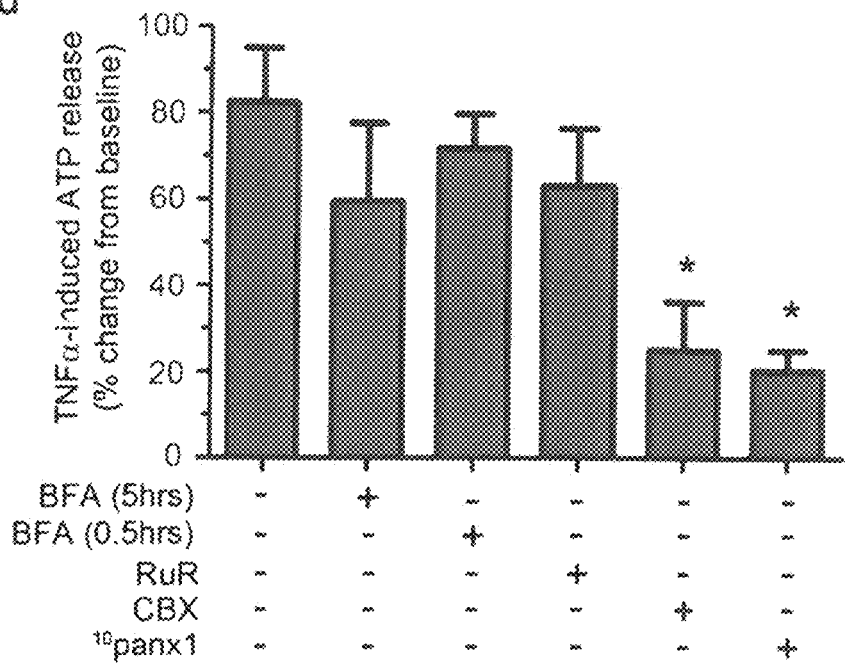

FIG. 8 E-F
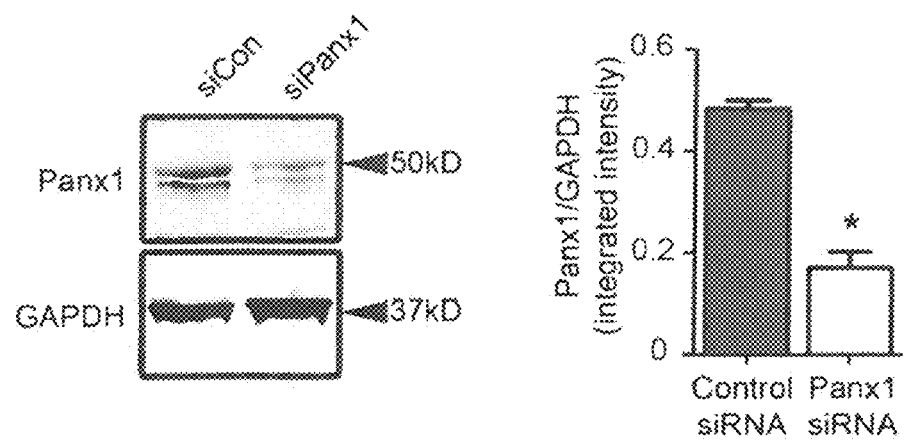
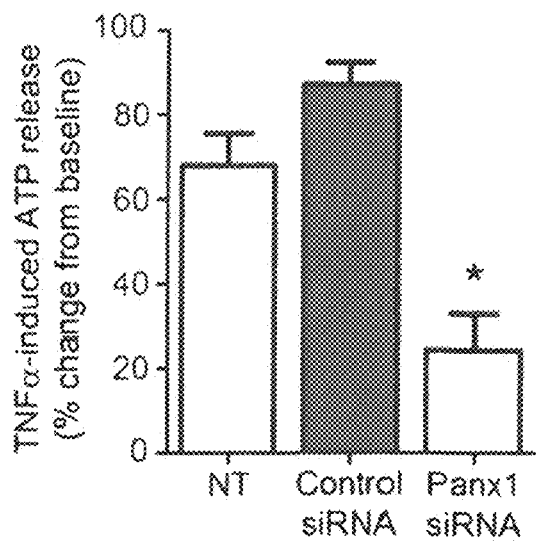

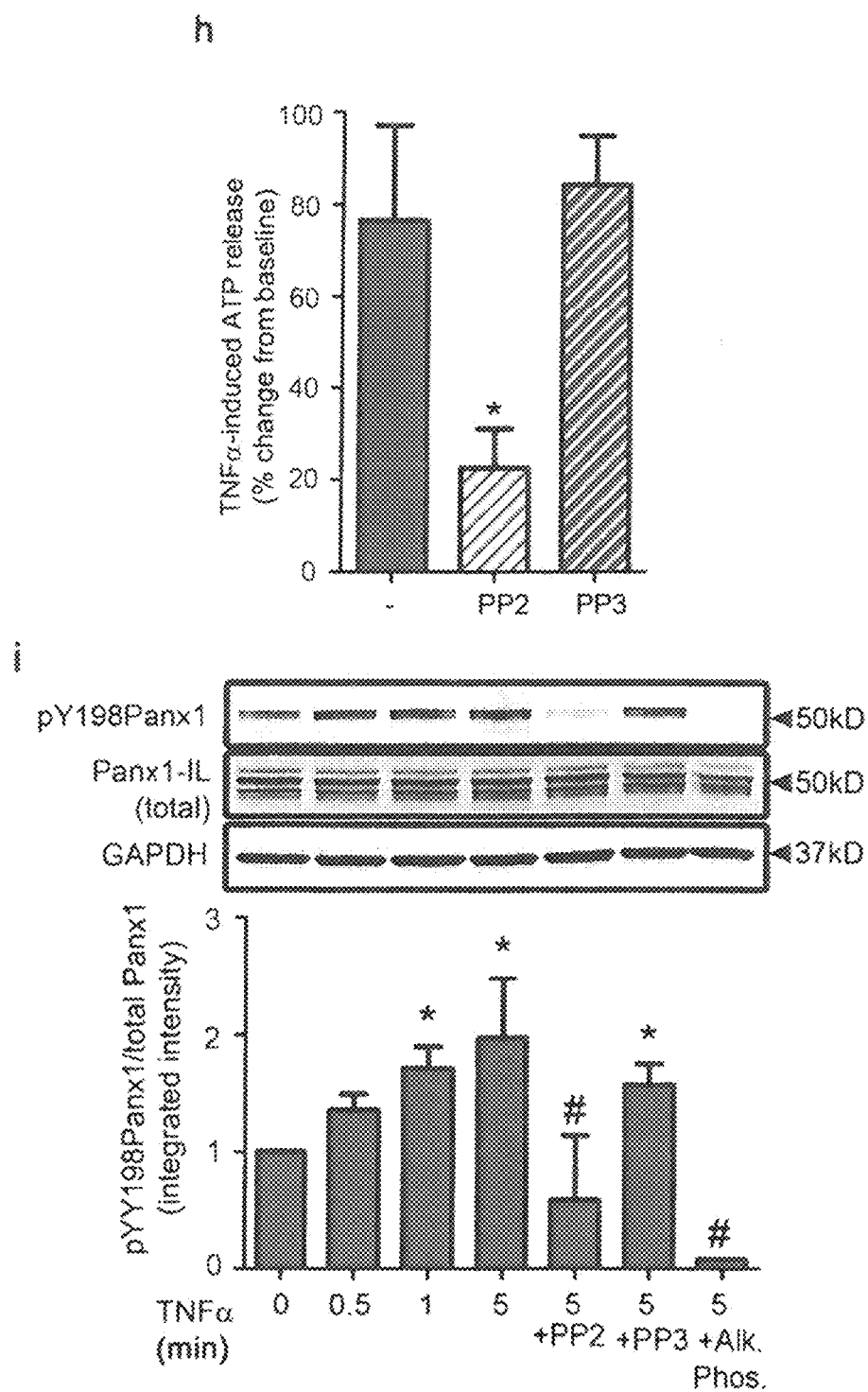
FIG.8 H-I

FIG.9 C-D
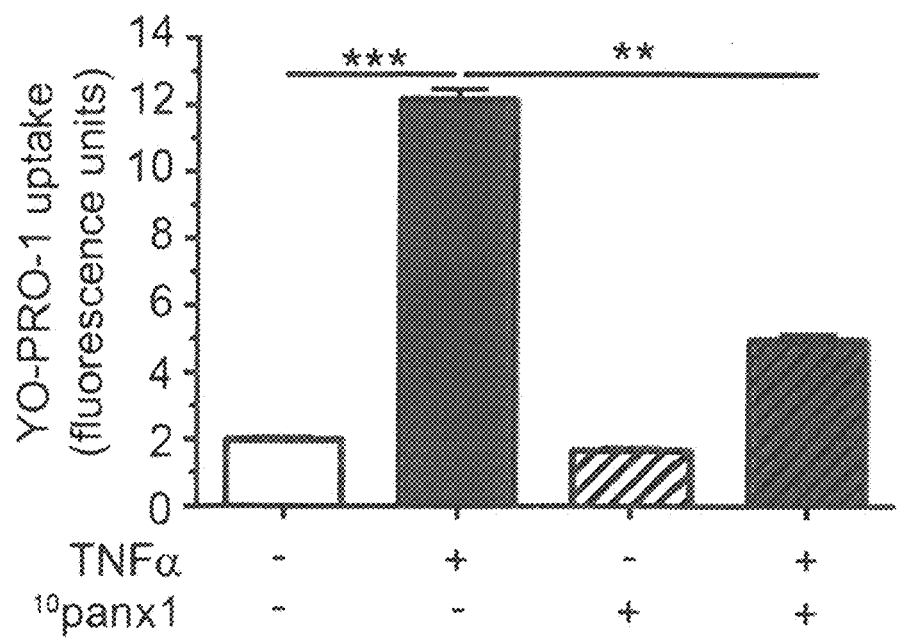
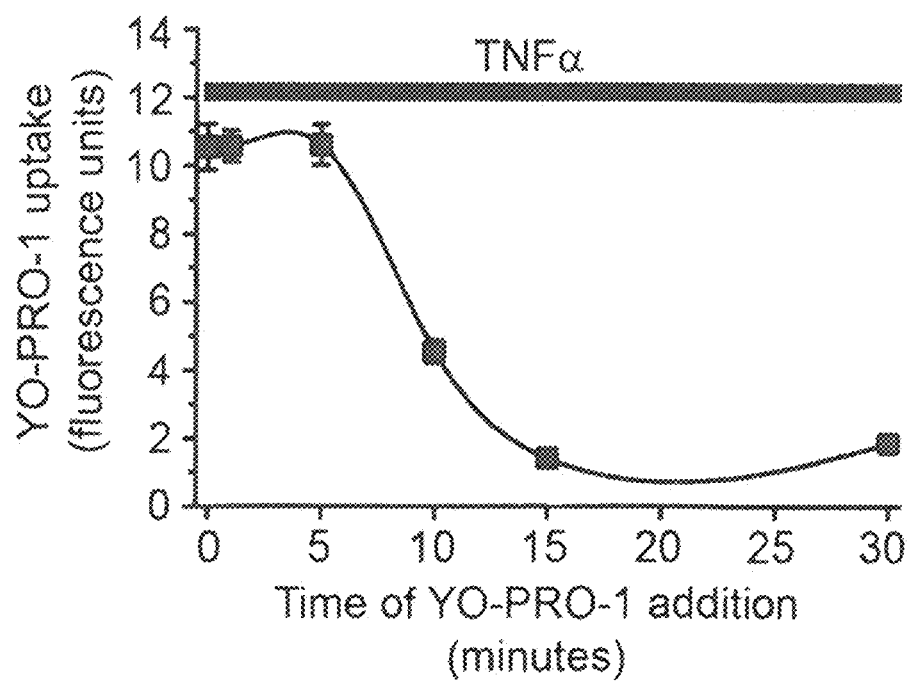

FIG. 11B-C
b
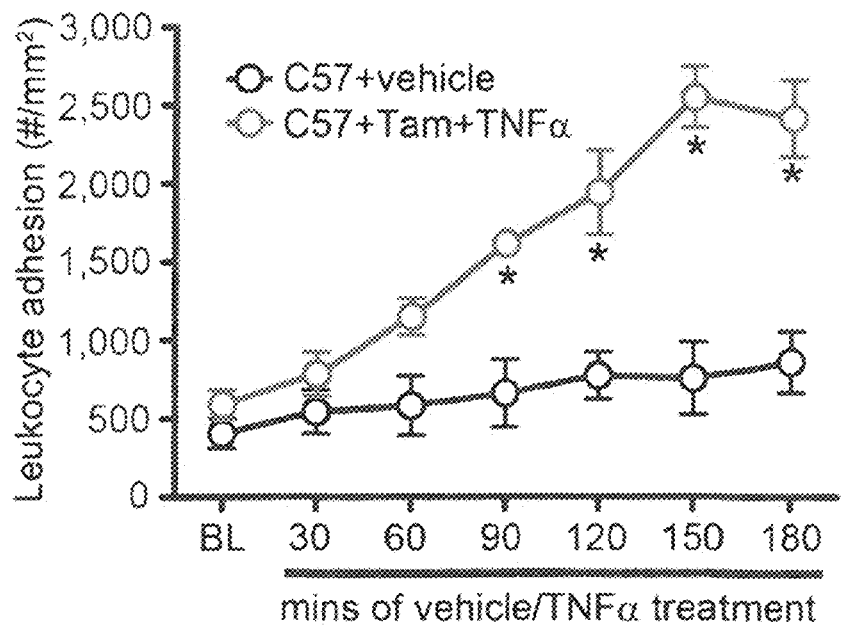
c
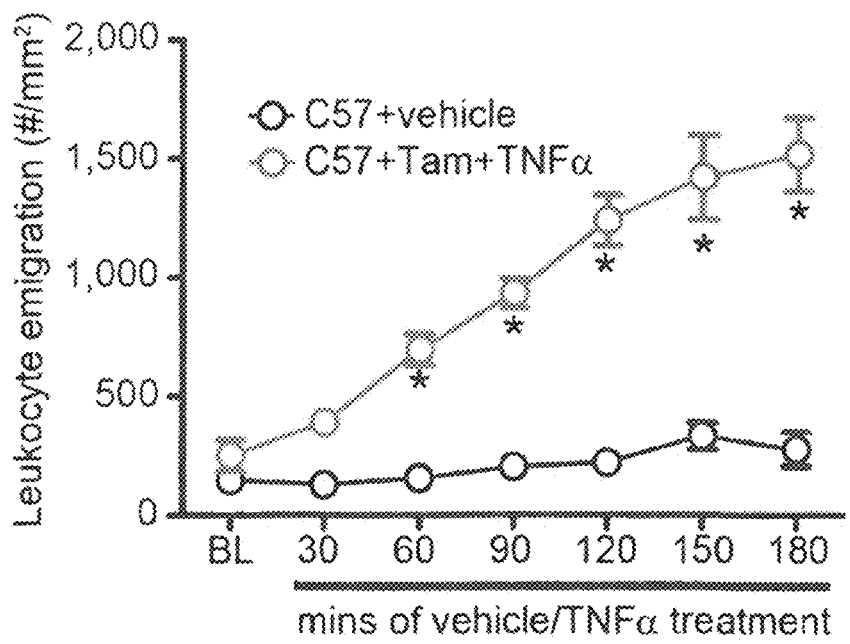

COMPOSITIONS AND METHODS FOR REGULATING LEUKOCYTE ADHESION

CROSS REFERENCE TO RELATED APPLICATIONS

This application is a national stage filing of International Application No. PCT/US2016/044683, filed Jul. 29, 2016, which claims priority under 35 U.S.C. § 119(e) to U.S. Provisional Application Ser. No. 62/198,480 filed Jul. 29, 2015, the disclosures of which are incorporated by reference in their entirety herein.

STATEMENT REGARDING FEDERALLY SPONSORED RESEARCH OR DEVELOPMENT

This invention was made with government support under Grant No. HL120840, awarded by The National Institutes of Health. The government has certain rights in the invention.

BACKGROUND

Purinergic signaling is central in the regulation of vascular tone, which can be mediated by adenosine 5' triphosphate (ATP) and its metabolic breakdown products. Interestingly, ATP can act as either a vasoconstrictor or vasodilator. In the vascular wall, there are multiple sources for ATP; for example, ATP can be released from perivascular nerves and endothelial cells, as well as from circulating erythrocytes. Previously, we showed that cultured smooth muscle cells (SMC) release ATP in response to phenylephrine, an al-adrenoreceptor ($\alpha$1 AR) agonist, and that ATP, purinergic receptors, and the ATP-release channel formed by pannexin1 (Panx1) are synergistically involved in phenylephrine-mediated vasoconstriction.

The pannexins comprise a family of membrane channels similar to innexins, the gap junction-forming proteins in invertebrates. Pannexins share topological similarities but no sequence homology with the gap junction-forming connexin proteins in vertebrates, thus pannexins represent a distinct class of channel-forming proteins. Besides Panx1, two other isoforms have been described, Panx2 and Panx3. Panx1 is the most widely distributed in vertebrates, whereas the presence of Panx2 and Panx3 is restricted to specific tissues. In the systemic vasculature, Panx1 is found in all endothelial cells, but only some SMC; the protein is absent in SMC of conduit arteries and becomes more abundant as the resistance of the arteries increases. Functionally, in apoptotic cells Panx1 channels are activated for cell clearance to support the innate immune response, and in neurons, Panx1 channels are activated in response to cerebral ischemia or to decreases in circulating oxygen. Because Panx1 forms large-pore channels allowing the release of ATP and other intracellular ions and metabolites, channel activity is regulated by various receptors to avoid loss of cellular electrochemical and metabolic homeostasis, which would result in rapid cell death. For example, Panx1-dependent ATP release occurs in response to activation of thrombin receptors, N-methyl-D-aspartate (NMDA) receptors, histamine receptors, and purinergic receptors.

Acute vascular inflammation is a central physiological host defense and repair system that encompasses the innate trafficking and targeting of circulating inflammatory cells (primarily neutrophils and monocytes) to local sites of tissue injury or infection. The vascular inflammatory response is essential for the proper clearance of potentially hazardous pathogens and necrotic cell debris that accompanies the resolution of trauma.

As our understanding of the acute inflammatory response has expanded, a prominent role for extracellular signaling by ATP and its metabolic breakdown products has emerged. The extracellular accumulation of the purine nucleotides ATP, ADP, or adenosine can trigger intracellular signaling cascades through the activation of plasma membrane purinergic receptors. Recently, utilizing pharmacological inhibitors and genetically modified mice, Zerr et al. identified a pivotal role for vascular purinergic receptor $P2Y_1$ in signaling the pro-inflammatory effects of TNF$\alpha$ and interleukin-1$\beta$(IL-1$\beta$). When challenged with TNF$\alpha$ and IL 1$\beta$, mice lacking $P1Y_1$ receptors displayed a significant reduction in leukocyte recruitment. Furthermore, inhibiting $P1Y_1$ function in isolated murine ECs prevented the TNF$\alpha$-dependent upregulation of P-selectin, VCAM1, and ICAM1. In a separate study, the endothelial $P2Y_6$ receptor was shown to control TNF$\alpha$-induced inflammatory gene transcription, where pharmacological inhibition of $P2Y_6$ receptors potently reduced NFKB activity and downstream transcription of the pro-inflammatory cytokine IL-8 and VCAM1. Moreover, mice genetically lacking $P2Y_6$ had reduced VCAM1 expression and preserved EC barrier integrity when challenged with lipopolysaccharide (LPS), a bacterial toxin that increases plasma TNF$\alpha$ levels. As extracellular ATP concentrations increase, ecto-enzymes at the endothelial cell: leukocyte surface actively degrade the purine to ADP, AMP and adenosine. The ectonucleoside triphosphate diphosphohydrolase CD39 (ecto-apyrase) degrades ATP and ADP to AMP while 5'-nucleotidase (CD73) functions to remove the terminal phosphate from AMP yielding adenosine. Consistent with reports implicating purinergic receptors in the vascular inflammatory response, these ecto-enzymes have also been reported to modulate leukocyte recruitment in a number of models of inflammation. For example, mice deficient in CD39 (ecto-apyrase) exhibit enhanced leukocyte targeting to sites of inflammation in the liver and lung. Additionally, mice lacking CD73 have exacerbated leukocyte-EC interactions during inflammatory stress and multiple lines of evidence now indicate adenosine as an anti-inflammatory molecule. Based on these observations, purinergic mechanisms play an important role in regulating vascular inflammation and the relative abundance of extracellular ATP and adenosine balances pro- and anti-inflammatory signaling processes; however, the precise mechanism(s) that mediate/regulate ATP release during this physiological response remains unknown.

The pannexin (Panx) family of channel forming proteins are expressed in the vasculature. Panxs exist in three isoforms (Panx1, Panx2 and Panx3), which are differentially expressed throughout the body. Panx1, the most highly expressed member in the vascular wall, is thought to form hexameric channels permeable to ions and metabolites up to ~1 kD in size, including ATP. To date, the primary function of these channels has been ascribed to the release of ATP and as a result, Panx1 channels provide a strong candidate for vascular ATP release during inflammation. Outside of vascular cells, Panx1 channel function has been implicated in several inflammatory processes. In particular, Panx1 channels promote activation of the inflammasome in macrophages, neurons, and astrocytes, regulate chemotaxis of phagocytes during apoptosis, promote T-cell activation, induce neuronal death during enteric colitis and regulate lung inflammation. Collectively, these studies indicate increased Panx1 channel function during inflammatory stress and provide a framework for understanding the link between cytokine and purinergic signaling pathways in the vasculature. Whether vascular ECs release ATP during inflammatory activation and if Panx1 channels provide the conduit for nucleotide release to promote interactions between circulating inflammatory cells and the endothelium has not been addressed.

There is a long felt need in the art for compositions and methods useful for regulating leukocyte adhesion and emigration. The present invention satisfies these needs.

SUMMARY OF THE INVENTION

Disclosed herein is a molecular signaling pathway involving activation of type 1 TNF receptors, Src family kinases (SFK), and phosphorylation of Panx1 channels that regulates leukocyte emigration and adhesion. This is the first disclosure of phosphorylation of Panx1 channels. It is also disclosed herein that Panx1 channels regulate leukocyte emigration through the venous endothelium during acute inflammation. It is further disclosed that the regulation encompasses leukocyte adhesion. It is further disclosed herein that Panx1 channels are major conduits for ATP release from the venous endothelium during acute inflammatory stress, with channel activation promoting leukocyte adhesion and emigration across the vessel wall. Therefore, the present invention also encompasses compositions and methods useful for stimulating leukocyte adhesion and emigration associated with Panx1 activation, as well as compositions and methods for inhibiting leukocyte adhesion and emigration by inhibiting Panx1.

Utilizing a novel inducible, EC-specific Panx1 knockout mouse line, disclosed herein is a previously unidentified role for Panx1 channels in promoting leukocyte adhesion and emigration through the venous wall during acute systemic inflammation, placing Panx1 channels at the center of cytokine cross-talk with purinergic signaling in the endothelium.

It is disclosed herein that Panx1 channel activation promotes leukocyte adhesion and emigration. In one aspect, Panx1 is activated by TNFα. In one aspect, TNFα induces release of ATP. In one aspect, the release is mediated by Panx1. In one aspect, TNFα induces SFK-dependent activation of endothelial cell Panx1 channels. In one aspect, the endothelial cell is a venous endothelial cell. In one aspect, Panx1 activation and stimulation of leukocyte adhesion and emigration can be inhibited by a Panx1 inhibitor. In one aspect, the inhibitor is a peptide. In one aspect, the peptide is IL2 peptide (KYPIVEQYLKYGRKKQRRR; SEQ ID NO: 3) or [10]Panx1 mimetic peptide (WRQAAFVDSY; SEQ ID NO: 8), or biologically active fragments or homologs thereof. For a summary of sequences used herein, see below. In one aspect, the leukocyte is a monocyte.

In one aspect, the invention encompasses treating a subject in need with an effective amount of an inhibitor of Panx1, when Panx1 is being stimulated and activated. In one embodiment, Panx1 is being activated via a TNFα and SFK pathway. In one embodiment, more than one inhibitor is administered. In one aspect, the activation is selective in endothelial cells of venous origin relative to arterial endothelium. The present invention, therefore, encompasses compositions and methods for regulating and treating vascular inflammation associated with a disease, disorder, condition, or injury in which activation of Panx1 stimulates leukocyte adhesion and emigration. In one aspect, the inflammation is acute vascular inflammation.

In one embodiment, the inhibitor is directed against Panx1. In one aspect, the inhibitor inhibits Panx1 activity Disclosed herein is the unexpected result that the peptide IL2 (SEQ ID NO: 3) (also referred to as UVAPx-1 and PanX) and the Panx1 inhibitory peptide [10]Panx1 (SEQ ID NO: 8) can regulate leukocyte adhesion. As disclosed herein, both IL2 full-length peptide and [10]Panx1 mimetic peptide are inhibitors of TNFα-induced activation of Pannexin1, and it is disclosed herein that they act as inhibitors of TNFα-induced leukocyte emigration and adhesion. The IL2 peptide (SEQ ID NO: 3) was originally described by the present inventors for use in channel activation in smooth muscle cells (Billaud et al., Science Signaling, 2015, 8(364): Published online 2015 Feb. 17). The present application discloses an unexpected property of this peptide, that is, in one aspect it can be used to prevent leukocyte adhesion to TNFα-activated endothelium. Endothelium activated by cytokines (such as TNFα) is the primary manner in which inflammatory cells move from the blood stream to the site of inflammation. The base peptide Intracellular Loop (IL) 2, having the sequence KYPIVEQYLK (SEQ ID NO: 1) was connected to a TAT tag (SEQ ID NO: 2-YGRKKQRRR) so that is can penetrate the cell membrane quickly and easily.

In one embodiment, IL2 peptide (KYPIVEQYLKYGRKKQRRR; SEQ ID NO: 3) mimics an important regulatory region on intracellular loop 2 peptide (KYPIVEQYLK; SEQ ID NO: 1) of both human (K192-K201) and murine (K191-K200) Pannexin1 proteins. It consists of a sequence of 19 amino acids (molecular weight=2510.1 g·mol-1), nine of which are a TAT consensus sequence. That is, it harbors a TAT (transactivator of transcription) consensus sequence (YGRKKQRRR-SEQ ID NO: 2), a derivative of the human immunodeficiency virus (HIV), on the peptide C-terminus, which strongly potentiates peptide delivery across cellular membranes. IL2 peptide (SEQ ID NO: 3) was previously shown to be a potent and specific inhibitor of pannexin1 channel activation and channel opening.

In one embodiment, a useful peptide of the invention is KYPIVEQYLKYGRKKQRRR (SEQ ID NO: 3, consisting of Intracellular Loop 2, SEQ ID NO: 1, combined with TAT, SEQ ID NO: 2), or biologically active homologs or fragments thereof, wherein the biologically active homologs or fragments also have leukocyte adhesion inhibitory activity relative to IL2 peptide (SEQ ID NO: 3). One of ordinary skill in the art will appreciate that conservative amino acid substitutions, additions, or deletions can be made to the peptide and without disrupting activity. In one embodiment, when homologs or fragments are being used, the TAT sequence is not changed, while the IL2 sequence used is a homolog or fragment of KYPIVEQYLK (SEQ ID NO: 1).

In one embodiment, a useful peptide of the invention is KYPIVEQYLK (Intracellular Loop 2; SEQ ID NO: 1), or biologically active homologs or fragments thereof, wherein the biologically active homologs or fragments also have leukocyte adhesion inhibitory activity relative to SEQ ID NO: 1. One of ordinary skill in the art will appreciate that conservative amino acid substitutions, additions, or deletions can be made to the peptide without disrupting the desired activity.

Also disclosed herein is the unexpected result that the known Pannexin 1 inhibitory peptide, [10]Panx1 (WRQAAFVDSY; SEQ ID NO: 8), can also inhibit TNFα-activated emigration and adhesion of leukocytes. [10]Panx1 (SEQ ID NO: 8) is a Panx1 mimetic inhibitory peptide known to block pannexin-1 gap junctions, but the present application discloses its ability to inhibit leukocyte emigration and adhesion.

The present invention provides compositions and methods not just for inhibiting adhesion of leukocytes to endothelial cells in a blood vessel, but also for inhibiting extravasation of the cells from the vessel. In one aspect, the endothelial cells are venous endothelial cells. In one aspect, the compositions and methods provide for inhibiting recruitment of leukocytes to inflammatory foci. In one aspect, recruitment is stimulated by TNFα activation of Panx1.

In one embodiment, the present invention provides for treating a subject in need thereof by administering an effective amount of a peptide of the invention that inhibits Pannexin1 activity. In one aspect, the peptide is IL2 peptide (SEQ ID NO: 3), or a biologically active fragment or homolog thereof. In one aspect, a pharmaceutical composition is administered to the subject, wherein the composition comprises an effective amount of the peptide and a pharmaceutically-acceptable carrier.

In one aspect, a peptide or other Pannexin1 inhibitor of the invention inhibits leukocyte adhesion. In one aspect, it inhibits adhesion to endothelial cells. In one aspect, it inhibits adhesion to endothelium. In one aspect, it inhibits adhesion to venous endothelial cells. In one aspect, more than one inhibitor is used.

In one aspect, a peptide of the invention is attached to a different (second) peptide at the C-terminus for use in delivery to a cell or in entering a cell.

Sequences used herein include:

```
                                             SEQ ID NO: 1
-KYPIVEQYLK-intracellular loop 2 (not to be
confused with IL2 peptide)

SEQ ID NO: 2
-YGRKKQRRR-TAT sequence

SEQ ID NO: 3
-KYPIVEQYLKYGRKKQRRR-full-length IL2 peptide (SEQ
ID NOs: 1 and 2 combined)

SEQ ID NO: 4
-VGQSLWEISE-intracellular loop 1

SEQ ID NO: 5
-RRLKVYEILPTFDVLH-CT1

SEQ ID NO: 6
-IPTSLQTKGE-CT2

SEQ ID NO: 7
-IYLYVEQKPY-scrambled intracellular loop 2

SEQ ID NO: 8
-WRQAAFVDSY-[10]Panx1 peptide
```

The present invention further encompasses attaching a TAT sequence or similar sequences to other peptides used herein (including SEQ ID NO: 8) or encompassed by the practice of the invention.

The compositions and methods of the present invention are useful for preventing and treating injuries, diseases, disorder, infections, and conditions where regulating pannexin is beneficial. In one aspect, the compositions and methods of the invention are useful for treating a subject who has had a stroke, where pannexins mediate leukocyte adhesion and exacerbate the effects of the stroke. Therefore, in one aspect, the present invention provides for administering one of more compounds of the invention to regulate pannexin activity and inhibit or prevent leukocyte infiltration. In one aspect, the compositions and method inhibit or prevent leukocyte infiltration at the site of a stroke. In one aspect, this method improves stroke recovery by inhibiting Pannexin1 activity associated with inflammation and injury. In one aspect, useful compounds of the invention include, but are not limited to, IL2 peptide (SEQ ID NO: 3) and [10]Panx1 peptide (SEQ ID NO: 8). In one aspect, the stroke is an ischemic stroke.

In addition to being useful for treating stroke victims, in one aspect, the compositions and methods described herein are useful for treating inflammation associated with injuries, diseases, infections, and disorders, including, but not limited to, aortic aneurism, sepsis, inflammatory-associated hypertension, osteoarthritis, and atherosclerosis. In one embodiment, the inflammatory disorders occur due to autoimmunity, transplantation, acute kidney injury (AKI), lung transplant, ischemia reperfusion, and reperfusion injury (ischemia reperfusion injury (IRI)). Other diseases and disorders where the present invention is useful is autoimmune type-1 diabetes, acute kidney injury occurring due to ischemia reperfusion, autoimmune lupus glomerulonephritis, obesity-linked Type-2 diabetes, obesity, hyperglycemia, and diabetic nephropathy. In another aspect, the compositions and methods disclosed herein are useful in obesity by blocking ATP release by adipocytes and preventing and inhibiting leukocyte/macrophage infiltration.

In yet another embodiment, the compositions and methods of the invention can be employed for treatment of inflammatory conditions arising due to ischemia reperfusion injury of various organs including, kidneys, lung and heart.

In one embodiment, the compositions and methods of the invention are useful for inhibiting inflammation and for inhibiting inflammatory cell recruitment at a site of tissue injury, disease, disorder, or condition associated with Panx1 activation.

The invention further provides for stimulating leukocyte adhesion or emigration at a site in a subject in need thereof by treating the subject with an effective amount of a compound that activates Pannexin1.

Based on the disclosure provided herein, one of ordinary skill in the art will be able to determine the amount to administer and how often a dose should be administered, taking into consideration things such as the specific injury, disease, or disorder being treated and the age, sex, and health of the subject being treated.

In one embodiment, a dose range from about 50 μg/kg body weight to about 1,000 μg/kg body weight is encompassed by the methods of the invention. In one aspect, the dose range is from about 50 μg/kg body weight to about 500 μg/kg body weight. In one aspect, the dose range is from about 500 μg/kg body weight to about 1,000 μg/kg body weight. In one aspect, the dose range is from about 75 μg/kg body weight to about 900 μg/kg body weight. In another aspect, the dose range is from about 100 μg/kg body weight to about 800 μg/kg body weight. In one aspect, the dose range is from about 200 μg/kg body weight to about 700 μg/kg body weight. In one aspect, the dose used is about 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 280, 290, 300, 325, 350, 375, 400, 425, 450, 475, 500, 525, 550, 575, 600, 650, 700, 750, 800, 850, 900, 950, or 1,000 μg/kg body weight. In one aspect, doses can be broken up and administered as more than one sub-dose.

The present invention further encompasses the use of compositions and methods that inhibit upstream components of the TNFα activation of Pannexin1 in endothelial cells to inhibit inflammatory responses, leukocyte adhesion, and leukocyte emigration, as well as downstream components. These include inhibitors of TNFα interaction with its receptor, inhibition or signaling of its receptor, and inhibitors of the src Kinase Family phosphorylation of Pannexin1.

The present invention also provides compositions and methods for identifying inhibitors of TNFα activation of Panx1. Assays are also provided to verify that a compound identified with the activity can also inhibit leukocyte adhesion and emigration. It is disclosed herein that venous endothelial cells release ATP upon activation by TNFα, that Panx1 channels mediate this effects, and that TNFα induces Src Family Kinase-dependent activation of endothelial cell Panx1 channels. The assays disclosed herein provide ample methods for screening compounds for the desired activity. In one embodiment, the method comprises contacting a venous endothelial cell comprising Pannexin1 with TNFα and with a test compound. Then, it can be determined whether the venous endothelial cell Pannexin1 is activated by measuring at least one marker of venous endothelial Pannexin1 activation and comparing the level of that marker to the level of the marker before activation, to a standard level, or to a level measured when an otherwise identical venous endothelial cell is contacted with TNFα but not the test compound. Markers include, but are not limited to, amount of ATP released, phosphorylated Pannexin1, leukocyte adhesion to an endothelial cell, and leukocyte emigration. One of ordinary skill in the art can generate dose response curves for the inhibitors and can generate standard curves for measuring the levels of the markers.

In one aspect, the site of the injury, disease, disorder, or condition comprises a site of inflammation. In one aspect, the site of inflammation is a localized focus of inflammation.

In one embodiment, the injury, disease, disorder, or condition is selected from the group consisting of stroke, ischemic stroke, aortic aneurism, sepsis, inflammatory-associated hypertension, osteoarthritis, and atherosclerosis.

Administration can be by any appropriate means or made at any appropriate site.

Various aspects and embodiments of the invention are described in further detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1: Venous endothelial cells release ATP when activated by TNFα (a) Schematic of ex vivo vascular perfusion assay. (b) TNFα-induced ATP release from isolated murine mesenteric venules. TNFα promoted a time and dose dependent increase in ATP release from the endothelium. $*=p<0.05$, $=p<0.01$ and $*=p<0.001$ as compared to vehicle perfused controls (n=4). (c) LDH release from isolated venules perfused with TNFα or lysis buffer. (d) ATP release from isolated mesenteric venules (V) and paired arterioles (A) in response to TNFα (50 ng/mL) perfusion. $***=p<0.001$ vs. venule (n=4) (e) Time course of ATP release from mesenteric venules following inhibition of TNFR1 with WP9QY (10 µM). $*=p<0.05$ and $^=p<0.01$ vs. corresponding vehicle time point (n=4). (f) Dose response of primary human venous (HUVEC and HSaVEC) and arterial (HAoEC and HCoAEC) ECs to TNFα. HUVEC: human umbilical vein endothelial cell, HSaVEC: human saphenous vein endothelial cell, HAoEC: human aortic endothelial cell, HCoAEC: human coronary artery endothelial cell. $*=p<0.01$ compared to unstimulated cells and $\#=p<0.005$ as compared to venous cells (n=5). (g) Time course of ATP release from cultured arterial and venous ECs. Cells were stimulated with 10 ng/mL TNFα. (h) Dose response of HUVEC to TNFα following inhibition of TNFR1 with WP9QY (10 µM). $*=p<0.05$ as compared to vehicle control (n=5). All data are presented as mean±SEM (error bars). Statistical analyses were performed using One-way ANOVA.

Figure 4A:
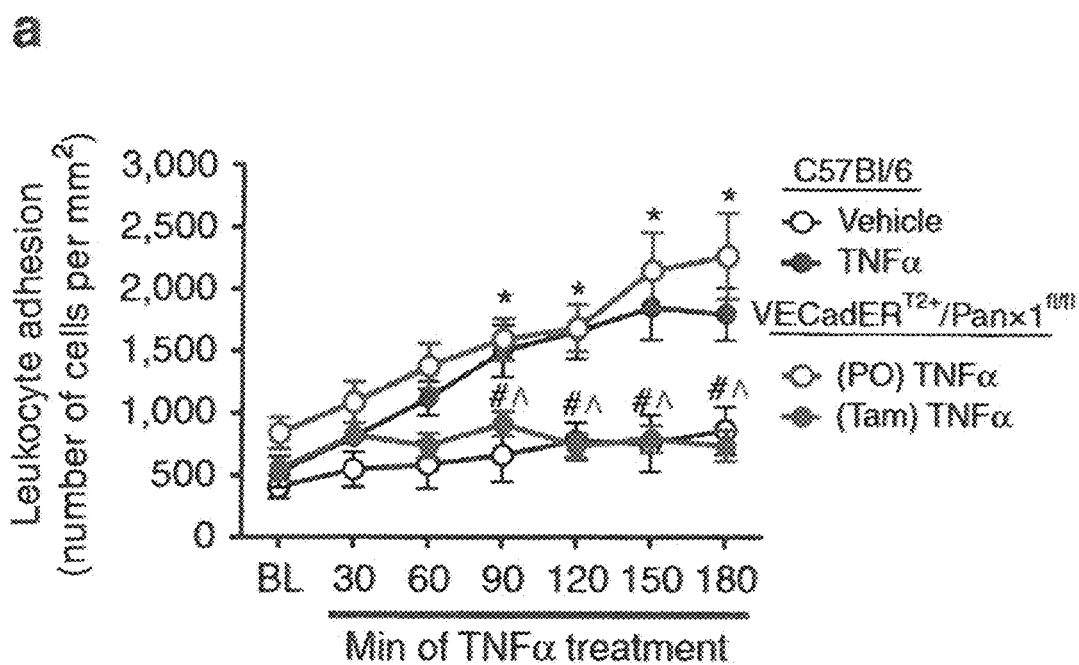
Figure 4:
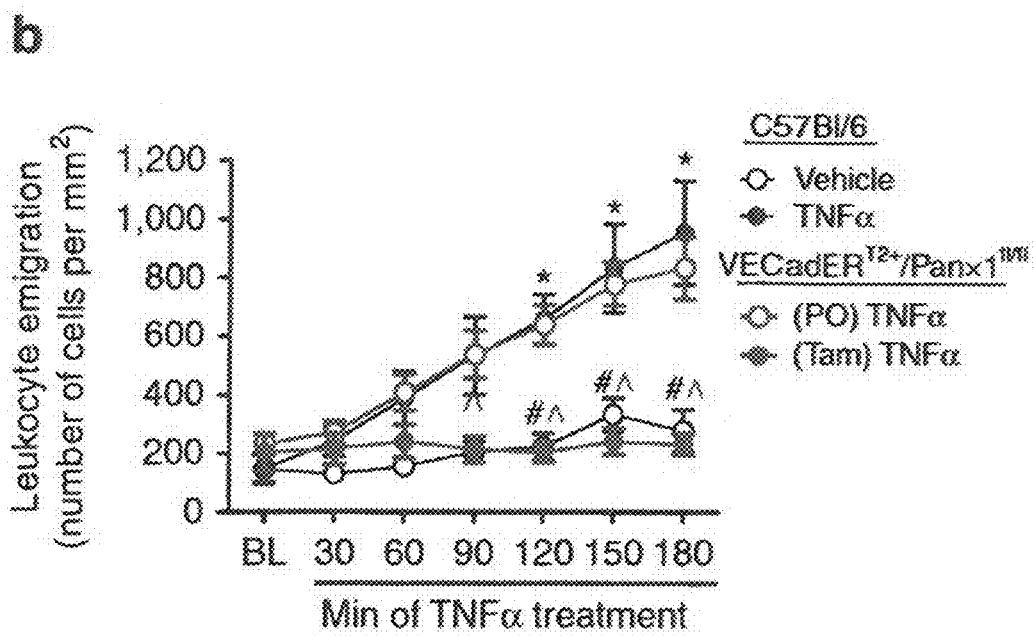
Figure 4:
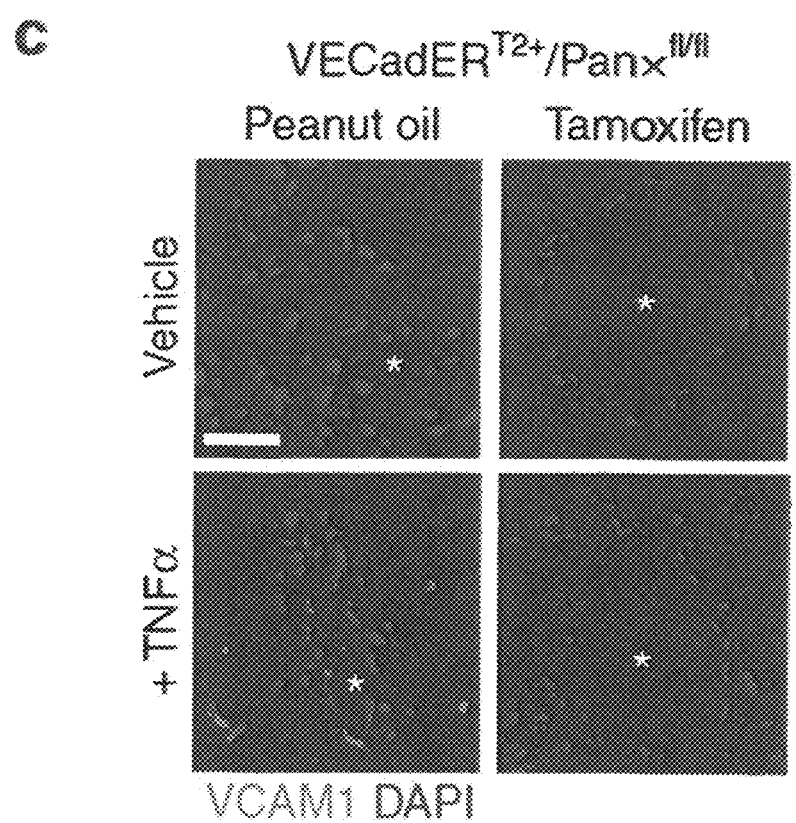
Figure 4:
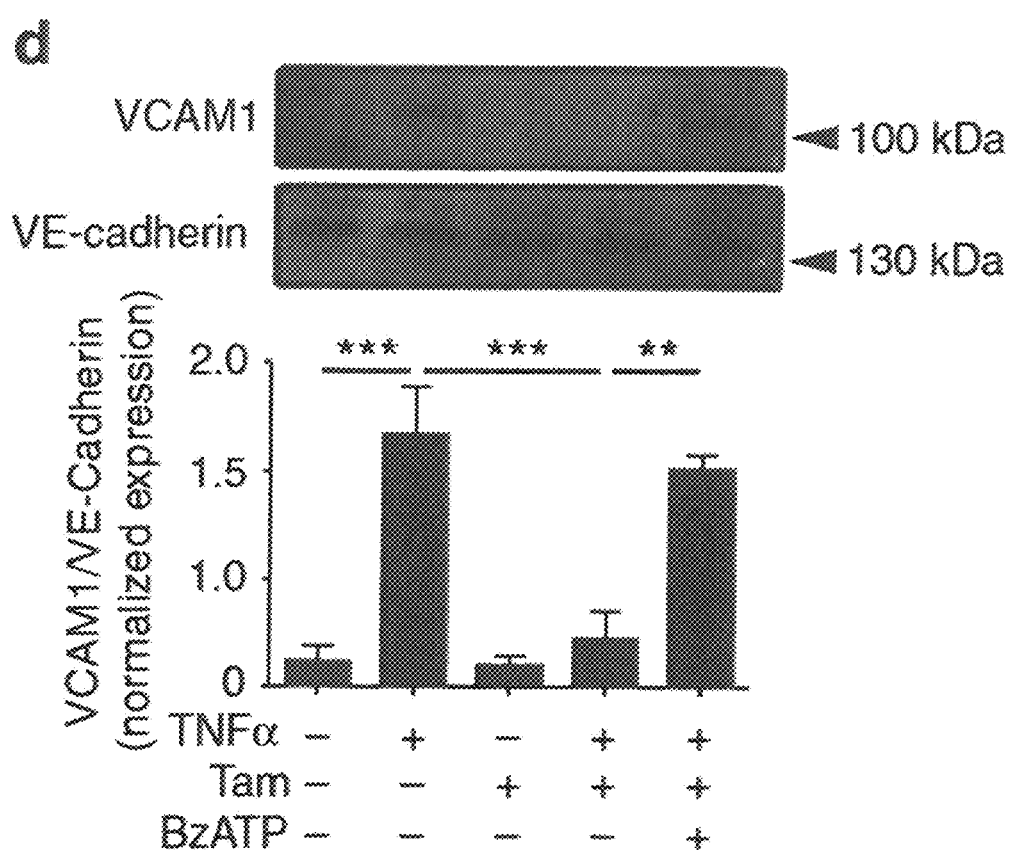
Figure 4:
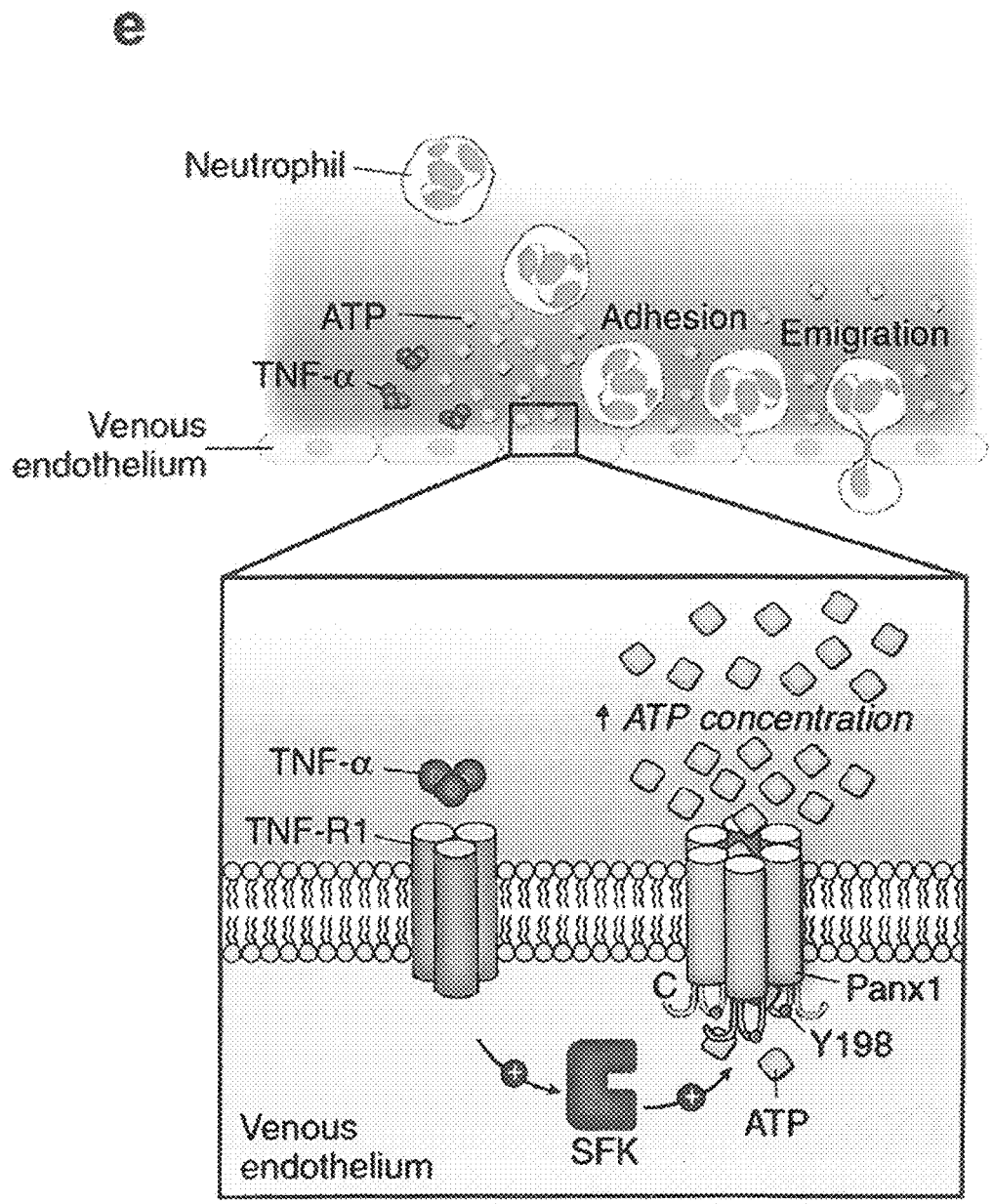

FIG. 4: EC Panx1 channels promote leukocyte adhesion and emigration (a-b) Quantification of endogenous leukocyte adhesion (a) and emigration (b) in WT C57B1/6J mice and mice lacking Panx1 specifically in the endothelium (VECadER$^{T2+}$/Panx1$^{fl/fl}$) in the acute inflammatory response. Acute inflammation was induced by topically applying recombinant murine TNFα to exteriorized cremaster muscles in anesthetized mice. *=p<0.01 as compared to baseline, #=p<0.005 as compared to C57B1/6J mice treated with TNFα and ^=p<0.01 as compared to PO injected VECadER$^{T2+}$/Panx1$^{fl/fl}$ mice treated with TNFα by Two-way ANOVA (n=5-6 mice per group). (c) Immunofluorescence micrographs for VCAM1 expression in isolated mesenteric venules from VECadER$^{T2+}$/Panx1$^{fl/fl}$ mice (PO or Tam injected) treated with vehicle or TNFα (50 ng/mL) for 2 hours. * indicate the vessel lumen and nuclei are stained with DAPI (blue). Scale bar is 30 μm. (d) Western blot analysis of VCAM1 expression in isolated mesenteric venules from VECadER$^{T2+}$/Panx1$^{fl/fl}$ mice following TNFα (50 ng/mL) treatment. Exogenous BzATP (10 μM) was applied to assess the potential to rescue VCAM1 upregulation. =p<0.01 and *=p<0.005 by One-way ANOVA (n=3). (e) Mechanism of TNFα-induced ATP release from venous ECs in the acute inflammatory response. All data are presented as mean±SEM (error bars).

Figure 5:
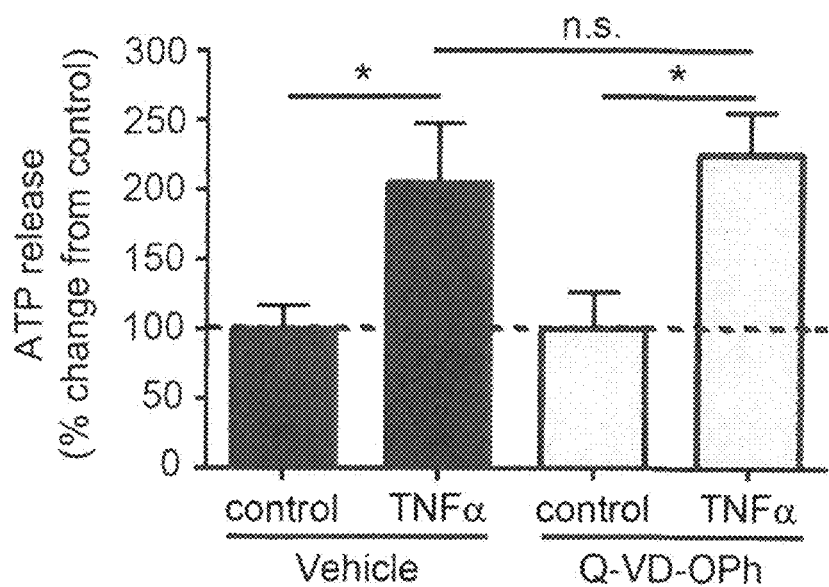

FIG. 5: TNFα induces ATP release from HUVEC and HSaVEC independent caspase activation (a)TNFα induced ATP release from HUVEC in the presence of the pan-caspase inhibitor QVD-OPh (100 μM). Cells were treated with recombinant human TNFα (100 ng/mL) for 30 minutes. *=p<0.05 as compared to unstimulated controls by One-way ANOVA (n=4). Data are presented as mean±SEM (error bars).

Figure 6:
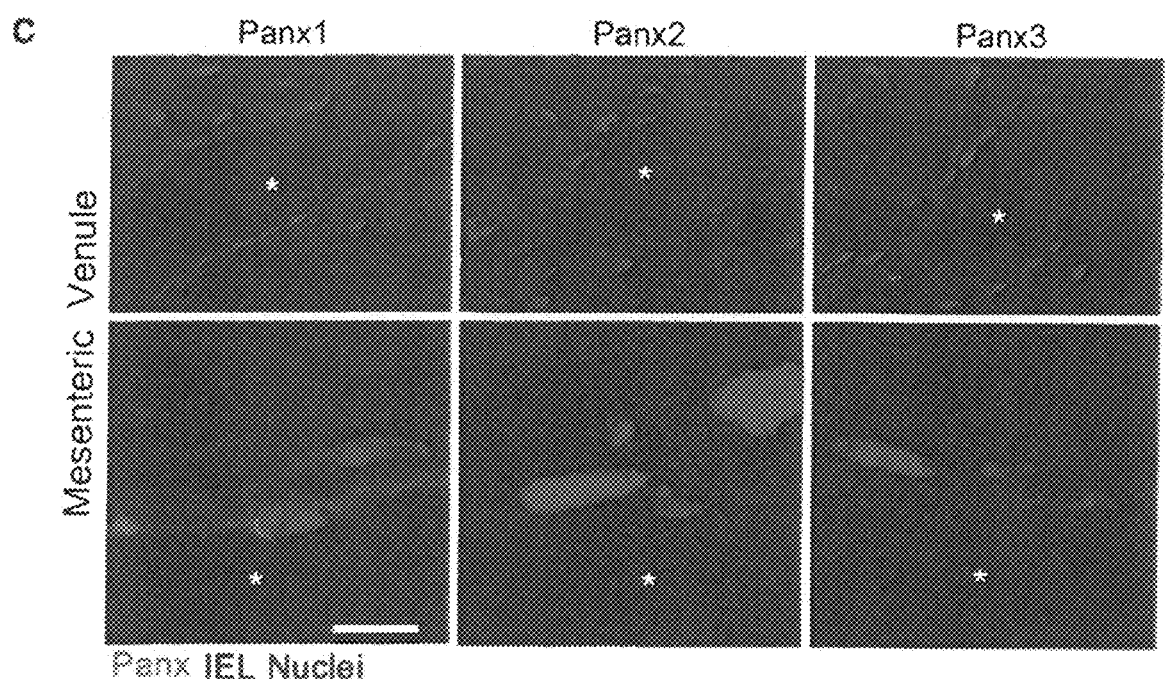

FIG. 6: TNFR1 and Panx1 expression do not differ between venous and arterial ECs (a) Western blot of Panx1 and TNFR1 expression in primary human venous (HUVEC, HSaVEC) and arterial (HAoEC, HCoAEC) endothelial cells. (b) Immunofluorescence micrographs of Panx1 and TNFR1 expression in isolated mesenteric arteriole (A) and venule (V) pairs. * indicate the vessel lumen, autofluorescence of the IEL is in green and nuclei are stained with DAPI (blue). (c) Panx 1, 2 and 3 expression profile in isolated mesenteric venules. Panx expression is in red, autofluorescence of the IEL is in green and nuclei are stained with DAPI (blue).

FIG. 7: IL-1β does not promote ATP release from HUVEC or HSaVECs (a-b) ATP release from HUVEC (a) and HSaVEC (b) to increasing concentrations of recombinant human IL-1β. (c-d) ATP release from HUVEC (c) and HSaVEC (d) to co-stimulation with TNFα (10 ng/mL) and increasing concentrations of IL-1β. **=p<0.01 compared to unstimulated controls by One-way ANOVA (n=4). All data are presented as mean±SEM (error bars).

Figure 8:
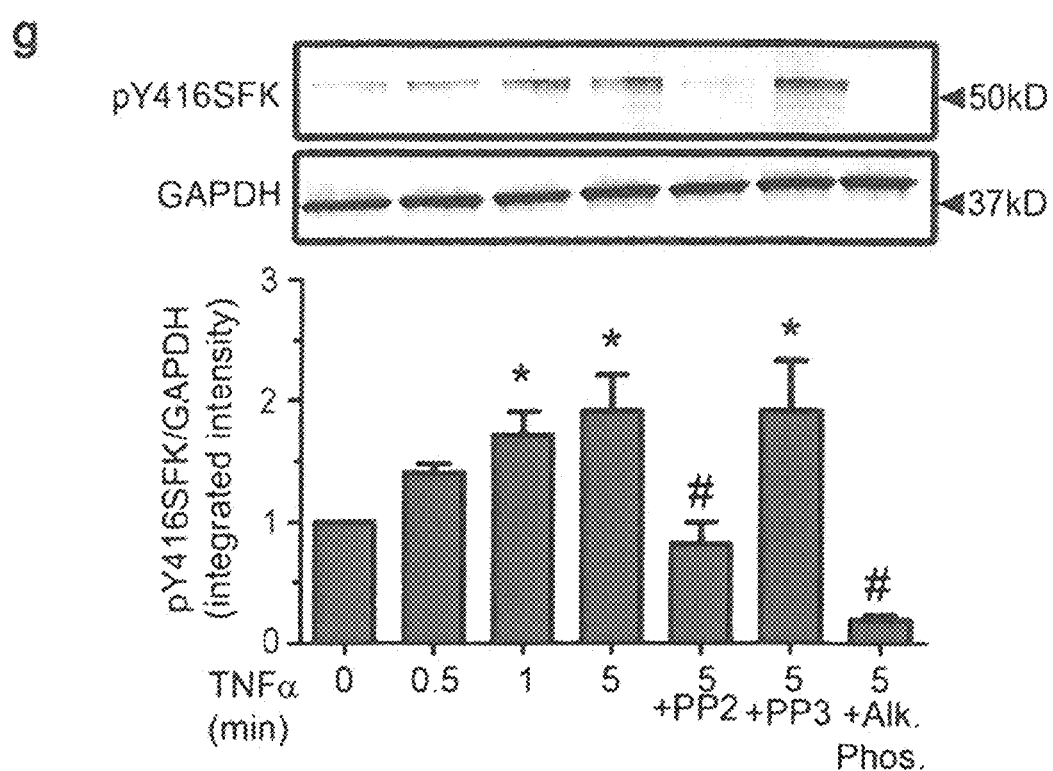
Figure 8:
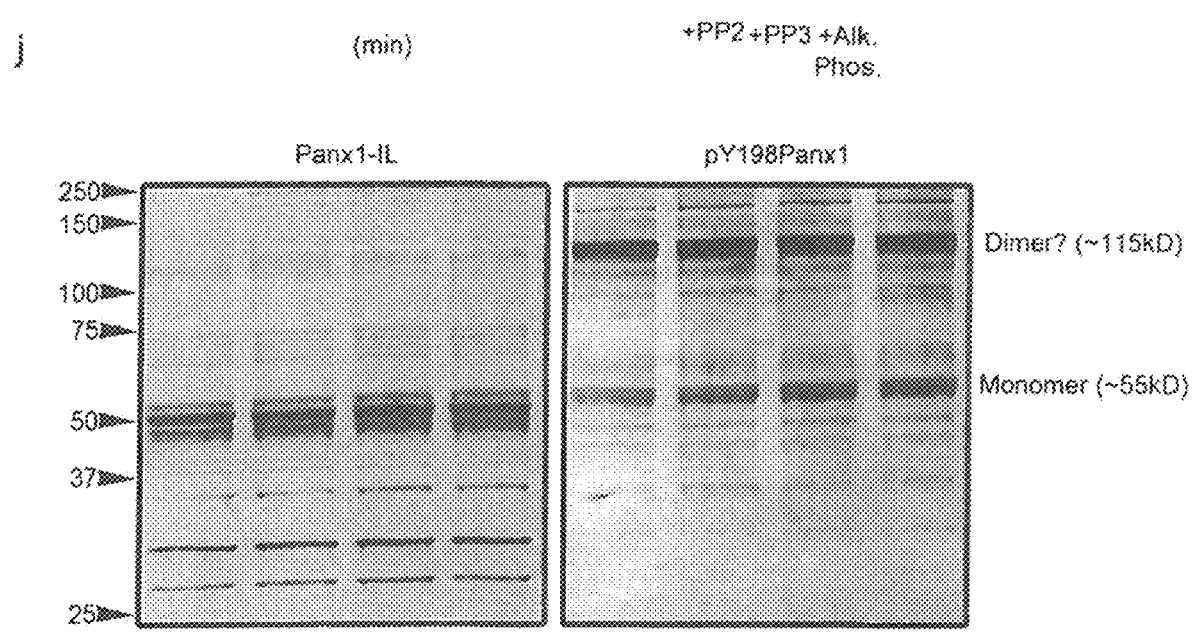

FIG. 8: HSaVEC release ATP via Panx1 channels in response to TNFα via a SFK-dependent mechanism (a) Dose response of Human Saphenous Vein Endothelial Cells (HSaVEC) to TNFα before and after inhibition of TNFR1 with WP9QY (10 μM). *=p<0.01 as compared to vehicle (n=5). (b) Representative Western blot of HSaVEC subjected to treatment with brefeldin A (BFA; 5 μg/mL) for 5 hours and subsequent cell surface biotinylation of membrane proteins. Panx1 and Cx43 plasma membrane localization was assessed. (c) ATP release from BFA treated HSaVEC in response to TNFα (10 ng/mL) treatment for 30 minutes. (d) Summary data of pharmacological inhibitors assessed for inhibition of TNFα-induced ATP release from HSaVEC. BFA (30 min): inhibition of vesicular release; BFA (5 hr): inhibition of Cx hemichannels; Ruthenium Red (RuR): antagonist of CALHM1 channels; CBX and $^{10}$panx1: Panx1 antagonists. *=p<0.05 as compared to HSaVEC treated with TNFα only (n=5). (e) Representative Western blot of siRNA knockdown of Panx1 in HSaVEC, and its quantification. *=p<0.05 (n=3). (f) ATP release from siRNA treated HSaVEC from (e) in response to TNFα (10 ng/mL). NT: non-transfected. *=p<0.05 (n=4). (g) Western blot analysis of SFK activation in HSaVEC in response to TNFα stimulation (10 ng/mL). A phospho-specific antibody against Y416 in SFKs (pY416SFK) was used as an indicator of SFK activation. SFK activation was blocked with the pharmacological antagonist PP2 (10 μM) but not by its inactive analog PP3 (10 μM). *=p<0.05 compared to vehicle control (lane 1) and #=p<0.01 compared to 5 min TNFα stimulation (lane 4) (n=3). (h) TNFα-induced ATP release from HSaVEC following SFK inhibition with PP2 (10 μM). *=p<0.05 compared to control and PP3 (n=5). (i) Western blot analysis of Panx1 phosphorylation at Y198 in HSaVECs stimulated with TNFα (10 ng/mL). Panx1 phosphorylation was detected using a phospho-specific antibody to Y198 in Panx1 (pY198Panx1). Phospho-signal was normalized to total Panx1 expression using an antibody raised against the non-phosphorylated epitope in the Panx1 intracellular loop (Panx1-IL).*=p<0.05 compared to vehicle control (lane 1). #=p<0.01 compared to 5 min TNFα stimulation (lane 4) (n=3). (j) Representative uncropped Panx1-IL and pY198Panx1 Western blots. The presence of a potential dimer species is shown in the pY198Panx1 blot. All data are presented as mean±SEM (error bars). Statistical analyses were performed using One-way ANOVA.

Figure 9:
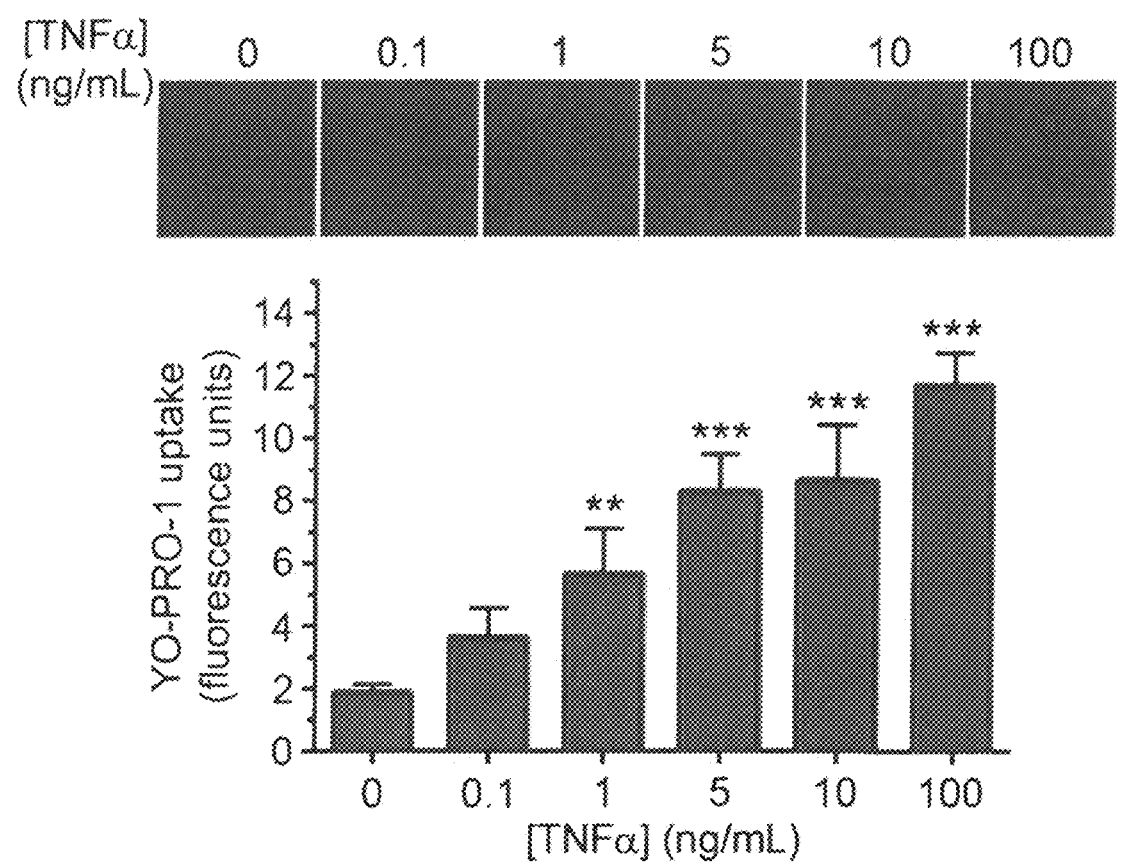
Figure 9:
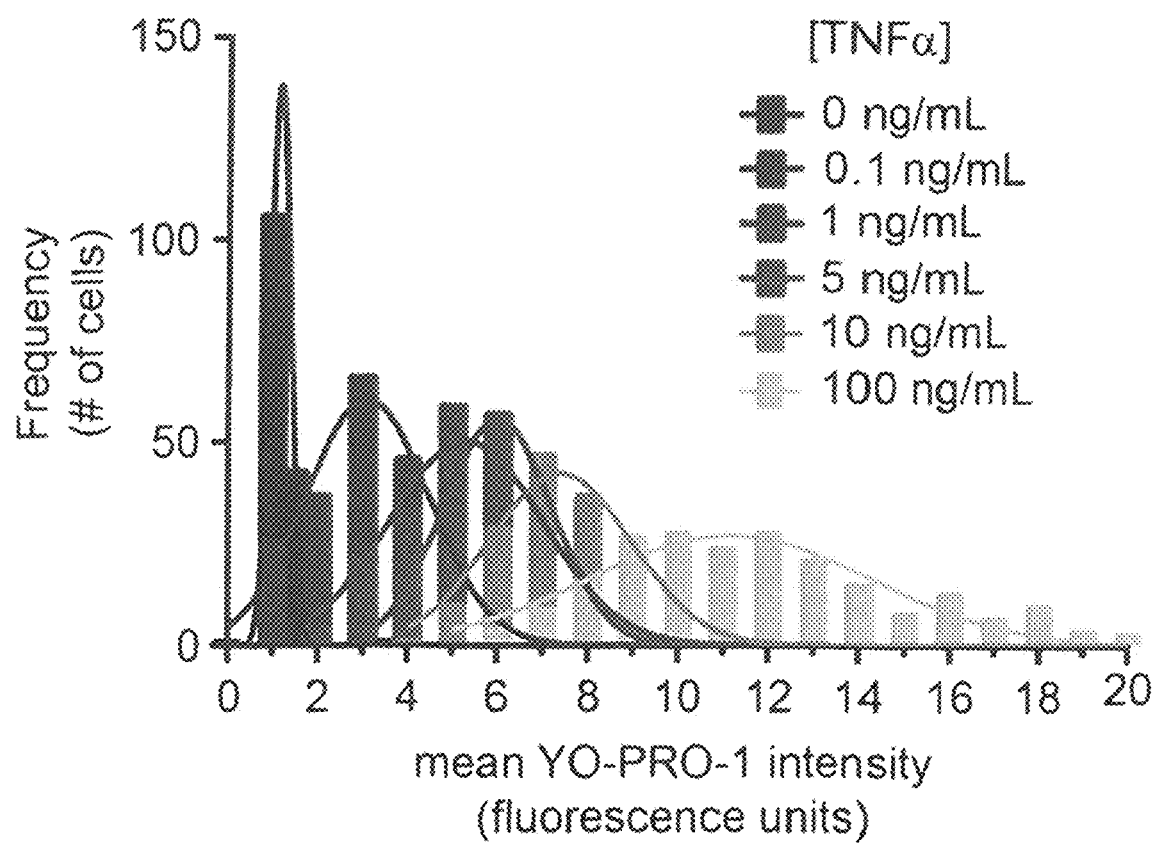

FIG. 9: TNFα-induced YO-PRO-1 dye uptake by Panx1 channels in HUVEC (a) YO-PRO-1 (1 μM) dye uptake by HUVEC stimulated with increasing concentrations of recombinant human TNFα for 30 minutes.=p<0.01 and *=p<0.005 compared to non-stimulated controls (n=3). (b) Intensity histogram of YO-PRO-1 fluorescence in HUVEC treated with increasing doses of TNFα. (c) Inhibition of YO-PRO-1 uptake by the Panx1 blocker $^{10}$panx1 (200 μM). HUVEC were treated with TNFα (10 ng/mL) for 30 minutes. *=p<0.005 compared to non-stimulated controls and =p<0.01 compared to TNFα treated cells in the absence of [10]panx1 (n=3). (d) Temporal profile of YO-PRO-1 uptake by TNFα stimulated HUVEC. Cells were treated with TNFα (10 ng/mL) and YO-PRO-1 was added at various time points following TNFα application. All cells were fixed and imaged 30 minutes after TNFα application. All data are presented as mean±SEM (error bars). Statistical analyses were performed using One-way ANOVA.

Figure 10:
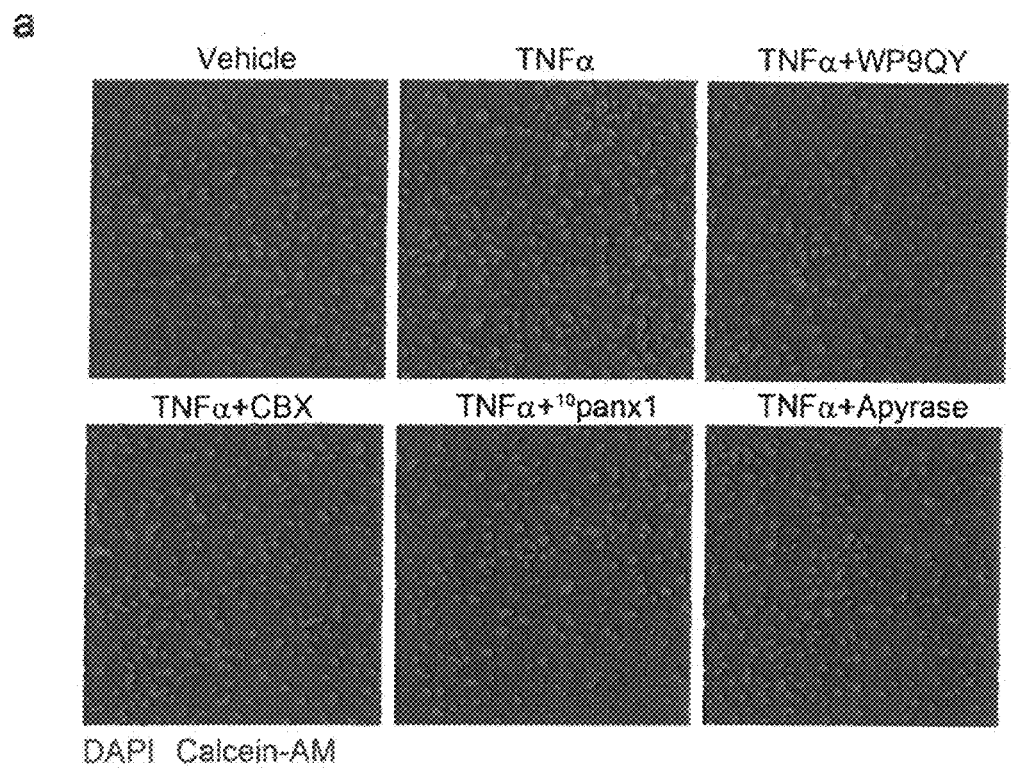
Figure 10:
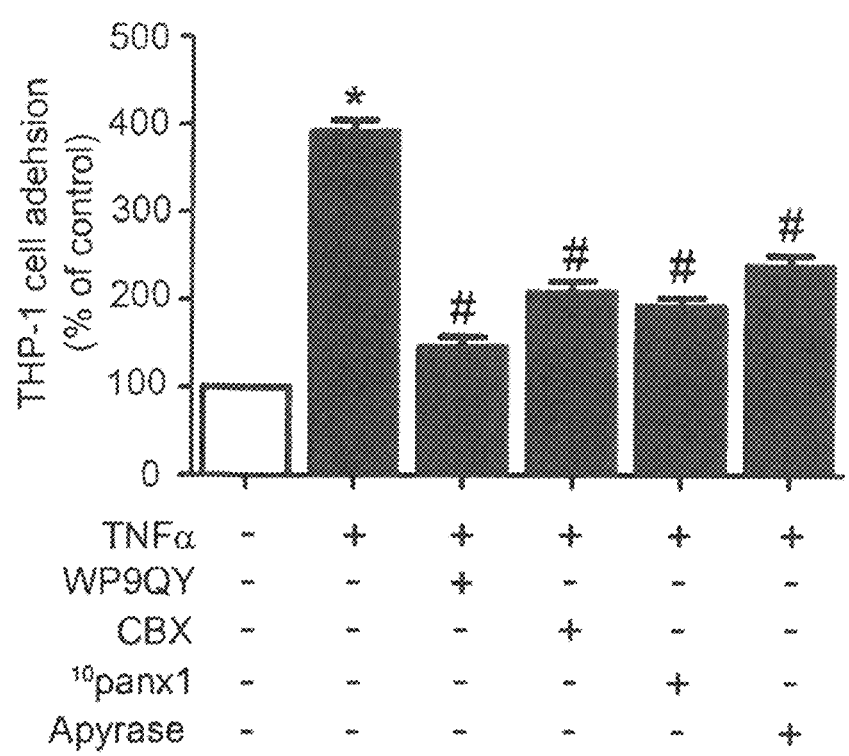

FIG. 10: Panx1 activation promotes THP-1 monocyte adhesion to cultured ECs (a) THP-1 monocyte adhesion assay on TNFα-stimulated HUVEC. HUVEC nuclei are stained with DAPI in blue and adherent calcein-AM loaded THP-1 monocytes are in green. (b) Quantification of TNFα-induced monocyte adhesion in HUVEC treated with WP9QY, CBX, [10]panx1, or Apyrase prior to TNFα stimulation. *=p<0.01 compared to vehicle treated cells and #=p<0.01 as compared to TNFα treated cells in the absence of inhibitors by One-way ANOVA (n=5). All data are presented as mean±SEM (error bars).

FIG. 11: Tamoxifen does not affect leukocyte interactions with venous ECs in C57B1/6J mice (a) Intravital microscopy analysis of the absolute number of rolling leukocytes, post-capillary venule diameter and wall shear rate in C57 and VECadER$^{T2+}$/Panx1$^{fl/fl}$ mice during TNFα-induced leukocyte adhesion and emigration. (b-c) Intravital microscopy analysis of adhesion (b) and emigration (c) in C57B1/6J (C57) mice injected with tamoxifen (Tam) for 10 consecutive days. Topical application of TNFα to the exteriorized cremaster muscle resulted in a time dependent increase in leukocyte adhesion to post-capillary venules (#/mm$^2$ vessel wall) and emigration into the interstitium (#/mm$^2$ interstitium) in Tam injected C57 mice. *=p<0.01 as compared to C57+Vehicle by One-way ANOVA (n=5). All data are presented as mean±SEM (error bars).

Figure 12:
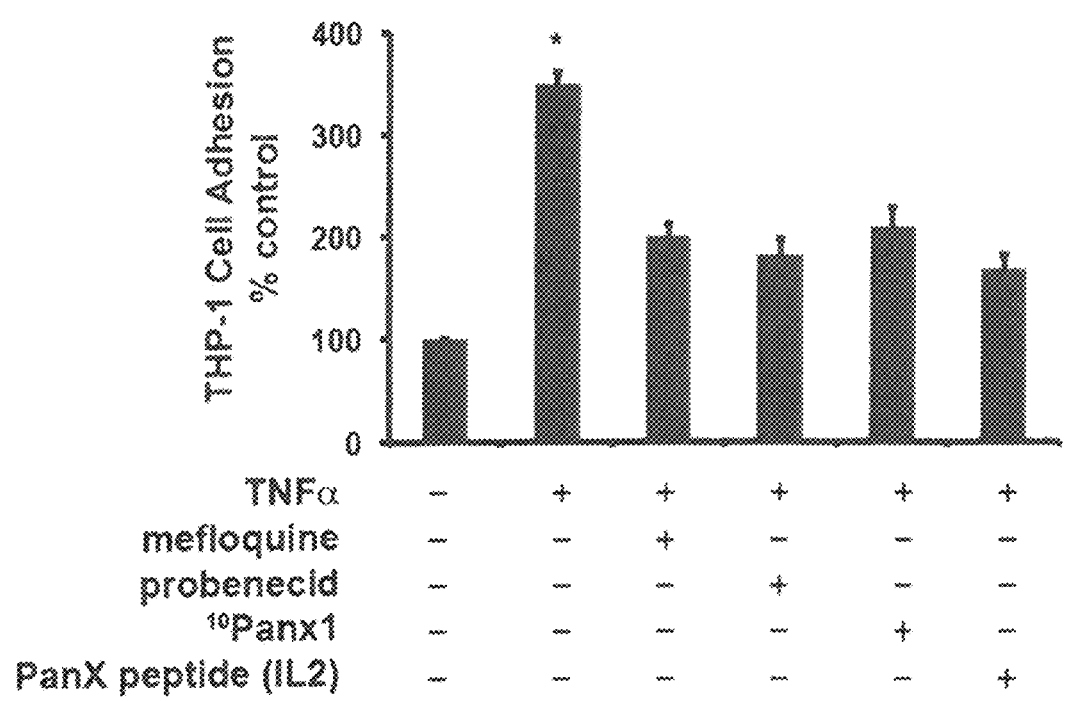

FIG. 12: Effect of IL2 (PanX peptide), derived against the Y198 intracellular loop of Pannexin1, on THP-1 Cell Adhesion. The first four conditions in the graph (TNFα, mefloquine, probenecid, and [10]Panx1) are reproduced data from FIG. 10; however, this is now in comparison to the fifth condition on the graph, the IL2 mimic peptide (PanX/IL2). These data disclose that the IL2/PanX peptide has the ability to block leukocyte adhesion.

DETAILED DESCRIPTION

Abbreviations and Acronyms
   5HT—serotonin
   [10]Panx1—Panx1 inhibitory peptide (WRQAAFVDSY: SEQ ID NO: 8)
   α1AR—alphal-adrenoreceptor
   AM—acute kidney injury
   ATP—adenosine 5' triphosphate
   CBX—carbenoxolone
   CT—C terminal
   Cx—connexins
   EC—endothelial cell
   ET-1—endothelin 1
   GPCR—G protein-coupled receptors
   HAo—human aortic
   HCoA—human coronary artery
   HEK—human embryonic kidney
   HSaV—human saphenous vein
   HUVEC—human umbilical vein endothelial cell
   KO—knockout
   KOMP—knockout mouse project
   IEL—internal elastic lamina
   IL—intracellular loop
   IL-1β—interleukin-1beta
   IL2—intracellular loop two protein plus a TAT sequence, also referred to as UVAPx-1 and as PanX
   IRI—ischemic reperfusion injury
   iSEM—Immuno-scanning electron micrographs
   MAP—mean arterial pressure
   NMDA—N-methyl-D-aspartate
   Panx1—pannexin 1
   PAR—protease activated receptor
   PE—phenylephrine
   PKA—cyclic AMP-dependent protein kinase
   PKC—protein kinase C
   SMC—smooth muscle cell
   SFK—Src family kinase
   TDA—thoracodorsal artery
   TNFα—tumor necrosis factor alpha
   TNFR1—TNF receptor type I
Definitions In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element or "a protein" means more than one protein.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

As used herein the term, "accurate mass" refers to an experimentally or theoretically determined mass of an ion that is used to determine an elemental formula. For ions containing combinations of the elements C, H, N, O, P, S, and the halogens, with mass less than 200 Unified Atomic Mass Units, a measurement about 5 ppm uncertainty is sufficient to uniquely determine the elemental composition.

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As used herein, the term "adjuvant" refers to a substance that elicits an enhanced immune response when used in combination with a specific antigen.

As use herein, the terms "administration of" and or "administering" a compound should be understood to mean providing a compound of the invention or a prodrug of a compound of the invention to a subject in need of treatment.

As used herein, the term "aerosol" refers to suspension in the air. In particular, aerosol refers to the particlization or atomization of a formulation of the invention and its suspension in the air.

As used herein, an "agonist" is a composition of matter which, when administered to a mammal such as a human, enhances or extends a biological activity attributable to the level or presence of a target compound or molecule of interest in the mammal.

As used herein, "alleviating a disease or disorder symptom," means reducing the severity of the symptom or the frequency with which such a symptom is experienced by a patient, or both.

As used herein, amino acids are represented by the full name thereof, by the three-letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

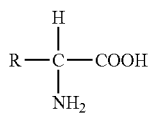

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino-and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

An "antagonist" is a composition of matter which when administered to a mammal such as a human, inhibits a biological activity attributable to the level or presence of a compound or molecule of interest in the mammal.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)2, as well as single chain antibodies and humanized antibodies.

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antigenic determinant" as used herein refers to that portion of an antigen that makes contact with a particular antibody (i.e., an epitope). When a protein or fragment of a protein, or chemical moiety is used to immunize a host animal, numerous regions of the antigen may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

An "aptamer" is a compound that is selected in vitro to bind preferentially to another compound (for example, the identified proteins herein). Often, aptamers are nucleic acids or peptides because random sequences can be readily generated from nucleotides or amino acids (both naturally occurring or synthetically made) in large numbers but of course they need not be limited to these.

The term "associated with ischemia" as used herein means that an injury, disease, or disorder that is being treated or which is being prevented either develops as a result of ischemia or ischemia develops as a result of the injury disease or disorder, i.e., the two are closely linked.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biocompatible", as used herein, refers to a material that does not elicit a substantial detrimental response in the host.

The term "biological sample," as used herein, refers to samples obtained from a subject, including, but not limited to, skin, hair, tissue, blood, plasma, cells, sweat and urine.

As used herein, the term "biologically active fragments" or "bioactive fragment" of the polypeptides encompasses natural or synthetic portions of the full-length protein that are capable of specific binding to their natural ligand or of performing the function of the protein.

As used herein, the term "carrier molecule" refers to any molecule that is chemically conjugated to the antigen of interest that enables an immune response resulting in antibodies specific to the native antigen.

The term "cell surface protein" means a protein found where at least part of the protein is exposed at the outer aspect of the cell membrane. Examples include growth factor receptors.

A "chaotropic agent" is a substance which disrupts the structure of, and denatures, macromolecules such as proteins and nucleic acids (e.g. DNA and RNA). Chaotropic solutes increase the entropy of the system by interfering with intramolecular interactions mediated by non-covalent forces such as hydrogen bonds, van der Waals forces, and hydrophobic effects. Macromolecular structure and function is dependent on the net effect of these forces (see protein folding), therefore it follows that an increase in chaotropic solutes in a biological system will denature macromolecules, reduce enzymatic activity and induce stress on a cell (i.e., a cell will have to synthesize stress protectants). Tertiary protein folding is dependent on hydrophobic forces from amino acids throughout the sequence of the protein. Chaotropic solutes decrease the net hydrophobic effect of hydrophobic regions because of a disordering of water molecules adjacent to the protein. This solubilizes the hydrophobic region in the solution, thereby denaturing the protein. This is also directly applicable to the hydrophobic region in lipid bilayers; if a critical concentration of a chaotropic solute is reached (in the hydrophobic region of the bilayer) then membrane integrity will be compromised, and the cell will lyse. Chaotropic salts that dissociate in solution exert chaotropic effects via different mechanisms. Whereas chaotropic compounds such as ethanol interfere with non-covalent intramolecular forces as outlined above, salts can have chaotropic properties by shielding charges and preventing the stabilization of salt bridges. Hydrogen bonding is stronger in non-polar media, so salts, which increase the chemical polarity of the solvent, can also destabilize hydrogen bonding. Mechanistically this is because there are insufficient water molecules to effectively solvate the ions. This can result in ion-dipole interactions between the salts and hydrogen bonding species which are more favorable than normal hydrogen bonds. Chaotropic agents include butanol, ethanol, guanidinium chloride, lithium perchlorate, lithium acetate, magnesium chloride, phenol, propanol, sodium dodecyl sulfate, thiourea and urea.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

A "compound," as used herein, refers to any type of substance or agent that is commonly considered a drug, or a candidate for use as a drug, as well as combinations and mixtures of the above.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets, and effector activities of these cytokines have been described.

As used herein, a "derivative" of a compound, when referring to a chemical compound, is one that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, the term "diagnosis" refers to detecting a disease, disorder or condition using a marker disclosed herein. In any method of diagnosis exist false positives and false negatives. Any one method of diagnosis does not provide 100% accuracy.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains. As used herein, the term "effector domain" refers to a domain capable of directly interacting with an effector molecule, chemical, or structure in the cytoplasm which is capable of regulating a biochemical pathway.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

The term "elixir," as used herein, refers in general to a clear, sweetened, alcohol-containing, usually hydroalcoholic liquid containing flavoring substances and sometimes active medicinal agents.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

By "equivalent fragment" as used herein when referring to two homologous proteins from different species is meant a fragment comprising the domain or amino acid being described or compared relative to the first protein.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 2-15 amino acids in length, at least about 15-25 amino acids, at least about 25-50 amino acids in length, at least about 50-75 amino acids in length, at least about 75-100 amino acids in length, and greater than 100 amino acids in length, depending on the particular protein or peptide being referred to.

As used herein, a "functional" molecule is a molecule in a form in which it exhibits a property or activity by which it is characterized. A functional enzyme, for example, is one that exhibits the characteristic catalytic activity by which the enzyme is characterized.

"Highly chaotropic environment" refers the concentration of a chaotropic agent in a solution. In certain embodiments, the concentration is exactly, about or at least, 1, 2, 3, 4, 5, 6, 7, 8, 9, 10, or more molar. In a particular embodiment it refers to about or at least 6, 7, 8 or 9 molar urea.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCCS' and 3'TATGGC share 50% homology.

As used herein, "homology" is used synonymously with "identity." The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used. The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

As used herein, the term "hydrolyzing agent" refers to any one or combination of a large number of different enzymes, including but not limited to trypsin, Lysine-C endopeptidase (LysC), arginine-C endopeptidase (ArgC), Asp-N, glutamic acid endopeptidase (GluC) and chymotrypsin, V8 protease and the like, as well as chemicals, such as cyanogen bromide. In the subject invention one or a combination of hydrolyzing agents cleave peptide bonds in a protein or polypeptide, in a sequence-specific manner, generating a predictable collection of shorter peptides (a "digest"). A portion of the biological samples are contacted with hydrolyzing agent(s) to form a digest of the biological sample. Given that the amino acid sequences of certain polypeptides and proteins in biological samples are often known and that the hydrolyzing agent(s) cuts in a sequence-specific manner, the shorter peptides in the digest are generally of a predicable amino acid sequence.

"Infection to be treated" as used herein refers to any infection from bacteria, viruses, etc. where inflammation ensues and the inflammation can be treated using a peptide or other inhibitor of the invention within the context of the regulation of Panx1 activity as described herein.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein," as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time. This also includes "inhibiting Pannexin1".

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the compositions and apparatuses of the invention in the kit. The instructional material of the kit of the invention may, for example, be affixed to a container which contains the identified compound(s) invention or be shipped together with a container which contains the identified compound. Alternatively, the instructional material may be shipped separately from the container with the intention that the instructional material and the compound be used cooperatively by the recipient.

The term "ischemia" as used herein refers to a local anemia due to mechanical obstruction of the blood supply, which gives rise to inadequate circulation of the blood to an organ, tissue, or region of an organ or tissue.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

A "ligand" is a compound that specifically binds to a target receptor.

A "receptor" is a compound that specifically binds to a ligand.

A ligand or a receptor (e.g., an antibody) "specifically binds to" or "is specifically immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988, Antibodies, A Laboratory Manual, Cold Spring Harbor Publications, New York) for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

"Liquid chromatography-mass spectrometry (LC-MS, or alternatively HPLC-MS)" is an analytical chemistry technique that combines the physical separation capabilities of liquid chromatography (or HPLC) with the mass analysis capabilities of mass spectrometry (MS). Liquid chromatography generally utilizes very small particles packed and operating at relatively high pressure, and is referred to as high performance liquid chromatography (HPLC). LC-MS methods use HPLC instrumentation for sample introduction. In HPLC, the sample is forced by a liquid at high pressure (the mobile phase) through a column that is packed with a stationary phase generally composed of irregularly or spherically shaped particles chosen or derivatized to accomplish particular types of separations. HPLC methods are historically divided into two different sub-classes based on stationary phases and the corresponding required polarity of the mobile phase. Use of octadecylsilyl (C18) and related organic-modified particles as stationary phase with pure or pH-adjusted water-organic mixtures such as water-acetonitrile and water-methanol are used in techniques termed reversed phase liquid chromatography (RP-LC). Use of materials such as silica gel as stationary phase with neat or mixed organic mixtures are used in techniques termed normal phase liquid chromatography (NP-LC).

"Malexpression" of a gene means expression of a gene in a cell of a patient afflicted with a disease or disorder, wherein the level of expression (including non-expression), the portion of the gene expressed, or the timing of the expression of the gene with regard to the cell cycle, differs from expression of the same gene in a cell of a patient not afflicted with the disease or disorder. It is understood that malexpression may cause or contribute to the disease or disorder, be a symptom of the disease or disorder, or both.

The term "mass spectrometer" means a device capable of detecting specific molecular species and measuring their accurate masses. The term is meant to include any molecular detector into which a polypeptide or peptide may be eluted for detection and/or characterization. In the preferred MS procedure, a sample, e.g., the elution solution, is loaded onto the MS instrument, and undergoes vaporization. The components of the sample are ionized by one of a variety of methods (e.g., by electrospray ionization or "ESI"), which results in the formation of positively charged particles (ions). The positive ions are then accelerated by a magnetic field. The computation of the mass-to-charge ratio of the particles is based on the details of motion of the ions as they transit through electromagnetic fields, and detection of the ions. In one aspect, the mass measurement error of a mass spectrometer of the invention is about 10 ppm or less, in another it is about 7 ppm or less, and in yet another it is about 5 ppm or less. Fragment ions in the MS/MS and MS3 spectra are generally highly specific for peptides of interest.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

The term "nasal administration" in all its grammatical forms refers to administration of at least one compound of the invention through the nasal mucous membrane to the bloodstream for systemic delivery of at least one compound of the invention. The advantages of nasal administration for delivery are that it does not require injection using a syringe and needle, it avoids necrosis that can accompany intramuscular administration of drugs, and trans-mucosal administration of a drug is highly amenable to self-administration.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

The term "per application" as used herein refers to administration of a compositions, drug, or compound to a subject.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Pharmaceutically acceptable" means physiologically tolerable, for either human or veterinary application.

As used herein, "pharmaceutical compositions" include formulations for human and veterinary use.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

By "presensitization" is meant pre-administration of at least one innate immune system stimulator prior to challenge with an agent. This is sometimes referred to as induction of tolerance.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

A "prophylactic" treatment is a treatment administered to a subject who does not exhibit signs of a disease or exhibits only early signs of the disease for the purpose of decreasing the risk of developing pathology associated with the disease.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., The Peptides, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

A "recombinant cell" is a cell that comprises a transgene. Such a cell may be a eukaryotic or a prokaryotic cell. Also, the transgenic cell encompasses, but is not limited to, an embryonic stem cell comprising the transgene, a cell obtained from a chimeric mammal derived from a transgenic embryonic stem cell where the cell comprises the transgene, a cell obtained from a transgenic mammal, or fetal or placental tissue thereof, and a prokaryotic cell comprising the transgene.

The term "regulate" refers to either stimulating or inhibiting a function or activity of interest.

"Regulated by TNFα" means affected directly or indirectly by the activity or function of TNFα, and/or by its signal transduction pathway.

As used herein, the term "reporter gene" means a gene, the expression of which can be detected using a known method. By way of example, the Escherichia coli lacZ gene may be used as a reporter gene in a medium because expression of the lacZ gene can be detected using known methods by adding the chromogenic substrate o-nitrophenyl-β-galactoside to the medium (Gerhardt et al., eds., 1994, *Methods for General and Molecular Bacteriology*, American Society for Microbiology, Washington, DC, p. 574).

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture. By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, a standard can be a known standard agent or compound which is administered or added to a control sample and used for comparing results when measuring said compound in a test sample. In one aspect, the standard compound is added or prepared at an amount or concentration that is equivalent to a normal value for that compound in a normal subject. Standard can also refer to an "internal standard," such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, a "subject in need thereof" is a patient, animal, mammal, or human, who will benefit from the method of this invention.

As used herein, a "substantially homologous amino acid sequence" includes those amino acid sequences which have at least about 95% homology, preferably at least about 96% homology, more preferably at least about 97% homology, even more preferably at least about 98% homology, and most preferably at least about 99% homology to an amino acid sequence of a reference sequence. Amino acid sequences similarity or identity can be computed using, for example, the BLASTP and TBLASTN programs which employ the BLAST (basic local alignment search tool) algorithm. The default setting used for these programs are suitable for identifying substantially similar amino acid sequences for purposes of the present invention.

"Substantially identical" when referring to a subject protein or polypeptide relative to a reference protein or polypeptide (e.g., an enzyme such as aspergillopepsin I or a enzymatically active fragment thereof) means that the subject is either exactly, at least or about 99.9, 99.5, 99, 98, 97, 96, 95, 94, 93, 92, 91, 90, 89, 88, 87, 86, 85, 84, 83, 82, 81, 80, 75, 70, 65 or 60 percent identical in terms of amino acid sequence relative to the reference.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "transgene" means an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, the term "transgenic mammal" means a mammal, the germ cells of which comprise an exogenous nucleic acid.

As used herein, a "transgenic cell" is any cell that comprises a nucleic acid sequence that has been introduced into the cell in a manner that allows expression of a gene encoded by the introduced nucleic acid sequence.

The term to "treat," as used herein, means reducing the frequency with which symptoms are experienced by a patient or subject or administering an agent or compound to reduce the frequency with which symptoms are experienced.

A "prophylactic" treatment is a treatment administered to a subject who does not exhibit signs of a disease or exhibits only early signs of the disease for the purpose of decreasing the risk of developing pathology associated with the disease.

By the term "vaccine," as used herein, is meant a composition which when inoculated into a subject has the effect of stimulating an immune response in the subject, which serves to fully or partially protect the subject against a condition, disease or its symptoms. In one aspect, the condition is conception. The term vaccine encompasses prophylactic as well as therapeutic vaccines. A combination vaccine is one which combines two or more vaccines, or two or more compounds or agents.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Embodiments

The present invention provides compositions and methods for treating injuries, diseases, disorders, and conditions where inflammation ensues or the inflammation exacerbates the problem. In one aspect, the diseases and disorders are autoimmune. In one aspect, inflammation is associated with the disease or disorder being treated. In one aspect, the invention provides compositions and methods useful for treating a disease or disorder including, but not limited to, diabetic nephropathy, pancreatitis, type 1 diabetes, type 2 diabetes, insulitis, lupus, lupus glomerulonephritis, obesity, acute kidney injury, renal ischemia reperfusion injury, multiple sclerosis, diabetic retinopathy, ankylosing spondylitis, autoimmune cardiomyopathy, autoimmune hemolytic anemia, autoimmune hepatitis, autoimmune lymphoproliferative syndrome, autoimmune pancreatitis, autoimmune polyendocrine syndrome, autoimmune urticaria, autoimmune uveitis, Crohn's disease, dermatomyositis, graft versus host (GVH) disease, Hashimoto's thyroiditis, inflammatory demyelinating diseases, interstitial cystitis, juvenile idiopathic arthritis aka Juvenile rheumatoid arthritis, lupus erythematosus, multiple sclerosis, myasthenia gravis, microscopic colitis, polymyositis, primary biliary cirrhosis, primary sclerosing cholangitis, progressive inflammatory neuropathy, rheumatoid arthritis, Sjögren's syndrome, systemic lupus erythematosus, transplant rejection, ulcerative colitis (one of two types of idiopathic inflammatory bowel disease "IBD"), vasculitis, and Wegener's granulomatosis. In one aspect, the method treats inflammation associated with injuries, diseases, disorders, and conditions of the invention.

There are important clinical and commercial implications of the invention disclosed herein. Pannexin1 channels have been implicated in a number of diseases and disorders. IL2 peptide (SEQ ID NO: 3; also referred to as UVAPx-1) is an effective and targeted peptide inhibitor that could have a significant impact as a biomedical research tool for studying the role of pannexins in diseases associated with hypertension, autoimmunity, inflammation, ischemia, stroke, and cancer. Due to the beneficial pharmacological properties of small peptide inhibitors IL2 (UVAPx-1) has high clinical potential as an innovative pharmacotherapy for pathologies pertaining to essential hypertension, treatment resistant hypertension, vascular sympathetic nerve hyperactivity, vascular dysfunction, stroke, aberrant immune cell recruitment from the blood into body tissues, and pathological TNF-alpha dependent inflammatory responses.

In one embodiment, the invention provides compositions and methods useful for preventing or treating a disease or disorder of the invention. In one aspect, the method prevents or treats type 1 diabetes, renal ischemia reperfusion injury, or lupus glomerulonephritis.

Multiple techniques for measuring proteins and peptides are known in the art or described herein and can use in the practice of the invention. These include, but are not limited to, for example:

Electrochemiluminescent immunoassay;

Bioluminsescent Immunoassay (for example, with use of apoaequorin and oelenterazine);

Luminescent oxygen channeling immunoassay (LOCI);

The Erenna Immunoassay System (a modified microparticle-based sandwich immunoassay with single-molecule counting);

Nanoparticle Immunoassay: nano-particles, spheres, or tubes as solid phases
    upconverting phosphor nanoparticle using antiStokes shift
    quantum dot immunoassay (Heterogeneous immunoassay in which a nanometer-sized (less than 10 nm) semiconductor quantum dot is used as a label.

A quantum dot is a highly fluorescent nanocrystal composed of CdSe, CdS, ZnSe, InP, or InAs or a layer of ZnS or CdS on, for example, a CdSe core);

Fluorescence Excitation Transfer Immunoassay;

ImmunoPCR Immunoassay;

Solid Phase, Light-Scattering Immunoassay: Indium spheres are coated on glass to measure an antibody binding to an antigen. Binding of antibodies to antigens increases dielectric layer thickness, which produces a greater degree of scatter than in areas where only an antigen is bound. Quantitation is achieved by densitometry; and Surface Effect Immunoassay: with antibody immobilized on the surface of a waveguide (a quartz, glass, or plastic slide, or a gold- or silver-coated prism), and binding of antigen measured directly by total internal reflection fluorescence, surface plasmon resonance, or attenuated total reflection.

In one aspect, an antibody or a fragment or homolog thereof of the invention can be conjugated to an imaging agent. In one embodiment, antibody complex comprises an imaging agent selected from the group consisting of a radionuclide, a radiological contrast agent, a paramagnetic ion, a metal, a biological tag, a fluorescent label, a chemiluminescent label, an ultrasound contrast agent and a photoactive agent. In one aspect, the imaging agent is a radionuclide. In one aspect, the radionuclide is selected from the group consisting of $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82}$mRb, $^{83}$Sr, and other gamma-, beta-, or positron-emitters. In one aspect, the radionuclide is $^{111}$In.

The invention further provides for use of the monoclonal antibodies described herein for drug delivery and for diagnostics. For example, various agents as described herein can be conjugated to the antibodies. Peptides such as SEQ ID NOs:3 and 8, and radionuclides such as beta $^{90}$Y, gamma $^{131}$I, and positron $^{124}$I emitters can be conjugated to monoclonal antibodies directed against human pannexin1 and used to image inflammation and used as radiotherapeutic and therapeutic agents for treatment.

It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones, or amides. Ester or ketone-forming alkyl groups, particularly lower alkyl groups such as methyl, ethyl and propyl, and amide-forming amino groups such as primary amines (-NH2), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

The peptides of the present invention may be readily prepared by standard, well-established techniques, such as solid-phase peptide synthesis (SPPS) as described by Stewart et al. in Solid Phase Peptide Synthesis, 2nd Edition, 1984, Pierce Chemical Company, Rockford, Illinois; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions that will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method that utilized tert-butyloxcarbonyl as the α-amino protecting group, and the FMOC method which utilizes 9-fluorenylmethyloxcarbonyl to protect the α-amino of the amino acid residues, both methods of which are well-known by those of skill in the art.

To ensure that the proteins or peptides obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide can be purified to remove contaminants. In this regard, it will be appreciated that the peptide will be purified to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure peptide obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, Guide to Protein Purification, Harcourt Brace Jovanovich, San Diego).

Pharmaceutical Compositions and Administration

The present invention is also directed to pharmaceutical compositions comprising the compounds of the present invention. More particularly, such compounds can be formulated as pharmaceutical compositions using standard pharmaceutically acceptable carriers, fillers, solublizing agents and stabilizers known to those skilled in the art.

The invention is also directed to methods of administering the compounds of the invention to a subject. In one embodiment, the invention provides a method of treating a subject by administering compounds identified using the methods of the invention description. Pharmaceutical compositions comprising the present compounds are administered to a subject in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

In accordance with one embodiment, a method of treating a subject in need of such treatment is provided. The method comprises administering a pharmaceutical composition comprising at least one compound of the present invention to a subject in need thereof. Compounds identified by the methods of the invention can be administered with known compounds or other medications as well.

The invention also encompasses the use of pharmaceutical compositions of an appropriate compound, and homologs, fragments, analogs, or derivatives thereof to practice the methods of the invention, the composition comprising at least one appropriate compound, and homolog, fragment, analog, or derivative thereof and a pharmaceutically-acceptable carrier.

The pharmaceutical compositions useful for practicing the invention may, in one aspect, be administered to deliver a dose of between 1 ng/kg/day and 1,000 mg/kg/day.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

It will be understood by the skilled artisan that such pharmaceutical compositions are generally suitable for administration to animals of all sorts. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys. The invention is also contemplated for use in contraception for nuisance animals such as rodents.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically, dosages of the compound of the invention which may be administered to an animal, preferably a human, range in amount from 1 µg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the condition or disease being treated, the type and age of the animal, etc.

Suitable preparations of vaccines include injectables, either as liquid solutions or suspensions, however, solid forms suitable for solution in, suspension in, liquid prior to injection, may also be prepared. The preparation may also be emulsified, or the polypeptides encapsulated in liposomes. The active immunogenic ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants which enhance the effectiveness of the vaccine.

The invention is also directed to methods of administering the compounds of the invention to a subject. In one embodiment, the invention provides a method of treating a subject by administering compounds identified using the methods of the invention. Pharmaceutical compositions comprising the present compounds are administered to an individual in need thereof by any number of routes including, but not limited to, topical, oral, intravenous, intramuscular, intra arterial, intramedullary, intrathecal, intraventricular, transdermal, subcutaneous, intraperitoneal, intranasal, enteral, topical, sublingual, or rectal means.

Peptide Modification and Preparation

Peptide preparation is described in the Examples. It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (-NH2), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamic, mandelic, methanesulfonic, ethanesulfonic, p-toluenesulfonic, salicyclic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring or non-standard synthetic amino acids. The peptides of the invention are not limited to products of any of the specific exemplary processes listed herein.

The invention includes the use of beta-alanine (also referred to as β-alanine, β-Ala, bA, and βA, having the structure:

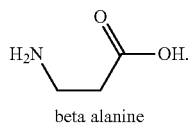

beta alanine

Sequences are provided herein which use the symbol "βA", but in the Sequence Listing submitted herewith "βA" is provided as "Xaa" and reference in the text of the Sequence Listing indicates that Xaa is beta alanine.

Peptides useful in the present invention, such as standards, or modifications for analysis, may be readily prepared by standard, well-established techniques, such as solid-phase peptide synthesis (SPPS) as described by Stewart et al. in *Solid Phase Peptide Synthesis,* 2nd Edition, 1984, Pierce Chemical Company, Rockford, Ill.; and as described by Bodanszky and Bodanszky in *The Practice of Peptide Synthesis,* 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxycarbonyl as the α-amino protecting group, and the FMOC method which utilizes 9-fluorenylmethyloxycarbonyl to protect the α-amino of the amino acid residues, both methods of which are well-known by those of skill in the art.

Incorporation of N- and/or C- blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxy-alkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide may be purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high performance liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

As discussed, modifications or optimizations of peptide ligands of the invention are within the scope of the application. Modified or optimized peptides are included within the definition of peptide binding ligand. Specifically, a peptide sequence identified can be modified to optimize its potency, pharmacokinetic behavior, stability and/or other biological, physical and chemical properties.

Amino Acid Substitutions

In certain embodiments, the disclosed methods and compositions may involve preparing peptides with one or more substituted amino acid residues.

In various embodiments, the structural, physical and/or therapeutic characteristics of peptide sequences may be optimized by replacing one or more amino acid residues.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art. For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-,3- or 4-aminophenylalanine, 2-,3- or 4-chlorophenylalanine, 2-,3- or 4-methylphenylalanine, 2-,3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2',-3',- or 4'-methyl-2, 3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopropionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2 is preferred, within +/−1 are more preferred, and within +/−0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5. +-0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

The invention also includes a kit comprising the composition of the invention and an instructional material which describes adventitially administering the composition to a cell or a tissue of a mammal. In another embodiment, this kit comprises a (preferably sterile) solvent suitable for dissolving or suspending the composition of the invention prior to administering the compound to the mammal.

EXAMPLES

Most of the studies described below and as recited in the provisional application from which this application depends are now published as Lohman, A. W. et al., Pannexin 1 channels regulate leukocyte emigration through the venous endothelium during acute inflammation. Nat. Commun. 6:7965 doi: 10.1038/ncomms8965 (2015) (epublished Aug. 5, 2015).

Methods

Cell Culture

Primary human umbilical vein endothelial cells (HUVEC) were purchased from Cell Applications (200K-05). Primary human saphenous vein (HSaVEC) and human aortic (HAoEC) were from PromoCell (C-12231 and C-12271, respectively) and human coronary artery endothelial cells (HCoAEC) were purchased from Lonza (CC-2585). All ECs were maintained under standard cell culture conditions in endothelial growth medium (EGM-2MV) from Lonza. For siRNA knockdown of Panx1 and Cx43, HUVEC and HSaVECs were plated in 6-well (expression) or 24-well plates (ATP release) and grown to 70-80% confluence. Non-targeting siRNAs (Life Technologies silencer select negative control 1, 4390843) or siRNAs targeting the human PANX1 gene (Life Technologies Panx1 silencer select 4392420-s24427) or Cx43 (Life Technologies GJA1 silencer select 4392420-s5758) were transfected into ECs using Lipofectamine RNAiMAX reagent and knockdown was assessed via Western blotting following a 72 hour incubation.

Mice

All mice were male, 10-14 weeks of age, on a C57B$^1$/$_6$J genetic background, and were cared for under the provisions of the University of Virginia Animal Care and Use Committee and the LSU Health Sciences Center-Shreveport Animal Care and Use Committee and followed the National Institute of Health guidelines for the care and use of laboratory animals. The inducible, endothelial cell-specific Panx1 knockout mice (VECadER$^{T2+}$/Panx1$^{fl/fl}$) were generated by crossing VECadER$^{T2+}$/Panx1$^{WT/WT}$ mice (a kind gift from Dr. Ralf Adams, Max Plank Institute, Germany) with VECadER$^{T2-}$/Panx1$^{fl/fl}$ mice[23]. To selectively induce Panx1 deletion in the vascular endothelium, VECadER$^{T2+}$/Panx1$^{fl/fl}$ mice received intraperitoneal injections of Tamoxifen (1 mg in 0.1 mL Peanut Oil) for 10 consecutive days. A subset of VECadER$^{T2+}$/Panx1$^{fl/fl}$ mice were injected with peanut oil (the vehicle for tamoxifen) and served as littermate controls.

ATP Release Assays

In vitro Human arterial and venous ECs were seeded in 24-well plates pre-coated with 0.2% gelatin and grown to confluency. On the day of experiment, the media was removed from each well and cells were carefully washed twice with warm serum free basal EC medium supplemented with 1% BSA. Cells were then incubated in 300 µL of fresh basal EC medium supplemented with 1% BSA for 30 minutes at 37° C. to allow degradation of extracellular ATP released due to mechanical stimulation during washes. Endogenous ecto-nucleotidases were inhibited by incubating EC monolayers with 300 µM ARL 67156 (Tocris) for 30 minutes at 37° C. Cells were then stimulated with recombinant human TNFα (R&D Systems). For dose response experiments, ECs were incubated with 0.1, 1, 5, 10, 50, or 100 ng/mL recombinant TNFα for 30 minutes at 37° C. For time-course experiments, ECs were stimulated with 10 ng/mL recombinant TNFα for different time points up to 1 hour. In experiments where pharmacological inhibitors were employed, ECs were incubated with antagonists in parallel with ARL 67156 for 30 minutes. To inhibit TNFR1, ECs were incubated with the peptide antagonist of the receptor WP9QY (10 µM; Anaspec). Vesicular ATP release was inhibited with brefeldin A (BFA; 5 µg/mL; Sigma) and CALHM1 channels were pharmacologically blocked with ruthenium red (RuR; 20 µM; Sigma). Cx hemichannels were inhibited with lanthanum ($La^{3+}$; 100 µM; Sigma) and Panx1 channels were blocked with carbenoxolone (CBX; 50 µM; Sigma) and the inhibitory peptide $^{10}$panx1 (200 µM; Genscript). To assess the role of Src family kinases (SFK), cells were incubated with the SFK inhibitor PP2 (10 µM; Tocris) or its inactive analog PP3 (10 µM; Tocris). The role of caspase activation was assessed by inhibition with the pan-caspase blocker Q-VD-OPh (100 µM; Sigma). Following stimulation with TNFα or vehicle, 150 µL of the cell supernatant was collected and immediately placed into pre-chilled 1.5 mL Eppendorf tubes on ice. All samples were centrifuged at 10,000×g for 5 minutes and 50 µL of each sample was transferred to a white, opaque 96-well plate. Using a FluoStar Omega luminometer, 50 µL of luciferin:luciferase reagent (ATP bioluminescence assay kit HSII; Roche) was injected into each well and luminescence was recorded following a 5s orbital mix. ATP concentration in each sample was calculated from a standard curve for all experiments. Data are presented as a % change in ATP release from baseline (i.e. unstimulated cells) and expressed as mean±SEM (n=5 independent experiments with triplicate measurements).

Ex Vivo

For isolated blood vessel experiments, 2nd order venules or arterioles were dissected from the mouse mesentery circulation and cannulated on glass micropipettes to access the vessel lumen. Following cannulation, vessels were perfused lumenally with a MOPS buffered physiological salt solution (NaCl 145 mM, KCl 4.7 mM, $CaCl_2$ 2 mM, $MgSO_4$ 1.17 mM, $NaH_2PO_4$ 1.2 mM, glucose 5 mM, pyruvate 2 mM, EDTA 0.02 mM, MOPS 2 mM) to remove red blood cells and equilibrated at 37° C. for 20 minutes. Vessels were then perfused with MOPS PSS containing 300 µM ARL 67156 +/− pharmacological inhibitors and incubated for an additional 20 minutes prior to perfusion with MOPS PSS containing recombinant murine TNFα (R&D Systems). Aliquots of the lumenal perfusate were collected every 5 minutes for a 25-minute period and the ATP concentration was quantified by bioluminescence as described above. Data are expressed as mean±SEM (n=4 independent experiments).

LDH Release Assays

Isolated mesenteric venules were cannulated and perfused with recombinant mouse TNFα for 20 minutes followed by lysis buffer. Perfusate samples were collected as described above and LDH activity was assayed with the Cytotoxicity Detection Kit Plus (Roche) according to the manufacturer's protocol as an output for cell death. Data are expressed as mean±SEM (n=3 independent experiments).

YO-PRO-1 Dye Uptake Assays

HUVECs were cultured on poly-L-lysine coated coverslips and grown to confluence in EGM. Cells were washed three times with 1× PBS and incubated in fresh EGM for 30 minutes prior to stimulation. To stimulate YO-PRO-1 dye uptake, YO-PRO-1 (1 µM) was added to the media and EC monolayers were treated with TNFα at a range of concentrations (0.1 ng/mL-100 ng/mL) for 30 minutes. At the end of the stimulation, cells were washed 3× with 1× PBS and immediately fixed in 4% PFA. Coverslips were then mounted on microscope slides with DAPI ProlongGold mounting agent and visualized on an Olympus IX81 laser scanning confocal microscope. Dye uptake was quantified as the intensity of YO-PRO-1 fluorescence over time using ImageJ software. For time course analysis, YO-PRO-1 was added to the culture media at various time points after TNFα stimulation and incubated to the 30-minute time point. Data are expressed as mean±SEM (n=3 independent experiments).

Connexin Hemichannel Depletion/Cell Surface Biotinylation

Cell surface biotinylation was performed as described previously[15]. To deplete Cx43 hemichannels from the EC plasma membrane, venous and arterial ECs were grown to confluency in 6-well plates (Western blotting) or 24-well plates (ATP release) and treated with the vesicular exocytosis inhibitor brefeldin A (BFA; 5 µg/mL) for 5 hours at 37° C. Cells were washed once with cold 1× PBS and incubated with cold DMEM (without FBS) and 50 µM CBX at 4° C. for 30 minutes. CBX was added to prevent biotin from passing through Panx1 channels, which may label intracellular proteins. Cells were washed with PBS and incubated at 4° C. for 1 hour in cold PBS (1.5 mL/dish) containing EZ-link-sulfo-NHS-LC-biotin (1 mg/mL) and CBX (50 µM). The cells were washed again with PBS and lysed in PBS-T (PBS+0.5-1% Triton-X 100) containing protease inhibitors. Total protein was quantified using the BCA assay and equal amounts of protein were incubated with Streptavidin-agarose beads for 2 hours at 4° C. to pull down biotinylated (cell surface) proteins. Beads were then washed 5 times with 1× PBS-T, pelleted by centrifugation and proteins eluted by incubation with 5× sample buffer. Eluted proteins were subjected to SDS-PAGE and Western blotting for detection of Cx43 and Panx1.

Immunofluorescence Microscopy

Male VECadER$^{T2+}$/Panx1$^{fl/fl}$ mice (Tamoxifen or Peanut oil injected) were euthanized by $CO_2$ asphyxiation and subsequent cervical dislocation. Prior to tissue harvesting, fixation was performed by perfusing room temperature 4% paraformaldehyde (PFA) made in PBS through the heart. The mesentery was immediately excised and 2nd order venules were dissected free of surrounding fat and connective tissue and place in 4% PFA for 30 minutes before transfer to 70% ethanol for paraffin embedding. Paraffin sections (4-5 µm in thickness) were de-paraffinized and processed for immunocytochemistry as previously described[10]. For validation of Panx1 knockout in the endothelium, vessel sections were processed for conventional immunolabeling and incubated overnight at 4° C. with a primary antibody directed against the murine Panx1 C-tail[24]. To analyze VCAM1 expression, a polyclonal antibody to murine VCAM1 was used (Abcam; 1:500).

Immuno-Transmission Electron Microscopy (iTEM)

This was performed as previously described, using an extracellular loop Panx1 antibody'. Gold beads were pseudo-colored pink for visualization.

Western Blotting for Src-Family Kinase/Panx1 Phosphorylation

Following stimulation with TNFα (in vitro: 10 ng/mL; ex vivo: 50 ng/mL), confluent endothelial cell monolayers or isolated mesenteric venules were homogenized in ice cold Triton extraction buffer (50 mM Tris-HCL, 150 mM NaCl, 5 mM EDTA, 1% deoxycholate, 1% NP-40 and 1% Triton-X100 in phosphate buffered saline and pH adjusted to 7.4) containing protease and phosphatase inhibitors. Cell/Tissue lysates were incubated with rotation at 4° C. for 20 minutes to solubilize proteins, followed by centrifugation for 5 minutes at 13,000× g to pellet cell debris. Protein concentration was quantified using the BCA method. 15-20 µg of total protein was subjected to SDS gel electrophoresis using 4-12% Bis-Tris gels (Invitrogen) and transferred to nitrocellulose membranes for immunoblotting. Membranes were blocked for 1 hr at room temperature with LiCOR blocking solution, then incubated overnight at 4° C. with primary antibodies against pY416SFKs, (BD Biosciences; 1:1000) pY198Panx1 (Alpha Diagnostic Intl (ADI); 1:1000) and GAPDH (Sigma; 1:10,000) or an antibody against the intracellular loop of Panx1 (Panx1-IL) (ADI; 1:1000) (normalization controls). Membranes were then washed and incubated with LiCOR secondary antibodies (1:10,000) and visualized and quantitated using LiCOR Odyssey. To inhibit SFK activity, EC monolayers were incubated with the SFK inhibitor PP2 (Tocris; 10 µM). The inactive analog PP3 (Tocris; 10 µM) was used as a negative control for PP2. To show specificity for the phosphorylated form of SFKs and Panx1, cell lysates were incubated with alkaline phosphatase for 1 hour at 37° C. Western blot images have been cropped for presentation. Uncropped Western blots can be found in FIGS. 12-13. Data are expressed as mean±SEM (n=3 independent experiments).

Static Adhesion Assay

HUVECs were seeded on gelatin-coated glass coverslips in 6-well plates and grown to confluence. On the day of the experiment, cells were washed 2× with 1× PBS and incubated for 30 minutes in basal EGM supplemented with 1% BSA in the presence or absence of pharmacological inhibitors. During this incubation period, human THP-1 monocytes were loaded with Calcein-AM (Invitrogen; 5 µg/mL) for 30 minutes at 37° C. Cells were then pelleted by brief centrifugation and excess calcein was removed by washing THP-1 cells 3 times in 1× PBS. Next, HUVECs were stimulated with TNFα (10 ng/mL) for 30 minutes. Following EC activation, calcein-loaded THP-1 monocytes were added to EC monolayers and incubated for 20 minutes at 37° C. to allow THP-1 to contact ECs. Monolayers were then washed 3× with 1× PBS and fixed in ice cold 4% PFA. Following fixation, coverslips were removed from the 6-well plates and mounted on glass microscope slides with Prolong Gold anti-fade mountant with DAPI (Life Technologies). Fluorescent micrographs were obtained at 10×magnification and the number of adherent THP-1 monocytes/ECs was quantified in 5 randomized regions/slide. Data are expressed as mean±SEM (n=3 independent experiments).

Intravital Microscopy for Leukocyte Adhesion and Emigration

Mice were prepared for intravital microscopy of the cremaster muscle as described previously[25]. Briefly, mice were anesthetized with ketamine hydrochloride (150 mg/kg, IP) and xylazine (7.5 mg/kg, IP). The cremaster was isolated, laid over a viewing pedestal, superfused with bicarbonate-buffered saline. After 30 min equilibration, a venule with a wall shear rate (WSR) of ≥500/s, diameter between 20 µm and 40 µm, and the least number of adherent and emigrated leukocytes was chosen for further study. A 1 min baseline recording was made, after which superfusion was stopped, and 50 µl TNFα (1.7 ng/ml in 0.1% BSA) or vehicle control was added under a saran wrap cover every 30 min. 1 min recordings were made just prior to each addition, for 3 hrs. The TNFα was initially reconstituted in PBS at 3.4 ng/ml and 150 µl aliquots were frozen. An aliquot was mixed 1:1 with BBS containing 0.2% BSA at the time of the experiment. Leukocyte adhesion and emigration were determined by off-line analysis. Leukocytes were considered adherent if they stopped for at least 30 s (expressed as #/mm$^2$ vessel wall), and emigrated leukocytes were leukocytes identified in the interstitium (expressed as #cells/mm$^2$ tissue). Data are expressed as mean±SEM (n=6-7 independent animals/group).

Statistics

All statistics were performed using GraphPad Prizm software. For multiple comparisons, statistics were performed using a one-way or two-way ANOVA followed by pairwise analysis. A student's t-test was used for individual comparisons if normally distributed.

Results

TNFα Induces ATP Release from Venous Endothelial Cells

To test whether post-capillary endothelial cells provide a releasable pool of ATP in response to activation by inflammatory mediators, we assessed ATP release in response to activation by the pro-inflammatory cytokine TNFα. First, we developed an ex vivo vascular perfusion assay to selectively deliver TNFα to the endothelium of intact murine arterioles and venules. Following microdissection of paired 2$^{nd}$ order mesenteric arterioles and venules, vessels were cannulated on glass micropipettes mounted in a temperature controlled bath allowing access to the lumen and direct perfusion to a collection reservoir for sample acquisition (FIG. 1*a*). Perfusion of recombinant murine TNFα through the lumen of mesenteric venules produced a time- and dose-dependent increase in ATP accumulation in the perfusate as assessed by luciferin:luciferase-based bioluminescence (FIG. 1*b*). Perfusion of TNFα did not induce cell death evidenced by a lack of lactate dehydrogenase (LDH) accumulation in perfusates (FIG. 1*c*). Interestingly, this response was absent in paired mesenteric arterioles (FIG. 1*d*). The endothelium primarily senses soluble TNFα via TNF receptor type 1 (TNFR1); therefore, we utilized a peptide antagonist of this receptor (WP9QY) to examine whether ATP release occurs via a TNFR1-dependent mechanism. Lumenal perfusion of WP9QY prior to EC activation with TNFα significantly ablated the TNFα-induced ATP release from intact venous endothelium indicating a direct involvement of this receptor isoform (FIG. 1*e*). To further dissect the molecular mechanisms controlling ATP release in this response, we performed in vitro ATP release assays on two independent primary venous endothelial cell types derived from human umbilical vein (HUVEC) and human saphenous vein (HSaVEC). Following activation with recombinant human TNFα, we observed a significant increase in ATP accumulation in the supernatant surrounding both HUVEC and HSaVEC monolayers (FIG. 1*f-g*). Similar to isolated venules, TNFα stimulation did not activate caspase-dependent cell death pathways in cultured cells as evidenced by lack of inhibition in ATP release with the pan-caspase inhibitor Q-VD-OPh (FIG. 5). Consistent with the intact mesenteric venous endothelium, ATP release from cultured venous ECs increased in a dose- and time-dependent manner with maximal accumulation of extracellular ATP achieved following EC activation with 10 ng/mL TNFα for approximately 10 minutes. Similar to ex vivo analyses, two primary arterial EC types, human aortic (HAoEC) and human coronary artery (HCoAEC), failed to release ATP upon TNFα stimulation (FIG. 1*f-g*). This difference in response was not due to differential expression of TNFR1 in the isolated arteriole:venule pairs or the primary ECs (FIG. 6*a-b*). Moreover, blockade of TNFR1 signaling with WP9QY reduced the ATP release in response to increasing doses of TNFα on cultured venous ECs, consistent with the ex vivo observations (FIG. 1*h*, FIG. 8*a*). Next we aimed to examine the ability of another prominent pro-inflammatory cytokine interleukin-1 beta (IL-1β) to induce ATP from venous ECs. In contrast to TNFα, IL-1β failed to promote ATP release from HUVEC and HSaVEC monolayers (FIG. 7a-b). Co-administration of IL-1β with TNFα did not significantly alter the degree of ATP release as compared to TNFα stimulation alone, suggesting a mechanism specific to TNFR1 activation (FIG. 7c-d). Taken together, these results provide new evidence for the ability of TNFα to induce ATP release from venous endothelial cells through a signaling process specific to activation of the membrane receptor TNFR1.

Panx1 Controls ATP Release by Venous Endothelial Cells

Figure 2:
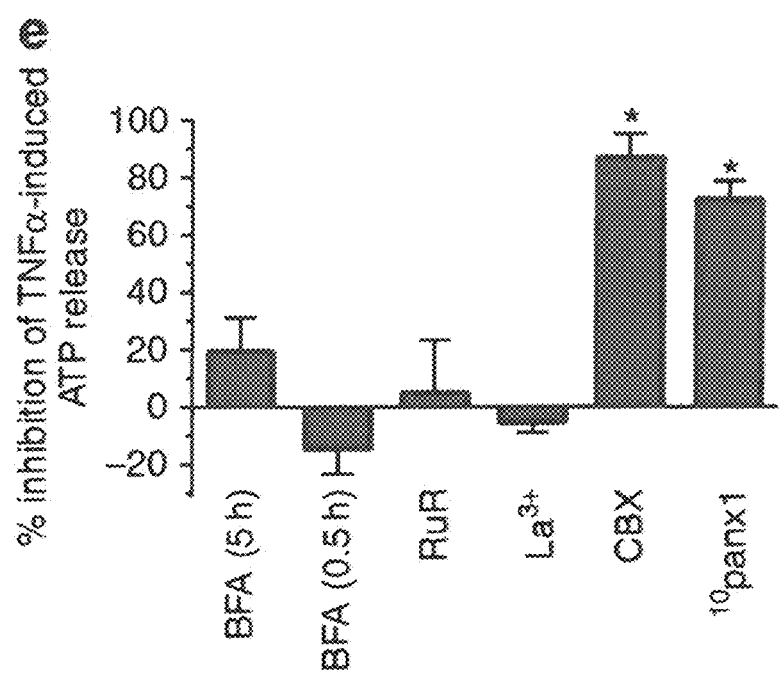
FIG. 2: Pannexin 1 channels mediate TNFα-induced ATP release from venous ECs (a) Representative Western blot of HUVEC treated with brefeldin A (BFA; 5 hours) and subsequent cell surface biotinylation of membrane proteins. Plasma membrane localization of Panx1 and Cx43 were assessed utilizing isoform specific antibodies to each protein. (b) ATP release from BFA treated HUVEC in response to TNFα (10 ng/mL) treatment for 30 minutes. (c-d) Time course of ATP release from HUVEC following inhibition of Panx1 channels with carbenoxolone (CBX: 50 µM) (c) and the Panx1 blocking peptide $^{10}$panx1 (200 µM) (d). $*=p<0.05$ as compared to vehicle control (n=5). (e) Summary data of pharmacological inhibitors assessed for inhibition of TNFα-induced ATP release from HUVEC. BFA (30 min): inhibition of vesicular release, Ruthenium Red (RuR): antagonist of CALHM1 channels. Lanthanum ($La^{3+}$): Cx hemichannel antagonist. $*=p<0.05$ as compared to BFA, RuR and $La^{3+}$ (n=5). (f) Representative Western blots of siRNA knockdown of Panx1 and Cx43 in HUVEC. $*=p<0.005$ and $=p<0.001$ vs. control (n=3). (g) ATP release from Panx1 and Cx43 siRNA treated HUVEC from (f) in response to TNFα (10 ng/mL). $*=p<0.005$ vs. control (n=3). (h) Schematic representing the generation of an inducible, EC-specific Panx1 knockout mouse (VECadER$^{T2+}$/Panx1$^{fl/fl}$). (i) En face immunofluorescence micrographs of Panx1 (red) expression of endothelium from VECadER$^{T2+}$/Panx1$^{fl/fl}$ mice injected with Tamoxifen (Tam) or its vehicle peanut oil (PO) for 10 consecutive days. Nuclei are stained with DAPI (blue). Scale bar is 10 µm. (j) Immuno-scanning electron micrographs (iSEM) of isolated mesenteric venules from VECadER$^{T2+/Panx1fl/fl}$ mice. Veins were immunolabeled for Panx1 (pseudo-colored magenta) using an antibody against the extracellular region of the channel. Right panels are zoomed images of left panels. Scale bar is 10 µm, enlarged boxes are 5 µm×5 µm (k) TNFα-induced ATP release from isolated mesenteric venules from VECadER$^{T2+/Panx1fl/fl}$ mice injected with Tam or PO for 10 days. Venules were perfused with 50 ng/mL TNFα or vehicle. $*=p<0.05$ as compared to vehicle perfused controls and $\#=p<0.05$ as compared to PO+TNFα (n=4). All data are presented as mean±SEM (error bars). Statistical analyses were performed using One-way ANOVA.
Figure 2:
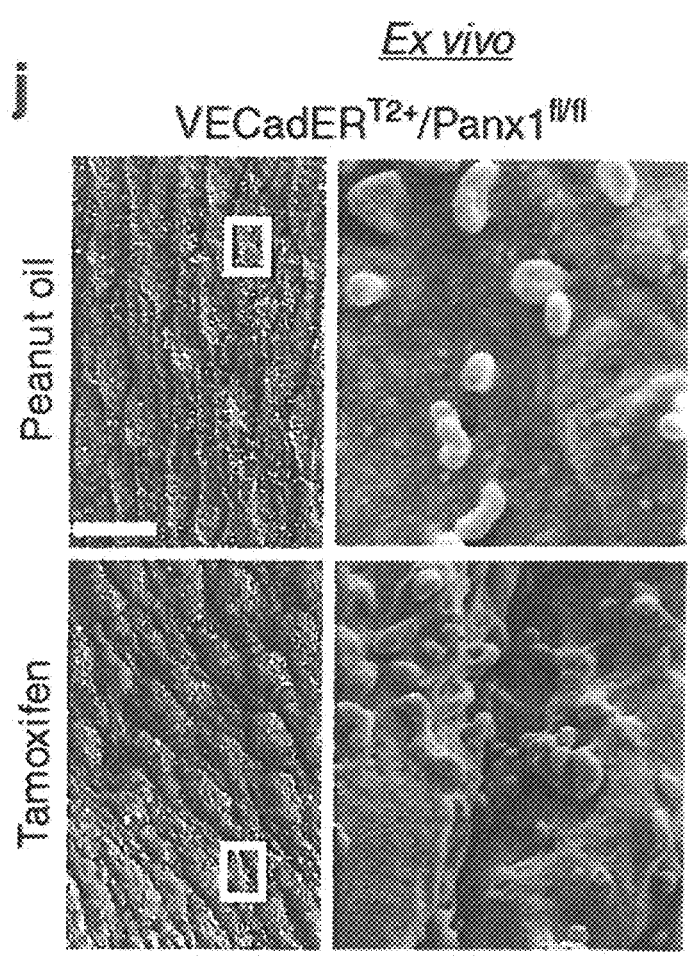
Figure 2:
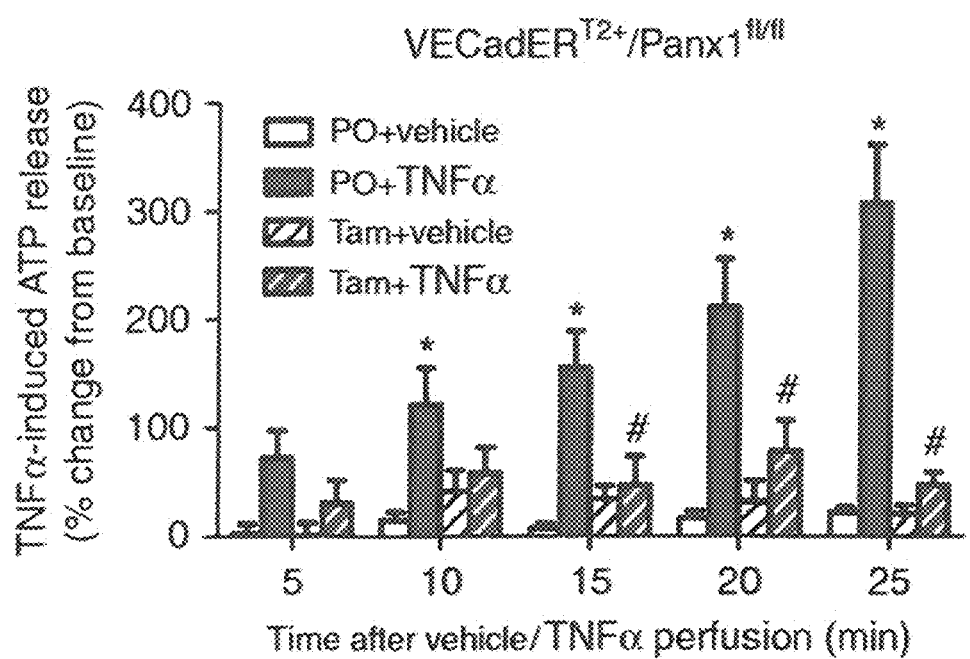

We next sought to identify the specific pathway regulating ATP release activated by TNFα. Multiple regulated ATP release pathways have been reported in the vasculature, including prominent roles for vesicular and channel-dependent ATP release primarily involving connexins (Cx) hemichannels and Panx1 channels[26] (Panx1 is the predominant isoform expressed in the systemic vasculature[10]; FIG. 6c). These two protein families share a similar membrane topology and distinguishing connexin hemichannels from pannexin channels in cellular ATP release has often proved cumbersome due to overlapping expression profiles in a number of cell types and the lack of specific pharmacological inhibitors[27]. Therefore, we took a multifaceted approach to dissect the TNFα-mediated ATP release pathway. Initially, to discriminate between the involvement of connexin hemichannels and Panx1 channels in this process, we utilized a biochemical method to selectively deplete connexins from the EC plasma membrane without affecting the localization of Panx1. Taking into account the relative half-life of each channel at the cell surface (Cx hemichannels: 1-5 hours[28], Panx1 channels: >6 hours[24]) treatment of HUVEC and HSaVEC with the vesicular exocytosis inhibitor brefeldin A (BFA; 5 μg/mL) prevented trafficking of newly synthesized Cx hemichannels and Panx1 channels to the cell surface while preserving internalization of older channels. Due to the relatively short half-life of Cx43 hemichannels (the major Cx isoform implicated in ATP release), 5 hour treatment with BFA decreased the expression of Cx43 at the EC surface without significantly altering the expression of Panx1 in both HUVEC (FIG. 2a) and HSaVEC (FIG. 8b). Importantly, under these experimental conditions, the ability of TNFα to induce ATP release was unaffected, suggesting that Panx1 channels may be more likely to mediate ATP release in response to the inflammatory cytokine (FIG. 2b, FIG. 8).

To more directly interrogate the contribution of Panx1 channels to ATP release from venous ECs we utilized two independent Panx1 pharmacological antagonists to block channel function, carbenoxolone (CBX) and the Panx1 inhibitory peptide [10]panx1. In HUVEC, Panx1 channel blockade with CBX (50 μM) or [10]panx1 (200 μM) significantly reduced TNFα-mediated ATP release by 86.4% and 70.9%, respectively (FIG. 2c-d). Similar inhibition was observed in HSaVECs (CBX: 69.7%, [10]panx1: 75.2%) (FIG. 8d). Furthermore, blockade of Cx hemichannels with lanthanum (La$^{3+}$; 100 μM) failed to reduce ATP release (FIG. 2e). Additional pharmacological interrogation ruled out the involvement of vesicular mechanisms (blocked with BFA) and calcium homeostasis modulator 1 (CALHM1) channels (inhibited with ruthenium red (RuR)[29]), which have recently been identified as potential ATP release channels (FIG. 2e, FIG. 8d). Moreover, employing RNA interference, selective knockdown of Panx1 in HUVEC and HSaVEC with siRNA duplexes targeting the PANX1 gene affirmed a central role for these channels in TNFα-induced ATP release, with not observed inhibition upon Cx hemichannel depletion with Cx43 siRNA. Knockdown efficiency was ~65% and ~75% in HUVEC (FIG. 2f) and HSaVEC (FIG. 8e), respectively. In both cell types, Panx1 knockdown significantly attenuated TNFα-induced ATP release (FIG. 2g, FIG. 8f). Finally, we assessed dye uptake by venous ECs as another output for Panx1 activity. Incubation of TNFα stimulated HUVEC with YO-PRO-1 produced a significant increase in intracellular dye accumulation in a dose dependent manner (FIG. 9a-b). This effect was significantly attenuated under conditions of Panx1 blockade with [10]panx1 (FIG. 8c). Moreover, addition of YO-PRO-1 to HUVEC monolayers 10 minutes or later following TNFα stimulation resulted in a significant decrease in dye uptake as compared to conditions where YO-PRO-1 was present at the onset of TNFα stimulation (FIG. 9d). These data, along with the rapid and transient ATP release observed, suggest that EC Panx1 activation is transient in nature with the channels closing within 10 minutes of becoming activated by TNFα-dependent signaling mechanisms.

To directly investigate the contribution of endothelial Panx1 channels to TNFα-induced ATP release in the intact venous circulation, we engineered mice that specifically lack Panx1 expression in endothelial cells. This was accomplished by crossing mice carrying loxP sites flanking exon 3 of the murine Panx1 gene (Panx1$^{fl/fl}$)[23] with transgenic mice carrying a tamoxifen sensitive Cre recombinase driven by the vascular endothelial cell cadherin promoter (VECad-ER$^{T2-}$) (FIG. 2h). Because this Cre is basally inactive until tamoxifen treatment, this allowed the mice to develop normally and provided the ability to induce deletion of Panx1 specifically in ECs at the time of our choosing. Following 10 days of tamoxifen administration, VECadER$^{T2}$/Panx1$^{fl/fl}$ mice displayed a substantial reduction in Panx1 expression in the endothelium as assessed by immunofluorescence microscopy and immune-transmission electron microscopy (immune-TEM) (FIG. 2i-j). Luminal perfusion of TNFα in isolated mesenteric venules from these mice displayed a marked inhibition of ATP release compared to littermate controls (i.e. injected with the vehicle peanut oil (PO) only) (FIG. 2k). Taken together, these data suggest a direct role for Panx1 channels in releasing ATP from venous endothelial cells in response to TNFα.

Src Family Kinases phosphorylate Panx1 in endothelial cells

Figure 3:
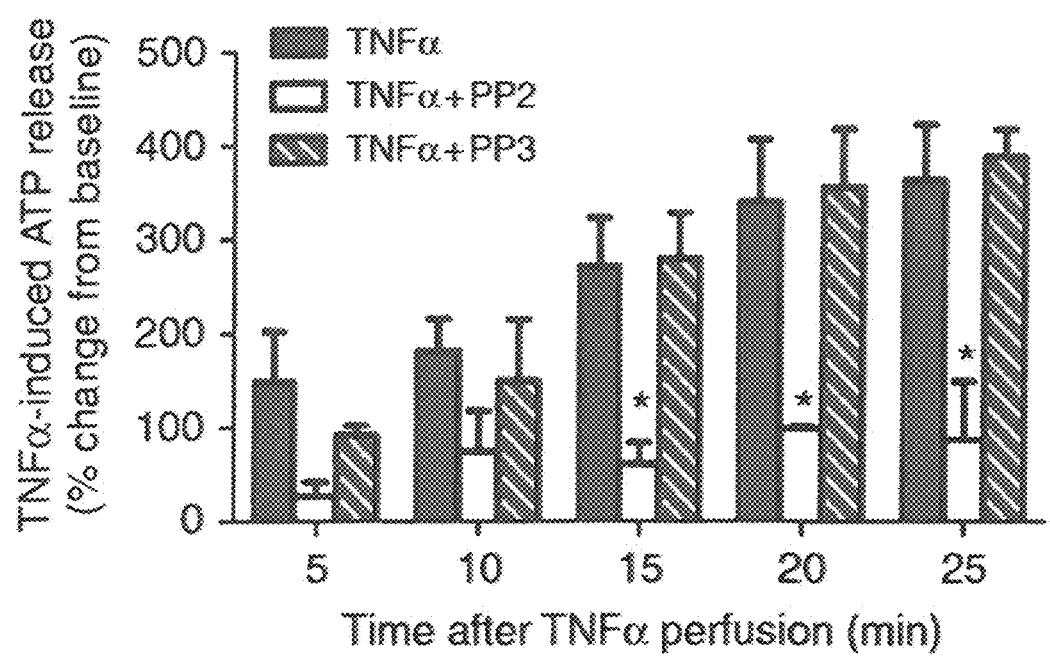
FIG. 3: TNFα induces Src Family Kinase-dependent activation of EC Panx1 channels (a) Western blot analysis of SFK activation in HUVEC in response to TNFα stimulation (10 ng/mL). A phospho-specific antibody against Y 416 in SFKs (p Y 416SFK) was used as an indicator of SFK activation. SFK activation was blocked with the pharmacological antagonist PP2 (10 µM) but not by its inactive analog PP3 (10 µM). Antibody specificity for the phosphorylated form of the kinases was confirmed by de-phosphorylating proteins in cell lysates with alkaline phosphatase. $*=p<0.05$ as compared to unstimulated control (lane 1) and $\#=p<0.001$ as compared to lane 1 (n=3). (b) TNFα-induced ATP release from HUVEC following SFK inhibition with PP2. $*=p<0.05$ vs. control and PP3 treatments (n=5). (c) Topological schematic of Panx1 highlighting an epitope in the intracellular loop which containing tyrosine 198. This epitope was used to develop antibodies specific to the phosphorylated (pY198Panx1; SEQ ID NO: 9) and non-phosphorylated (Panx1-IL: SEQ ID NO: 10) forms of the protein. (d) Overlay of pY198Panx1 signal and Panx1-IL (total) signal as assessed by Western blotting with LiCOR IRDye secondary antibodies. pY198Panx1 detects a single species at ~55 kD. (e) Western blot analysis of p Y198Panx1 in HUVEC transfected with plasmids encoding c-Src or and inhibitor of Src (i-Src). (f) Western blot analysis of Panx1 phosphorylation at Y198 in HUVECs stimulated with TNFα (10 ng/mL). Phospho-signal was normalized to total Panx1 expression using the Panx1-IL Ab. *=p<0.05 compared to vehicle control (lane 1) and #=p<0.01 compared to 5 min TNFα stimulation (lane 4) (n=3). (g) TNFα-induced ATP release from mesenteric venules treated with PP2 (10 μM) or PP3 (10 μM). *=p<0.05 as compared to vehicle control (n=5). (h-i) Western blot analysis of TNFα-induced SFK activation (h) and pY198Panx1 phosphorylation (i) in isolated mesenteric venules perfused with TNFα (50 ng/mL) for 30 minutes. (j) Immunofluorescence micrographs of 5 p Y198Panx1 in isolated mesenteric venule cross sections. Venules were isolated from mice expressing endogenous Panx1 in the vascular wall (VECadER$^{T2+}$/Panx1$^{fl/fl}$ Peanut Oil) or mice with specific EC Panx1 deletion (VECadER$^{T2+}$/Panx1$^{fl/fl}$ Tamoxifen) and stimulated with TNFα. Asterisks indicate the vessel lumen and nuclei are stained with DAPI (blue). Scale bar is 30 μm. All data are presented as mean±SEM (error bars). Statistical analyses were performed using One-way ANOVA.
Figure 3:
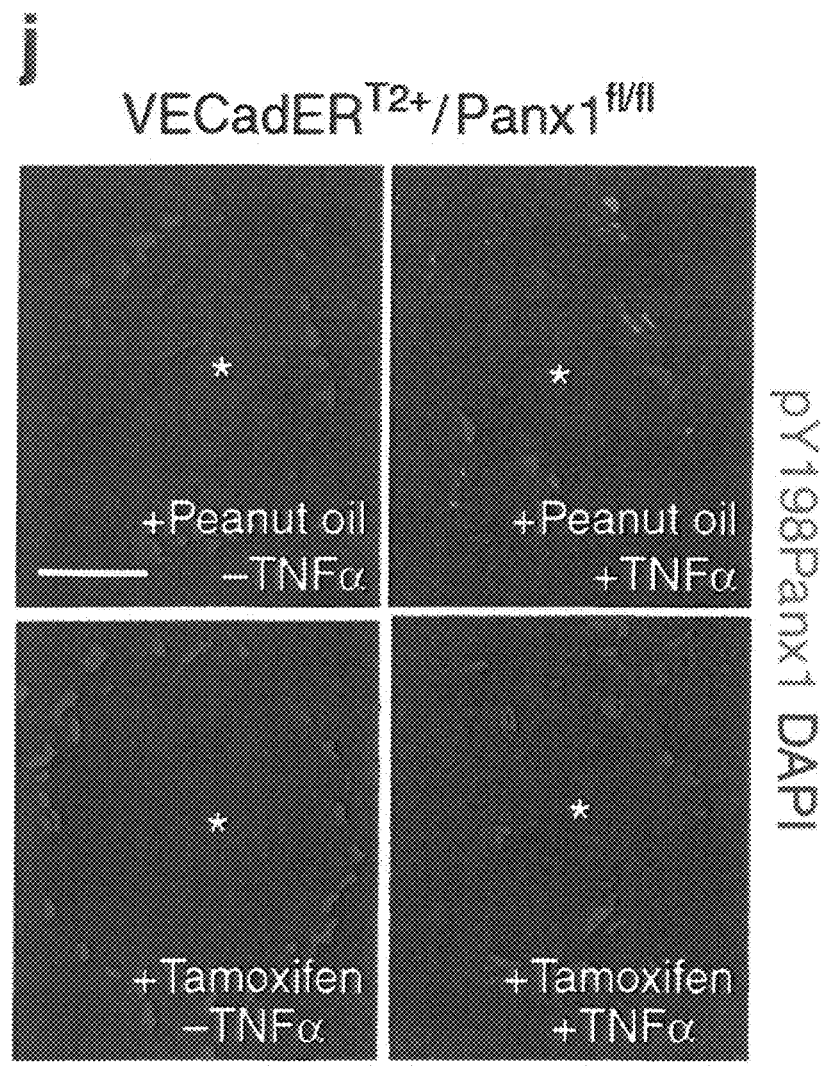

Next, we aimed to elucidate the mechanism by which activation of TNFR1 in venous endothelial cells could translate to Panx1 channel opening. TNFR1 activation has been reported to induce the activity of a number of intracellular kinases, including the Src Family Tyrosine Kinases (SFK)[30,31]. In addition, endothelial and inflammatory cell SFKs are involved in increasing EC barrier permeability and increasing the recruitment, adhesion and transmigration of circulating neutrophils, monocytes and macrophages to inflamed tissues[32]. Recent analysis of Panx1 activity in hippocampal neurons revealed the involvement of SFKs in NMDA-mediated Panx1 activation[33]. Therefore, we assessed the potential contribution of SFKs in TNFα-induced Panx1 activation and ATP release from venous endothelial cells. SFK activation can be assessed by autophosphorylation of a conserved tyrosine residue (Y416) which stabilizes a substrate-permissive, active site conformation in the kinases[34]. Utilizing a phospho-specific Y416SFK antibody, we detected a significant increase in Y416 phosphorylation in both HUVEC (FIG. 3a) and HSaVEC (FIG. 8g) following acute (5 minute) exposure to recombinant human TNFα in vitro, consistent with the rapid induction of ATP release from these cultured primary cells. This effect was specific to SFK activation as treatment of both venous cell types with the SFK inhibitor PP2 reduced Y416 phosphorylation to baseline levels, while PP3 (the inactive analog of PP2) had no effect. Functionally, pharmacological inhibition of SFKs with PP2 significantly blunted TNFα-induced ATP release from both HUVEC (FIG. 3b) and HSaVEC (FIG. 8h), while PP3 showed no significant effect. Importantly, examination of SFK activation downstream of TNFα signaling in isolated mesenteric venules revealed a conserved role for SFKs in promoting ATP release from intact venous endothelium, with PP2 blunting ATP release (FIG. 3g) and TNFα increasing SFK activation (FIG. 3h).

We next sought to determine whether Panx1 channels are targets for phosphorylation downstream of SFK activation. Recently, our laboratory defined a region of the Panx1 intracellular loop that is important for receptor-mediated channel activation in vascular smooth muscle cells. This intracellular loop region (amino acids 198-200) contains a highly conserved tyrosine residue (Y198) which may constitute a putative SFK phosphorylation site'. From these observations, we developed a new phospho-specific Panx1 antibody against Y198 (pY198Panx1) and a control antibody against the same non-phosphorylated epitope (Panx1-IL) (FIG. 3c). The pY198Panx1 antibody detects a singular Panx1 species of ~55 kDa by Western blotting (FIG. 3d). Overexpression of c-Src in HUVEC significantly increased phosphorylation of Panx1 at Y198 as compared to cells expressing an inhibitor of Src (i-Src) (FIG. 3e). In addition, this response could be blocked by inhibition of Src with PP2.

Using this newly developed tool, we addressed Panx1 phosphorylation downstream of TNFα signaling. Panx1 was phosphorylated downstream of TNFα-induced SFK activation in endothelial cells. Specifically, treatment of HUVEC and HSaVECs with TNFα increased phosphorylation at Y198, which could be blocked by pretreatment with the SFK inhibitor PP2 (FIG. 3f; FIG. 8i). To directly assess the specificity of this antibody against the phosphorylated form of the channel, we performed dephosphorylation reactions with alkaline phosphatase, which depleted the signal by Western blotting. In our ex vivo vascular preparations, stimulation of primary endothelial cells with TNFα also promoted phosphorylation of Panx1 (FIG. 3i). In these studies, isolated mesenteric venules containing both ECs and vascular smooth muscle cells were lysed to produce a heterogeneous sample. To more accurately discriminate between EC and VSMC Panx1 pools, we performed immunofluorescence microscopy on cross sections of mesenteric venules using our pY198Panx1 antibody. Mice expressing endogenous levels of Panx1 in the vascular wall (VECad-ER$^{T2+}$/Panx1$^{fl/fl}$+PO) showed a significant increase in Panx1 phosphorylation following stimulation with TNFα (FIG. 3j). Administration of tamoxifen to a subset of mice abolished this signal, supporting the specificity of pY198Panx1 for Panx1. These observations provide new evidence for phosphorylation of Panx1 in the venous endothelium in the activation of these channels during TNFα signaling.

Panx1 Activation Promotes Leukocyte Adhesion and Emigration

Figure 11A:
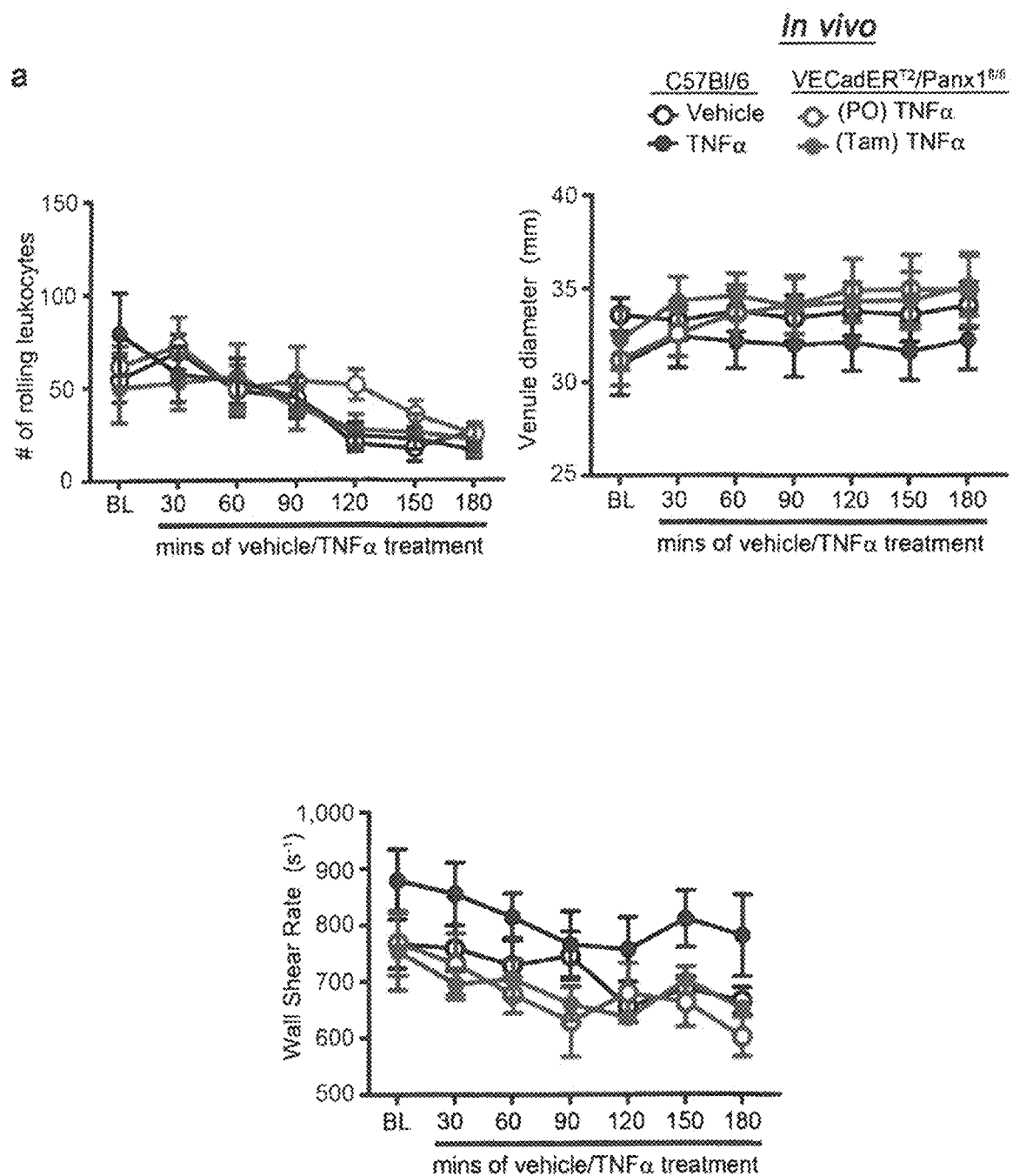

We next tested whether the endothelial cell ATP release mediated via this TNFα-Panx1 axis may induce leukocyte recruitment to localized inflammatory foci using gold standard in vitro assays to emulate leukocyte adhesion and emigration in vivo. We initially utilized an in vitro leukocyte adhesion assay. In this assay system, activation of HUVEC monolayers with TNFα for 30 minutes increased THP-1 monocyte adhesion by ~4-fold (FIG. 10a-b). This effect was significantly reduced by blockade of TNFR1 (WP9QY), Panx1 channels (CBX and $^{10}$panx1) and degradation of extracellular ATP (Apyrase). These in vitro results suggest a potentiating role for Panx1-dependent ATP release in promoting inflammatory cell interactions with venous ECs. To more directly determine the in vivo contribution of Panx1 to acute vascular inflammation, we utilized intravital microscopy of the exteriorized mouse cremaster muscle. Topical application of TNFα to the cremaster circulation in C57B$^{1/}$$_6$J mice promoted a significant increase in leukocyte interactions with the post-capillary venular endothelium (FIG. 4a-b). Specifically, leukocyte adhesion increased ~2.5-fold and emigration increased by ~3.5 fold after 120 minutes of TNFα stimulation. Genetic deletion of Panx1 specifically in the endothelium (VECadER$^{T2+}$/Panx1$^{fl/fl}$ mice, tamoxifen injected) potently ablated leukocyte adhesion and emigration compared to vehicle (peanut oil only) injected littermates and wild type C57B1/6J control animals. Importantly, the leukocyte rolling per se was unaffected after endothelial deletion of Panx1, suggesting the effects of Panx1 activity are required downstream of the initial rolling stage (FIG. 11a). Additionally, venule diameter and wall shear rate did not differ between control and Panx1 deleted animals (FIG. 11a). In addition, the potent inhibition of adhesion and emigration was not due to off target effects of tamoxifen administration per se, as tamoxifen administration to control C57B$^{1/}$$_6$J mice had no effect on these responses (FIG. 11b-c).

Panx1-Mediated ATP Release Upregulates VCAM1

Based on the observation that Panx1 activation primarily regulates adhesion and transmigration, we sought to examine the effect of EC Panx1 deletion on the upregulation of VCAM1. VCAM1 is substantially upregulated during EC activation by cytokines and functions to bind its complementary ligand $α_4β_1$ integrin (VLA-4) expressed on circulating leukocytes. Binding of VCAM1 to VLA-4 elicits firm adhesion of circulating cells to the endothelium, allowing downstream emigration into the inflamed tissue. Recently, several studies have emerged implicating ATP and purinergic receptor stimulation in VCAM1 upregulation[36-38]. We performed immunofluorescence microscopy on TNFα stimulated mesenteric venules isolated from our endothelial cell-specific Panx1 KO mice to initially assess the effect on VCAM1 expression. Activation of venules from mice injected with peanut oil increased total VCAM1 expression in the endothelium (FIG. 4c). Conversely, deletion of Panx1 by tamoxifen administration blunted this cytokine-induced VCAM1 upregulation, suggesting a functional role for Panx1 activation in promoting increased expression of the adhesion molecule (FIG. 4c). Furthermore, this effect was due to the release of ATP via Panx1, since VCAM1 upregulation could be rescued in Panx1 KO mice by stimulating with exogenous ATP (FIG. 4d).

Collectively, these new data identify a previously unrecognized signaling pathway implicating Panx1 as a positive regulator of inflammation in the venous endothelium. Specifically, we show that following activation of TNFR1 on venous ECs, SFKs become activated and signal the activation of Panx1 channels. Opening of the Panx1 pore causes ATP liberation from the cells along a concentration gradient where it signals extracellularly to promote leukocyte adhesion to the vascular endothelium and subsequent emigration into the inflamed tissue (FIG. 4e). Physiologically, Panx1 channels represent a potential new target for regulating the purinergic input into inflammatory signaling through TNFα in the vasculature, and this may prove useful for future pharmacological intervention to regulate inflammatory disorders.

Discussion

In the cardiovascular system, ATP and its metabolites function extracellularly to regulate the vascular inflammatory response, affecting major aspects of inflammatory signaling in the endothelium including the presentation of adhesion molecules and the integrity of the endothelial cell barrier function. While multiple lines of evidence now support a pro-inflammatory role for ATP, the source and mechanism promoting the cellular release of this purine nucleotide is not well defined. Here, using multiple in vitro, ex vivo and in vivo models we provide new evidence identifying Pannexin 1 channels as major conduits for ATP release from the venous endothelium during acute inflammatory stress with channel activation promoting leukocyte adhesion and emigration across the vessel wall.

Tumor necrosis factor α and interleukin 1β are the major cytokines that initially regulate vascular cell phenotype during acute systemic inflammation. Increased extracellular concentrations of these signaling molecules is readily observed in a number of inflammatory states and recent evidence has emerged linking cytokine signaling by TNFα to purinergic pathways in the vasculature[3,4]. Our analysis of cytokine induced ATP release revealed a selective mechanism by which TNFα, but not IL-1β, potentiates cellular ATP release from venous ECs. By these means, EC activation by TNFα and subsequent priming for interactions with circulating inflammatory cells may be favored by a purinergic amplification step. This is particularly intriguing when considering the dichotomous relationship between cell survival and cell death with respect to TNFα signaling. This cytokine at low/acute concentrations favors cell survival pathways and homeostatic maintenance at the level of inflammatory cell recruitment through complex I signaling. As such, a purinergic amplification step may promote non-deleterious signaling in the absence of chronic TNFα exposure. In this respect, acute IL-1β signaling may not require this type of amplification, which is evidenced by the observed lack of ATP release from ECs exposed to this cytokine and lack of a synergistic effect when IL-1β and TNFα are applied concurrently. This evidence may shed new light on the complexity of inflammatory signaling in the venous circulation prompting further analysis of the interplay between the multiple signaling processes controlling EC activation in the whole animal during inflammation. Our analysis employed a range of TNFα concentrations (0.1-100 ng/mL) to evaluate the effect on EC ATP release with a significant response observed to doses at 10 ng/mL and higher. Depending on the inflammatory model tested, measurements of endogenous circulating levels of TNFα in both humans and animal models have shown considerable variability; however, these values in general fall in the pg/mL-ng/mL range. A number of factors likely contribute to this variation including the absolute systemic blood volume, activity of TNFα processing enzymes and presence of chelators including soluble TNF receptors. As such, the absolute concentration of TNFα in the microenvironment near the EC surface is likely underestimated by conventional measurements from serum samples prompting a need for more sensitive techniques for quantifying cytokine concentrations in these local environments.

Our study revealed a venous selectivity to TNFα-induced ATP release, where ECs of venous origin release ATP following activation by TNFα with negligible responses in the arterial endothelium. In fact, it has long been observed that inflammatory cell homing to localized tissues occurs almost exclusively in the post-capillary venous circulation, while these interactions are not evident in the arterial vasculature until a level of chronic inflammation is reached[39,40]. Panx1 channels, therefore, may provide a regulated mechanism by which physiological homing of inflammatory cells through the venous endothelium is tightly regulated.

Here, we have characterized a molecular signaling pathway involving activation of type 1 TNF receptors, Src family kinases, and phosphorylation of Panx1 channels. Recent evidence has identified a novel role for TNFR1 as apseudo-receptor tyrosine kinase, achieved through docking of Src kinase to an intracellular domains of the receptoe[30,31]. Moreover, the regulation of Panx1 activity by kinase-driven signaling mechanisms is gaining support. Specifically, a prominent role for Src Family Kinases (SFK) in promoting Panx1 channel activity has been established in neurons during anoxic depolarizations in ischemia. However, to date there has been no direct evidence for Panx1 phosphorylation. Our analysis of SFK-dependent Panx1 activation revealed that these channels are indeed phosphorylated and that this modification may promote an open channel state. While the precise mode of Panx1 activation in response to SFK mediated phosphorylation is still under investigation, recent reports hypothesize that channel gating is intimately regulated by interactions between the C-terminal tail and the channel pore [41,42]. It is interesting to speculate that phosphorylation of the Panx1 intracellular loop at Y198 may impart electrostatic interactions with the C-tail to sequester this region from the pore and promote an open channel conformation. It also currently remains unclear as to whether Panx1 channels are directly activated by phosphorylation of Y198 or if additional tyrosine residues are modified contributing to this effect. In addition to Src, the serine/threonine kinases ERK and p38MAPK have been reported to rapidly activate in response to TNFα stimulation, which may contribute to the regulation of Panx1 channels in the endothelium[43,44]. Thus, dynamic phosphorylation of Panx1 may be evident during vascular inflammation and be a factor influencing the heterogeneity in venous versus arterial EC-dependent ATP release.

The kinetics of TNFα-dependent activation of Panx1 in venous ECs suggests that the channels operate transiently to mediate ATP release and downstream purinergic cascades. Specifically, activation of ECs with TNFα induced ATP release and YO-PRO-1 dye uptake within minutes with concurrent SFK activation and Panx1 phosphorylation. With respect to the transient nature of Panx1 activity in this response, a number of regulatory mechanisms may be in place to prevent excessive ATP release. ATP itself has been reported to negatively regulate channel activity following accumulation in the extracellular compartment[45]. It is suggested that ATP acts allosterically near the extracellular vestibule of the Panx1 permeation pore to limit further ATP release. Examination of the kinetics of ATP release between our cell culture models and perfused vessels revealed a saturation under static conditions where ATP was allowed to accumulate in the extracellular milieu surrounding cultured cells. However, during continuous lumenal perfusion in our isolated vessel system, ATP continually accumulated in the perfusate, which may be explained by removal of the purine by flow and prevention of an ATP block on Panx1 channels. Endothelial cells also harbor an endogenous negative feedback mechanism to control Panx1 function. Specifically, our lab has reported an inhibitory effect of the EC-derived bioactive gas nitric oxide (NO) on Panx1 activity through targeted S-nitrosylation of two conserved cysteine thiols, one located in the predicted pore-lining region of the channel and one in the C-tail[15]. Targeted S-nitrosylation of these residues reduces ATP release and Panx1 channel currents in murine ECs. Activation of EC purinergic receptors by ATP can increase NO production which may serve as a possible off switch to prevent cytosolic ATP depletion and loss of ionic gradients controlled by ATP regulated ion transporters. Src is also regulated by S-nitrosylation with modification reported to increase its kinase activity[46,47]. Based on these observations, there may be a dynamic interplay between Src and Panx1 S-nitrosylation during inflammation, which could regulate the balance between cell survival pathways and cell death. Of particular interest, the temporal dynamics of Panx1 and Src post-translational modification will aid in determining the potential effects of NO on EC-dependent inflammatory signaling during the acute and chronic phases. In addition, a prominent role for NO as an anti-inflammatory mediator has been well established where increased NO production in the vasculature reduces leukocyte rolling, adhesion and emigration[48-53]. TNFα can also induce rapid activation of NADPH oxidase which may alter the redox state of cysteine residues in Panx1 and modify NO-dependent channel regulation[43]. Future studies will provide useful insight into the regulation of Panx1 channels by oxidative stress and NO during inflammatory signaling; however, it is interesting to speculate that a portion of the anti-inflammatory effects of NO are due to S-nitrosylation of Panx1 to limit the release of pro-inflammatory ATP.

Our in vitro and in vivo analyses of leukocyte-EC interactions in response to the acute inflammatory stimulus TNFα identified a major contribution of venous EC Panx1 channels in promoting adhesion to and extravasation through the vascular wall. Blocking Panx1 activity pharmacologically in vitro, and molecularly in vivo, reduced leukocyte adhesion to TNFα-primed ECs and abolished emigration of circulating and adherent leukocytes through post-capillary venules in the exteriorized mouse cremaster preparation. This effect was specific to the expression of EC Panx1 channels since administration of tamoxifen to C57B1/6 mice had no effect on TNFα-stimulated adhesion and emigration (FIG. 11b-c) as compared to the potent ablation in both processes in VECadER$^{T2+}$/Panx1$^{fl/fl}$ mice which received tamoxifen. No significant differences were seen in rolling velocity and the absolute number of rolling leukocytes between animals indicating that the activity of Panx1 channels predominantly contributes to the downstream events including adhesion and emigration. The initial rolling and attachment of inflammatory cells to the endothelium is controlled primarily by selectin molecules (P-selectin and E-selectin), while firm adhesion and extravasation is promoted by the upregulation of VCAM1 and ICAM1. In accordance with this, we observed that deletion of Panx1 from the endothelium prevented TNFα-mediated VCAM1 upregulation implicating Panx1-dependent ATP release in the latter phase of inflammatory cell homing. This effect could be rescued by the exogenous application of ATP. These experiments link previous reports of purinergic signaling through P2Y receptors in the acute inflammatory cascade with Panx1 mediated release of ATP from the endothelium. While our investigation focused on the role of EC Panx1 channels and the role of released ATP on EC phenotype, leukocytes also utilize purinergic signaling for activation during inflammation[54-56]. It is now evident that neutrophils release ATP in response to activation by danger signals. In particular, activation of neutrophils with fMLP promotes ATP release in part via Panx1 channels which signals in an autocrine fashion to activate P2Y2 receptors and promote chemotaxis[57]. Neutrophils also express TNF receptors, however, whether activation of these receptors induces Panx1 activation or ATP released from EC Panx1 channels contributes to neutrophil chemotaxis has not been investigated. Nonetheless, it is possible that the reduced interactions observed between endogenous leukocytes and the venous endothelium in EC Panx1 knockout mice may reflect diminished purinergic signaling in both ECs and the inflammatory cells. Taken together, the results presented in this study highlight a novel role for EC Panx1 channels in the regulation of acute vascular inflammation, poising Panx1 as a linking factor between TNFα signaling and purinergic control of inflammatory cell interactions with the blood vessel wall.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Ley, K., Laudanna, C., Cybulsky, M. I. & Nourshargh, S. Getting to the site of inflammation: the leukocyte adhesion cascade updated. Nature reviews. Immunology 7, 678-689, doi:10.1038/nri2156 (2007).

2. Ralevic, V. & Burnstock, G. Receptors for purines and pyrimidines. Pharmacological reviews 50, 413-492 (1998).

3. Zerr, M. et al. Major contribution of the P2Y(1)receptor in purinergic regulation of TNFalpha-induced vascular inflammation. Circulation 123, 2404-2413, doi:10.1161/CIRCULATIONAHA.110.002139 (2011).

4. Riegel, A. K. et al. Selective induction of endothelial P2Y6 nucleotide receptor promotes vascular inflammation. Blood 117, 2548-2555, doi:10.1182/blood-2010-10-313957 (2011).

5. Hyman, M. C. et al. Self-regulation of inflammatory cell trafficking in mice by the leukocyte surface apyrase CD39. The Journal of clinical investigation 119, 1136-1149, doi:10.1172/JCI36433 (2009).

6. McDonald, B. et al. Intravascular danger signals guide neutrophils to sites of sterile inflammation. Science 330, 362-366, doi:10.1126/science.1195491 (2010).

7. Reutershan, J. et al. Adenosine and inflammation: CD39 and CD73 are critical mediators in LPS-induced PMN trafficking into the lungs. FASEB journal : official publication of the Federation of American Societies for Experimental Biology 23, 473-482, doi:10.1096/fj.08-119701 (2009).

8. Bouma, M. G., van den Wildenberg, F. A. & Buurman, W. A. Adenosine inhibits cytokine release and expression of adhesion molecules by activated human endothelial cells. The American journal of physiology 270, C522-529 (1996).

9. Koszalka, P. et al. Targeted disruption of cd73/ecto-5'-nucleotidase alters thromboregulation and augments vascular inflammatory response. Circulation research 95, 814-821, doi:10.1161/01.RES.0000144796.82787.6f (2004).

10. Lohman, A. W. et al. Expression of pannexin isoforms in the systemic murine arterial network. Journal of vascular research 49, 405-416, doi:10.1159/000338758 (2012).

11. Billaud, M. et al. Pannexin1 regulates alpha1-adrenergic receptor-mediated vasoconstriction. Circulation research 109, 80-85, doi:10.1161/CIRCRESAHA.110.237594 (2011).

12. Gaynullina, D., Shestopalov, V. I., Panchin, Y. & Tarasova, 0. S. Pannexin 1 facilitates arterial relaxation via an endothelium-derived hyperpolarization mechanism. FEBS letters 589, 1164-1170, doi:10.1016/j.febslet.2015.03.018 (2015).

13. Gaynullina, D., Tarasova, 0. S., Kiryukhina, O., Shestopalov, V. I. & Panchin, Y. Endothelial function is impaired in conduit arteries of pannexin1 knockout mice. Biol Direct 9, 8, doi:10.1186/1745-6150-9-8 (2014).

14. Bao, L., Locovei, S. & Dahl, G. Pannexin membrane channels are mechanosensitive conduits for ATP. FEBS letters 572, 65-68, doi:10.1016/j.febslet.2004.07.009 (2004).

15. Lohman, A. W. et al. S-nitrosylation inhibits pannexin 1 channel function. The Journal of biological chemistry 287, 39602-39612, doi:10.1074/jbc.M112.397976 (2012).

16. Adamson, S. E. & Leitinger, N. The role of pannexin1 in the induction and resolution of inflammation. FEBS letters 588, 1416-1422, doi:10.1016/j.febslet.2014.03.009 (2014).

17. Pelegrin, P. & Surprenant, A. Pannexin-1 mediates large pore formation and interleukin-1beta release by the ATP-gated P2X7 receptor. The EMBO journal 25, 5071-5082, doi:10.1038/sj.emboj.7601378 (2006).

18. Silverman, W. R. et al. The pannexin 1 channel activates the inflammasome in neurons and astrocytes. The Journal of biological chemistry 284, 18143-18151, doi: 10.1074/jbc.M109.004804 (2009).

19. Chekeni, F. B. et al. Pannexin 1 channels mediate 'find-me' signal release and membrane permeability during apoptosis. Nature 467, 863-867, doi:10.1038/nature09413 (2010).

20. Woehrle, T. et al. Pannexin-1 hemichannel-mediated ATP release together with P2X1 and P2X4 receptors regulate T-cell activation at the immune synapse. Blood 116, 3475-3484, doi:10.1182/blood-2010-04-277707 (2010).

21. Gulbransen, B. D. et al. Activation of neuronal P2X7 receptor-pannexin-1 mediates death of enteric neurons during colitis. Nature medicine 18, 600-604, doi:10.1038/nm.2679 (2012).

22. Riteau, N. et al. Extracellular ATP is a danger signal activating P2X7 receptor in lung inflammation and fibrosis. American journal of respiratory and critical care medicine 182, 774-783, doi:10.1164/rccm.201003-0359OC (2010).

23. Poon, I. K. et al. Unexpected link between an antibiotic, pannexin channels and apoptosis. Nature 507, 329-334, doi:10.1038/nature13147 (2014).

24. Penuela, S. et al. Pannexin 1 and pannexin 3 are glycoproteins that exhibit many distinct characteristics from the connexin family of gap junction proteins. Journal of cell science 120, 3772-3783, doi:10.1242/jcs.009514 (2007).

25. Stokes, K. Y., Calahan, L., Russell, J. M., Gurwara, S. & Granger, D. N. Role of platelets in hypercholesterolemia-induced leukocyte recruitment and arteriolar dysfunction. Microcirculation 13, 377-388, doi:10.1080/10739680600745877 (2006).

26. Lohman, A. W., Billaud, M. & Isakson, B. E. Mechanisms of ATP release and signalling in the blood vessel wall. Cardiovascular research 95, 269-280, doi:10.1093/cvr/cvs187 (2012).

27. Lohman, A. W. & Isakson, B. E. Differentiating connexin hemichannels and pannexin channels in cellular ATP release. FEBS letters 588, 1379-1388, doi:10.1016/j.febslet.2014.02.004 (2014).

28. Laird, D. W. Life cycle of connexins in health and disease. The Biochemical journal 394, 527-543, doi: 10.1042/BJ20051922 (2006).

29. Taruno, A. et al. CALHM1 ion channel mediates purinergic neurotransmission of sweet, bitter and umami tastes. Nature 495, 223-226, doi:10.1038/nature11906 (2013).

30. Pincheira, R., Castro, A. F., Ozes, 0. N., Idumalla, P. S. & Donner, D. B. Type 1 TNF receptor forms a complex with and uses Jak2 and c-Src to selectively engage signaling pathways that regulate transcription factor activity. J Immunol 181, 1288-1298 (2008).

31. Xing, L. et al. Genetic evidence for a role for Src family kinases in TNF family receptor signaling and cell survival. Genes & development 15, 241-253 (2001).

32. Okutani, D., Lodyga, M., Han, B. & Liu, M. Src protein tyrosine kinase family and acute inflammatory responses. American journal of physiology. Lung cellular and molecular physiology 291, L129-141, doi:10.1152/ajplung.00261.2005 (2006).

33. Weilinger, N. L., Tang, P. L. & Thompson, R. J. Anoxia-induced NMDA receptor activation opens pannexin channels via Src family kinases. The Journal of neuroscience : the official journal of the Society for Neuroscience 32, 12579-12588, doi:10.1523/JNEUROSCI.1267-12.2012 (2012).

34. Kmiecik, T. E. & Shalloway, D. Activation and suppression of pp60c-src transforming ability by mutation of its primary sites of tyrosine phosphorylation. Cell 49, 65-73 (1987).

35. Billaud, M. et al. A molecular signature in the pannexin1 intracellular loop confers channel activation by the alpha1 adrenoreceptor in smooth muscle cells. Sci Signal 8, ra17, doi:10.1126/scisignal.2005824 (2015).

36. Baker, O. J., Camden, J. M., Rome, D. E., Seye, C. I. & Weisman, G. A. P2Y2 nucleotide receptor activation up-regulates vascular cell adhesion molecule-1 [corrected] expression and enhances lymphocyte adherence to a human submandibular gland cell line. Mol Immunol 45, 65-75, doi:10.1016/j.molimm.2007.05.009 (2008).

37. Smedlund, K. & Vazquez, G. Involvement of native TRPC3 proteins in ATP-dependent expression of VCAM-1 and monocyte adherence in coronary artery endothelial cells. Arterioscler Thromb Vasc Biol 28, 2049-2055, doi: 10.1161/ATVBAHA.108.175356 (2008).

38. Vanderstocken, G. et al. P2Y2 receptor regulates VCAM-1 membrane and soluble forms and eosinophil accumulation during lung inflammation. J Immunol 185, 3702-3707, doi:10.4049/jimmunol.0903908 (2010).

39. Marchesi, V. T. The site of leucocyte emigration during inflammation. Quarterly journal of experimental physiology and cognate medical sciences 46, 115-118 (1961).

40. Marchesi, V. T. & Florey, H. W. Electron micrographic observations on the emigration of leucocytes. Quarterly journal of experimental physiology and cognate medical sciences 45, 343-348 (1960).

41. Sandilos, J. K. et al. Pannexin 1, an ATP release channel, is activated by caspase cleavage of its pore-associated C-terminal autoinhibitory region. The Journal of biological chemistry 287, 11303-11311, doi:10.1074/jbc.M111.323378 (2012).

42. Dourado, M., Wong, E. & Hackos, D. H. Pannexin-1 is blocked by its C-terminus through a delocalized non-specific interaction surface. PLoS One 9, e99596, doi:10.1371/journal.pone.0099596 (2014).

43. Li, J. M., Fan, L. M., Christie, M. R. & Shah, A. M. Acute tumor necrosis factor alpha signaling via NADPH oxidase in microvascular endothelial cells: role of p47phox phosphorylation and binding to TRAF4. Mol Cell Biol 25, 2320-2330, doi:10.1128/MCB.25.6.2320-2330.2005 (2005).

44. Marques-Fernandez, F. et al. TNFalpha induces survival through the FLIP-L-dependent activation of the MAPK/ERK pathway. Cell Death Dis 4, e493, doi:10.1038/cddis.2013.25 (2013).

45. Qiu, F. & Dahl, G. A permeant regulating its permeation pore: inhibition of pannexin 1 channels by ATP. Am J Physiol Cell Physiol 296, C250-255, doi:10.1152/ajpcell.00433.2008 (2009).

46. Akhand, A. A. et al. Nitric oxide controls src kinase activity through a sulfhydryl group modification-mediated Tyr-527-independent and Tyr-416-linked mechanism. The Journal of biological chemistry 274, 25821-25826 (1999).

47. Rahman, M. A. et al. S-nitrosylation at cysteine 498 of c-Src tyrosine kinase regulates nitric oxide-mediated cell invasion. The Journal of biological chemistry 285, 3806-3814, doi:10.1074/jbc.M109.059782 (2010).

48. VanUffelen, B. E., de Koster, B. M., Van den Broek, P. J., VanSteveninck, J. & Elferink, J. G. Modulation of neutrophil migration by exogenous gaseous nitric oxide. Journal of leukocyte biology 60, 94-100 (1996).

49. Kubes, P., Suzuki, M. & Granger, D. N. Nitric oxide: an endogenous modulator of leukocyte adhesion. Proc Natl Acad Sci USA 88, 4651-4655 (1991).

50. Kubes, P. & Granger, D. N. Nitric oxide modulates microvascular permeability. Am J Physiol 262, H611-615 (1992).

51. Dal Secco, D. et al. Neutrophil migration in inflammation: nitric oxide inhibits rolling, adhesion and induces apoptosis. Nitric oxide : biology and chemistry/official journal of the Nitric Oxide Society 9, 153-164 (2003).

52. Clark, S. C., Shenton, B. K., Dark, J. H. & Kirby, J. A. Neutrophil transmigration: modulation by pentoxifylline and nitric oxide. Biochemical Society transactions 25, 454S (1997).

53. Chello, M., Mastroroberto, P., Perticone, F., Celi, V. & Colonna, A. Nitric oxide modulation of neutrophil-endothelium interaction: difference between arterial and venous coronary bypass grafts. Journal of the American College of Cardiology 31, 823-826 (1998).

54. Grassi, F. Purinergic control of neutrophil activation. J Mol Cell Biol 2, 176-177, doi:10.1093/jmcb/mjq014 (2010).

55. Ayata, C. K. et al. Purinergic P2Y(2) receptors promote neutrophil infiltration and hepatocyte death in mice with acute liver injury. Gastroenterology 143, 1620-1629 e1624, doi:10.1053/j.gastro.2012.08.049 (2012).

56. Chen, Y. et al. ATP release guides neutrophil chemotaxis via P2Y2 and A3 receptors. Science 314, 1792-1795, doi:10.1126/science.1132559 (2006).

57. Bao, Y., Chen, Y., Ledderose, C., Li, L. & Junger, W. G. Pannexin 1 channels link chemoattractant receptor signaling to local excitation and global inhibition responses at the front and back of polarized neutrophils. The Journal of biological chemistry 288, 22650-22657, doi:10.1074/jbc.M113.476283 (2013).

58. Adamson et al., Pannexin1 is required for full activation of insulin-stimulated glucose uptake in adipocytes, MOLECULAR METABOLISM 4 (2015) 610-618.

---

What is claimed is:

1. A method for treating inflammation at a site of tissue injury, disease, or infection by inhibiting activation of venous endothelial cell Pannexin1, said method comprising administering to a subject in need thereof a pharmaceutical composition comprising an effective amount of an inhibitor of Pannexin1 activation, thereby treating said inflammation at a site of tissue injury, disease, or infection, wherein the inhibitor of Pannexin1 activation is an Intracellular Loop 2 (IL2) peptide consisting of amino acid sequence KYPIVEQYLKYGRKKQRRR (SEQ ID NO: 3), wherein said method inhibits inflammatory cell recruitment to said site of tissue injury, disease, or infection.

2. The method of claim 1, wherein said Pannexin1 is activated by a cytokine.

3. The method of claim 2, wherein said cytokine is Tumor Necrosis Factor alpha (TNFα).

4. The method of claim 1, wherein said inflammatory cell is a leukocyte.

5. The method of claim 4, wherein said leukocyte is a monocyte.

6. The method of claim 3, wherein said TNFα activates Pannexin1 by stimulating src family kinase (SFK) phosphorylation of Pannexin1.

7. The method of claim 1, wherein said inhibitor inhibits leukocyte adhesion to an endothelial cell.

8. The method of claim 7, wherein said endothelial cell is a venous endothelial cell.

9. The method of claim 1, wherein said inhibitor inhibits leukocyte emigration through a blood vessel wall.

10. The method of claim 9, wherein said blood vessel is a vein.

11. The method of claim 1, wherein said site comprises a localized focus of inflammation.

12. The method of claim 1, wherein said tissue injury, disease, or infection is selected from the group consisting of stroke, ischemic stroke, reperfusion injury, acute kidney injury, autoimmune disease, obesity, aortic aneurism, sepsis, inflammatory-associated hypertension, osteoarthritis, and atherosclerosis.

13. The method of claim 6, wherein said method inhibits TNFα activation of Pannexin1.

14. The method of claim 13, wherein said method inhibits ATP release from said venous endothelial cell.

15. The method of claim 1, wherein said inhibitor is directed against Pannexin1.

16. The method of claim 1, wherein said tissue injury, disease, or infection is selected from the group consisting of transplant rejection, rheumatoid arthritis, ulcerative colitis, and lupus glomerulonephritis.

17. A method for inhibiting inflammation and inflammatory cell recruitment at a site of tissue injury, disease, or infection wherein said inflammation and cell recruitment are associated with Pannexin1 activation in venous endothelial cells, said method comprising administering to a subject in need thereof a pharmaceutical composition comprising an effective amount of an inhibitor of said venous endothelial cell Pannexin1 activation, thereby inhibiting inflammation and inflammatory cell recruitment to a site of tissue injury, disease, or infection, wherein the inhibitor of Pannexin1 activation is an Intracellular Loop 2 (IL2) peptide consisting of amino acid sequence KYPIVEQYLKYGRKKQRRR (SEQ ID NO: 3).

18. The method of claim 17, wherein said inhibitor is directed against Pannexin1.

19. The method of claim 18, wherein said Pannexin1 is activated by a cytokine.

20. The method of claim 19, wherein said cytokine is TNFα.

21. The method of claim 17, wherein said inflammatory cell is a leukocyte.

22. The method of claim 21, wherein said leukocyte is a monocyte.

23. The method of claim 20, wherein said TNFα activates Pannexin1 by stimulating src family kinase (SFK) phosphorylation of Pannexin1.

24. The method of claim 17, wherein said inhibitor is directed against Pannexin1.

25. The method of claim 17, wherein said inhibitor inhibits leukocyte adhesion to an endothelial cell.

26. The method of claim 25, wherein said endothelial cell is a venous endothelial cell.

27. The method of claim 17, wherein said inhibitor inhibits leukocyte emigration through a blood vessel wall.

28. The method of claim 27, wherein said blood vessel is a vein.

29. The method of claim 17, wherein said site comprises a localized focus of inflammation.

30. The method of claim 17, wherein said tissue injury results from a stroke.

31. The method of claim 23, wherein said method inhibits TNFα activation of Pannexin1.

32. The method of claim 31, wherein said method inhibits ATP release from said venous endothelial cell.

33. The method of claim 17, wherein said tissue injury, disease, or infection is selected from the group consisting of sepsis, inflammatory-associated hypertension, stroke, transplant rejection, rheumatoid arthritis, ulcerative colitis, and lupus glomerulonephritis.

34. A method for inhibiting TNFα-induced ATP release from a venous endothelial cell, said method comprising contacting said venous endothelial cell with an effective amount of an inhibitor of Pannexin1 activity, wherein the inhibitor of Pannexin1 activation is an Intracellular Loop 2 (IL2) peptide consisting of amino acid sequence KYPIVEQYLKYGRKKQRRR (SEQ ID NO: 3).

35. The method of claim 34, wherein said method inhibits TNFα-induced SFK activation of Pannexin1.

36. The method of claim 35, wherein said method inhibits SFK phosphorylation of Pannexin1.

37. The method of claim 34, wherein said inhibitor is directed against Pannexin1.

38. The method of claim 34, wherein said venous endothelial cell is contacted with at least two inhibitors of Pannexin1 activity.

* * * * *

SEQUENCE LISTING

```
<160> NUMBER OF SEQ ID NOS: 10

<210> SEQ ID NO 1
<211> LENGTH: 10
<212> TYPE: PRT
<213> ORGANISM: Homo sapiens

<400> SEQUENCE: 1

Lys Tyr Pro Ile Val Glu Gln Tyr Leu Lys
1               5                   10

<210> SEQ ID NO 2
<211> LENGTH: 9
<212> TYPE: PRT
<213> ORGANISM: Human immunodeficiency virus

<400> SEQUENCE: 2

Tyr Gly Arg Lys Lys Gln Arg Arg Arg
1               5

<210> SEQ ID NO 3
<211> LENGTH: 19
<212> TYPE: PRT
<213> ORGANISM: Unknown
<220> FEATURE:
<223> OTHER INFORMATION: hybrid of human and HIV tat seq.

<400> SEQUENCE: 3

Lys Tyr Pro Ile Val Glu Gln Tyr Leu Lys Tyr Gly Arg Lys Lys Gln
1               5                   10                  15
```

Arg Arg Arg

<210> SEQ ID NO 4
<211> LENGTH: 10
<212> TYPE: PRT
<213> ORGANISM: Homo sapiens

<400> SEQUENCE: 4

Val Gly Gln Ser Leu Trp Glu Ile Ser Glu
1               5                   10

<210> SEQ ID NO 5
<211> LENGTH: 16
<212> TYPE: PRT
<213> ORGANISM: Homo sapiens

<400> SEQUENCE: 5

Arg Arg Leu Lys Val Tyr Glu Ile Leu Pro Thr Phe Asp Val Leu His
1               5                   10                  15

<210> SEQ ID NO 6
<211> LENGTH: 10
<212> TYPE: PRT
<213> ORGANISM: Homo sapiens

<400> SEQUENCE: 6

Ile Pro Thr Ser Leu Gln Thr Lys Gly Glu
1               5                   10

<210> SEQ ID NO 7
<211> LENGTH: 10
<212> TYPE: PRT
<213> ORGANISM: Unknown
<220> FEATURE:
<223> OTHER INFORMATION: scrambled human sequence

<400> SEQUENCE: 7

Ile Tyr Leu Tyr Val Glu Gln Lys Pro Tyr
1               5                   10

<210> SEQ ID NO 8
<211> LENGTH: 10
<212> TYPE: PRT
<213> ORGANISM: Unknown
<220> FEATURE:
<223> OTHER INFORMATION: synthetic peptide

<400> SEQUENCE: 8

Trp Arg Gln Ala Ala Phe Val Asp Ser Tyr
1               5                   10

<210> SEQ ID NO 9
<211> LENGTH: 15
<212> TYPE: PRT
<213> ORGANISM: Unknown
<220> FEATURE:
<223> OTHER INFORMATION: Phosphorylated epitope of Panx1 protein
<220> FEATURE:
<221> NAME/KEY: X
<222> LOCATION: (8)..(9)
<223> OTHER INFORMATION: X is a phosphorylated tyrosine

<400> SEQUENCE: 9

Cys Pro Ile Val Glu Gln Tyr Xaa Leu Lys Thr Lys Lys Asn Ser
1               5                   10                  15

```
<210> SEQ ID NO 10
<211> LENGTH: 14
<212> TYPE: PRT
<213> ORGANISM: Unknown
<220> FEATURE:
<223> OTHER INFORMATION: Non-phosporylated epitope of Panx-1

<400> SEQUENCE: 10

Cys Pro Ile Val Glu Gln Tyr Leu Lys Thr Lys Lys Asn Ser
1               5                   10
```